(12) United States Patent
Ruggles et al.

(10) Patent No.: US 7,939,304 B2
(45) Date of Patent: May 10, 2011

(54) MUTANT MT-SP1 PROTEASES WITH ALTERED SUBSTRATE SPECIFICITY OR ACTIVITY

(75) Inventors: Sandra Waugh Ruggles, South San Franciso, CA (US); Jack Nguyen, South San Franciso, CA (US)

(73) Assignee: Catalyst Biosciences, Inc., South San Francisco, CA (US)

( * ) Notice: Subject to any disclaimer, the term of this patent is extended or adjusted under 35 U.S.C. 154(b) by 777 days.

(21) Appl. No.: 11/104,110

(22) Filed: Apr. 12, 2005

(65) Prior Publication Data

US 2006/0002916 A1 Jan. 5, 2006

Related U.S. Application Data

(60) Provisional application No. 60/561,720, filed on Apr. 12, 2004.

(51) Int. Cl.
*C12N 9/00* (2006.01)
(52) U.S. Cl. .......................................................... 435/183
(58) Field of Classification Search ........................ None
See application file for complete search history.

(56) References Cited

U.S. PATENT DOCUMENTS

| | | | |
|---|---|---|---|
| 4,046,722 A | 9/1977 | Rowland | 260/6 |
| 4,046,784 A | 9/1977 | Gipson | 260/348.29 |
| 4,331,647 A | 5/1982 | Goldenberg | 424/1 |
| 4,348,376 A | 9/1982 | Goldenberg | 424/1 |
| 4,361,544 A | 11/1982 | Goldenberg | 424/1 |
| 4,444,744 A | 4/1984 | Goldenberg | 424/1.1 |
| 4,460,459 A | 7/1984 | Shaw et al. | 209/9 |
| 4,460,561 A | 7/1984 | Goldenberg | 424/1.1 |
| 4,468,457 A | 8/1984 | Goldenberg et al. | 435/69 |
| 4,624,846 A | 11/1986 | Goldenberg | 424/1.1 |
| 4,671,958 A | 6/1987 | Rodwell et al. | 424/85 |
| 4,818,709 A | 4/1989 | Primus et al. | 436/518 |
| 4,925,648 A | 5/1990 | Hansen et al. | 424/1.53 |
| 4,932,412 A | 6/1990 | Goldenberg | 600/431 |
| 5,223,409 A | 6/1993 | Ladner et al. | 435/69.7 |
| 5,332,567 A | 7/1994 | Goldenberg | 424/1.1 |
| 5,443,953 A | 8/1995 | Hansen et al. | 435/7.1 |
| 5,541,297 A | 7/1996 | Hansen et al. | 530/391.7 |
| 5,601,825 A | 2/1997 | Hansen et al. | 424/183.1 |
| 5,635,603 A | 6/1997 | Hansen et al. | 530/391.5 |

(Continued)

FOREIGN PATENT DOCUMENTS

EP 1361284 11/2003

(Continued)

OTHER PUBLICATIONS

Obers et al. The Activation of Matriptase Requries Its Noncatalytic Domains, Serine Protease Domain, and Its Cognate Inhibitor. Journal of Biological Chemistry, Jul. 18, 2003, 278(29):26773-79.*

(Continued)

*Primary Examiner* — Suzanne M. Noakes
(74) *Attorney, Agent, or Firm* — K&L Gates LLP; Stephanie Seidman

(57) ABSTRACT

MT-SP1 mutein proteases with altered specificity for the target molecules they cleave can be used to treat human diseases, such as cancer. Cleaving VEGF or VEGFR at certain substrate sequences with wild-type and mutein MT-SP1 proteases can be used to treat pathologies associated with angiogenesis.

17 Claims, 18 Drawing Sheets

U.S. PATENT DOCUMENTS

| | | | |
|---|---|---|---|
| 5,637,288 A | 6/1997 | Goldenberg et al. | 424/1.49 |
| 5,677,427 A | 10/1997 | Goldenberg et al. | 424/9.34 |
| 5,686,578 A | 11/1997 | Goldenberg | 530/387.3 |
| 5,698,178 A | 12/1997 | Goldenberg | 424/1.49 |
| 5,789,554 A | 8/1998 | Leung et al. | 530/387.3 |
| 5,922,302 A | 7/1999 | Goldenberg et al. | 424/1.41 |
| 5,972,616 A | 10/1999 | O'Brien et al. | 435/6 |
| 6,187,287 B1 | 2/2001 | Leung et al. | 424/9.1 |
| 6,271,012 B1 | 8/2001 | Van Eekelen et al. | 435/221 |
| 6,319,500 B1 | 11/2001 | Goldenberg | 424/178.1 |
| 6,383,775 B1 | 5/2002 | Duff et al. | 435/69.1 |
| 6,387,686 B2 | 5/2002 | Chadwick et al. | 435/235.1 |
| 6,649,741 B1 | 11/2003 | O'Brien et al. | 530/387.1 |
| 6,680,178 B2 | 1/2004 | Harris et al. | 435/23 |
| 7,030,231 B1 | 4/2006 | Craik et al. | 536/23.1 |
| 7,227,009 B2 | 6/2007 | Craik et al. | 536/23.1 |
| 7,335,504 B2 | 2/2008 | Haupts et al. | 435/226 |
| 7,439,226 B2 | 10/2008 | Roller et al. | 514/10 |
| 2002/0022243 A1 | 2/2002 | Harris et al. | 435/23 |
| 2002/0034776 A1 | 3/2002 | Bornscheuer et al. | 435/69.1 |
| 2003/0049689 A1 | 3/2003 | Edwards et al. | 435/7.1 |
| 2003/0050251 A1 | 3/2003 | Semple et al. | 514/19 |
| 2003/0068792 A1 | 4/2003 | Chen et al. | 435/183 |
| 2003/0119168 A1 | 6/2003 | Madison et al. | 435/226 |
| 2003/0199038 A1 | 10/2003 | Brody et al. | 435/69.1 |
| 2004/0072276 A1 | 4/2004 | Koltermann et al. | 435/23 |
| 2004/0081648 A1 | 4/2004 | Afeyan et al. | 424/94.63 |
| 2004/0115727 A1 | 6/2004 | Steward et al. | 435/7.1 |
| 2004/0146938 A1 | 7/2004 | Nguyen et al. | 435/7.1 |
| 2004/0175777 A1 | 9/2004 | Harris et al. | 435/23 |
| 2005/0002897 A1 | 1/2005 | Haupts et al. | 424/85.1 |
| 2005/0059126 A1 | 3/2005 | Haupts et al. | 435/183 |
| 2005/0130883 A1 | 6/2005 | Roller et al. | 514/10 |
| 2005/0158297 A1 | 7/2005 | Jensenius et al. | 424/94.6 |
| 2005/0175581 A1 | 8/2005 | Haupts et al. | 424/85.1 |
| 2005/0282228 A1 | 12/2005 | Mccoll et al. | 435/7.1 |
| 2006/0002916 A1 | 1/2006 | Ruggles et al. | 424/94.63 |
| 2006/0024289 A1 | 2/2006 | Ruggles et al. | 435/6 |
| 2006/0099625 A1 | 5/2006 | Craik et al. | 435/6 |
| 2006/0104979 A1 | 5/2006 | Craik et al. | 424/146.1 |
| 2006/0134086 A1 | 6/2006 | Chen et al. | 424/94.1 |
| 2006/0269538 A1 | 11/2006 | Koltermann et al. | 424/94.63 |
| 2007/0093443 A1 | 4/2007 | Madison et al. | 514/44 |
| 2008/0051559 A1 | 2/2008 | Craik et al. | 530/350 |
| 2008/0160558 A1 | 7/2008 | Koltermann et al. | 435/23 |
| 2009/0047210 A1 | 2/2009 | Ruggles et al. | 424/1.11 |
| 2009/0098103 A1 | 4/2009 | Madison et al. | 424/94.64 |
| 2009/0123452 A1 | 5/2009 | Madison | 424/94.64 |
| 2009/0136477 A1 | 5/2009 | Nguyen et al. | 424/94.64 |
| 2009/0155248 A1 | 6/2009 | Craik et al. | 424/133.1 |
| 2009/0175873 A1 | 7/2009 | Liu | 424/139.1 |
| 2009/0208440 A1 | 8/2009 | Haupts et al. | 424/70.14 |
| 2009/0208474 A1 | 8/2009 | Haupts et al. | 424/94.3 |

FOREIGN PATENT DOCUMENTS

| | | |
|---|---|---|
| EP | 1056466 | 1/2004 |
| EP | 1726643 | 11/2006 |
| EP | 1 504 117 | 7/2007 |
| JP | A-5-503211 | 6/1993 |
| WO | WO 91/05048 | 4/1991 |
| WO | 92/06204 | 4/1992 |
| WO | WO 00/53232 | 9/2000 |
| WO | 01/57194 | 8/2001 |
| WO | 01/94332 | 12/2001 |
| WO | WO 01/97794 | 12/2001 |
| WO | WO 02/08392 | 1/2002 |
| WO | WO 03/095670 | 11/2003 |
| WO | 2004/031733 | 4/2004 |
| WO | WO 2004/031733 A2 | 4/2004 |
| WO | WO 2004/113521 | 12/2004 |
| WO | WO 2004/113522 | 12/2004 |
| WO | WO 2005/110453 | 11/2005 |
| WO | WO 2006/067198 | 6/2006 |
| WO | WO 2006/125827 | 11/2006 |

OTHER PUBLICATIONS

Friedrich et al. *J. Biol. Chem.*, 277(3):2160-2168 (2002).

International Search Report for PCT/US2005/012488, mailed Mar. 3, 2006.

Ballinger, M.D., et al. "Furilisin: a variant of subtilisin BPN' engineered for cleaving tribasic substrates," Biochemistry, 35(42):13579-85, (1996).

Bianchi, E., et al., "Inhibiting viral proteases: challenges and opportunities," Biopolymers (Pept.Sci), 66:101-114, (2002).

Blow, D. M., et al., "Structure and mechanism of Chymotrypsin," Accounts of Chemical Research, 9:145-152, (1976).

Bowie, J.U. and R.T. Sauer. "Identifying determinants of folding and activity for a protein of unknown Structure," Proceedings of the National Academy of Sciences United States of America, 86(7):2152-2156, (1989).

Brady, L.W., et al., "Therapeutic and diagnostic uses of modified monoclonal antibodies," International Journal of Radiation Oncology, Biology, Physics, 13:1535-1544, (1987).

Corey D.R., et al., "Trypsin display on the surface of bacteriophage," Gene, 128(1):129-134, (1993).

Craik C.S., "Inhibitors for epithelial cancer associated proteases—structure based design," NIH Grant No. CA072006, (1997-2002).

Craik, C.S., et al., "Redesigning Trypsin: Alteration of Substrate Specificity, Catalytic Activity and Protein Conformation," Science, 228(4697):291-297, (1987).

Derbyshire, K.M., et al., "A simple and efficient procedure for saturation mutagenesis using mixed oligodeoxynucleotides," Gene, 46(2-3):145-152, (1986).

Dynan, W.S. and R. Tjian. "Control of eukaryotic messenger RNA synthesis by sequence-specific DNA-binding proteins," Nature 316(6031):774-778, (1985).

Fong, T.A., et al., "Inhibition of tumor growth, angiogenesis, and microcirculation by the novel Flk-1 inhibitor SU5416 as assessed by intravital multi-fluorescence videomicroscopy," Neoplasia, 1 (1):31-41, (1999). Erratum in: Neoplasia, 1(2):183, (1999).

Friedrich, R., et al., "Catalytic domain structures of MT-SP1/matriptase, a matrix-degrading transmembrane serine proteinase," Journal of Biological Chemistry, 277(3):2160-8, (2002).

Gerber, H.P., et al., "Vascular endothelial growth factor regulates endothelial cell survival through the phosphatidylinositol 3'-kinase/Akt signal transduction pathway. Requirement for Flk-1/KDR activation," Journal of Molecular Biology, 273(46):30336-30343, (1998).

Gill, S.C. and P.H. von Hippel, "Calculation of protein extinction coefficients from amino acid sequence data," Analytical Biochemistry, 182(2):319-26, (1989). Erratum in: Anal Biochem., 189(2):283, (1990).

Gillmor, S.A., et al., Compromise and accommodation in ecotin, a dimeric macromolecular inhibitor of serine proteases, Journal of Molecular Biology, 299(4):993-1003, (2000).

Harris, A.L., et al., "Anti-angiogenesis therapy and strategies for integrating it with adjuvant therapy," Recent Results in Cancer Research, 152:341-52, (1998).

Harris, A.L., et al., "Anti-angiogenesis therapy and strategies for integrating it with adjuvant therapy," Recent Results in Cancer Research, 152:341-352, (1998).

Harris, J.L., et al., "Rapid and general profiling of protease specificity by using combinatorial fluorogenic substrate libraries," Proceedings of the National Academy of Sciences of the United States of America, 97(14):7754-9, (2000).

He, G.P., et al., "A eukaryotic transcriptional represser with carboxypeptidase activity," Nature, 378:92-96, (1995).

Hopfner, K.P., et al., "Coagulation factor IXa: the relaxed conformation of Tyr99 blocks substrate binding," Structure, 7(8):989-96, (1999).

Jameson, G.W., et al., "Determination of the operational molarity of solutions of bovine alpha-chymotrypsin, trypsin, thrombin and factor Xa by spectrofluorimetric titration," Biochemical Journal, 131(1):107-17, (1973).

Kim, K.J., et al., "Inhibition of vascular endothelial growth factor-induced angiogenesis suppresses tumour growth in vivo," Nature, 362(6423):841-844, (1993).

Klement, G., et al., "Continuous low-dose therapy with vinblastine and VEGF receptor-2 antibody induces sustained tumor regression without overt toxicity," Journal of Clinical Investigation, 105(8):R15-24, (2000).

Kuo, C.J., et al., "Comparative evaluation of the antitumor activity of antiangiogenic proteins delivered by gene transfer," Proceedings of the National Academy of Sciences of the United States of America, 98(8):4605-10, (2001).

Legendre, D., et al., "Display of active subtilisin 309 on phage: analysis of parameters influencing the selection of subtilisin variants with changed substrate specificity from libraries using phosphonylating inhibitors," Journal of Molecular Biology, 296(1):87-102, (2000).

Lin, P., et al., "Inhibition of tumor growth by targeting tumor endothelium using a soluble vascular endothelial growth factor receptor," Cell Growth & Differentiation, 9(1):49-58, (1998).

Lowman, H.B., et al., "Selecting high-affinity binding proteins by monovalent phage display," Biochemistry, 30(45):10832-10837, (1991).

McMahon, G., et al., "VEGF receptor signaling in tumor angiogenesis," Oncologist, 5 Suppl 1:3-10, (2000).

Millauer, B., et al., "Glioblastoma growth inhibited in vivo by a dominant-negative Flk-1 mutant," Nature, 367(6463):576-579, (1994).

Needleman, S.B. and C.D. Wunsch., "A general method applicable to the search for similarities in the amino acid sequence of two proteins," Journal of Molecular Biology, 48(3):443-53, (1970).

Ner, S.S., et al., "A simple and efficient procedure for generating random point mutations and for codon replacements using mixed oligodeoxynucleotides," DNA, 7(2):127-134, (1988).

Pastan, I., et al., "Immunotoxins," Cell, 47(5):641-8, (1986).

Perona, J.J., et al., "Structural origins of substrate discrimination in trypsin and chymotrypsin," Biochemistry, 34(5):1489-1499, (1995).

Porteu, M., et al., "Human neutrophil elastase releases a ligand-binding fragment from the 75-kDa tumor necrosis factor (TNF) receptor. Comparison with the proteolytic activity responsible for shedding of TNF receptors from stimulated neutrophils," Journal of Biological Chemistry, 266(28):18846-18853, (1991).

Prewett, M., et al., "Antivascular endothelial growth factor receptor (fetal liver kinase 1) monoclonal antibody inhibits tumor angiogenesis and growth of several mouse and human tumors," Cancer Research, 59(20):5209-18, (1999).

Reidhaar-Olson, J.F. and R.T. Sauer, "Combinatorial cassette mutagenesis as a probe of the informational content of protein sequences," Science, 241(4861):53-57, (1988).

Ribatti, D., et al., "Angiogenesis and anti-angiogenesis in hematological malignancies," Journal of Hematotherapy and Stem Cell Research, 12(1):11-22, (2003).

Ruggles, S.W. et al., "Characterization of structural deteriminants of granzyme B reveals potent mediators of extended substrate specificity," Journal of Biological Chemistry, 279(29):30751-30759, (2004). Epub. Date May 3, 2004.

Schecter, I. and A. Berger, "On the size of the active site in Proteases. I., Papain," Biochemical and Biophysical Research Communications, 27(2):157-162, (1967).

Shaheen, R.M., et al., "Antiangiogenic therapy targeting the tyrosine kinase receptor for vascular endothelial growth factor receptor inhibits the growth of colon cancer liver metastasis and induces tumor and endothelial cell apoptosis," Cancer Research, 59(21):5412-5419, (1999).

Takeuchi, T., et al., "Cellular localization of membrane-type serine protease 1 and identification of protease-activated receptor-2 and single-chain urokinase-type plasminogen activator as substrates," Journal of Biological Chemistry, 275(34):26333-26342, (2000).

van Kessel, K.P., et al., "Inactivation of recombinant human tumor necrosis factor-alpha by proteolytic enzymes released from stimulated human neutrophils," Journal of Immunology, 147(11):3862-3868, (1991).

Vitetta, E.S., et al., "Redesigning nature's poisons to create antitumor reagents," Science, 238(4830):1098-1104, (1987).

Waltenberger, J., et al., "Different signal transduction properties of KDR and Flt1, two receptors for vascular endothelial growth factor," Journal of Biological Chemistry, 269(43):26988-26995, (1994).

Wang, S.X., et al., "Crystal structure of thrombin-ecotin reveals conformational changes and extended interactions," Biochemistry, 40(34):10038-10046, (2001).

Waugh, S.M., et al., "The structure of the pro-apoptotic protease granzyme B reveals the molecular determinants of its specificity," Nature Structure Biology, (9):762-765, (2000).

Wawrzynczak and Thorpe, in *Introduction to the Cellular and Molecular Biology of Cancer*, Oxford University Press, Oxford, Chapter 18, Eds. M. Franks and N.M. Teich, pp. 378-410, (1986).

Yilmaz, A., et al., "p38 MAPK inhibition is critically involved in VEGFR-2-mediated endothelial cell survival," Biochemical and Biophysical Research Communications, 306(3):730-736, (2003).

Yoshiji, H., et al., "KDR/Flk-1 is a major regulator of vascular endothelial growth factor-induced tumor development and angiogenesis in murine hepatocellular carcinoma cells," Hepatology, 30(5):1179-1186, (1999).

Lasters et al., "Enzymatic properties of phage-displayed fragments of human plasminogen," European J Biochemistry 244:946-952 (1997).

Lien et al., "Combinatorial strategies for the discovery of novel protease specificities," Combi Chem High Throughput Screening 2:73-90 (1999).

Lin, C., et al., "Molecular cloning of cDNA for matriptase, a matrix-degrading serine protease with tryspin-like activity," Journal of Biological Chemistry, 274:18231-18236 (1999).

Sidhu et al., "Phage display for selection of novel binding peptides," Methods in Enzymology 328:333-363 (2000).

Soumillion et al., "Phage display of enzymes and in vitro selection for catalytic activity," App Biochem and Biotechnology 47:175-189 (1994).

Takeuchi, T., et al., "Reverse biochemistry: use of macromolecular protease inhibitors to dissect complex biological processes and identify a membrane-type serine protease in epithelial cancer and normal tissue," Proc. Natl. Acad. Sci., U.S.A., 96:11054-1161 (1999).

Bornscheuer, U. and M. Pohl, "Improved biocatalysts by directed evolution and rational protein design," Curr Opin in Chem Biol 5(2):137-143 (2001).

Caputo et al., "Conversion of the substrate specificity of mouse proteinase granzyme B," Nature Structural Biology, 1(6):364-367 (1994).

Harris et al., "Definition and redesign of the extended substrate specificity of granzyme B," J Biol Chem 273(42):27364-27373 (1998).

Harris, J. and C. Craik, "Engineering Enzyme Specificity," Current Opinion in Chemical Biology 2(1):127-132 (1998).

Kuo et al., "Comparative evaluation of the antitumor activity of antiangiogenic proteins delivered by gene transfer," Proc. Natl. Acad. Sci. U.S.A. 98(8):4605-4610 (2001).

Mignatti, P. and D. Rifkin, "Biology and biochemistry of proteinases in tumor invasion," Physiol. Rev. 73:161-195 (1993).

International Search Report, issued Jul. 27, 2007, in connection with International Patent Application No. PCT/US2006/041165.

Written Opinion, issued Feb. 12, 2008, in connection with International Patent Application No. PCT/US2006/041165.

Examination Report, issued Aug. 18, 2008, in connection with Australian Patent Application No. 2005244271.

Examination Report, issued Dec. 22, 2008, in connection with Canadian Patent Application No. 2,562,729.

Examination Report, issued Sep. 10, 2009, in connection with European Patent Application No. 05778153.6.

Office Action, issued Nov. 20, 2009, in connection with U.S. Appl. No. 12/005,953.

* cited by examiner

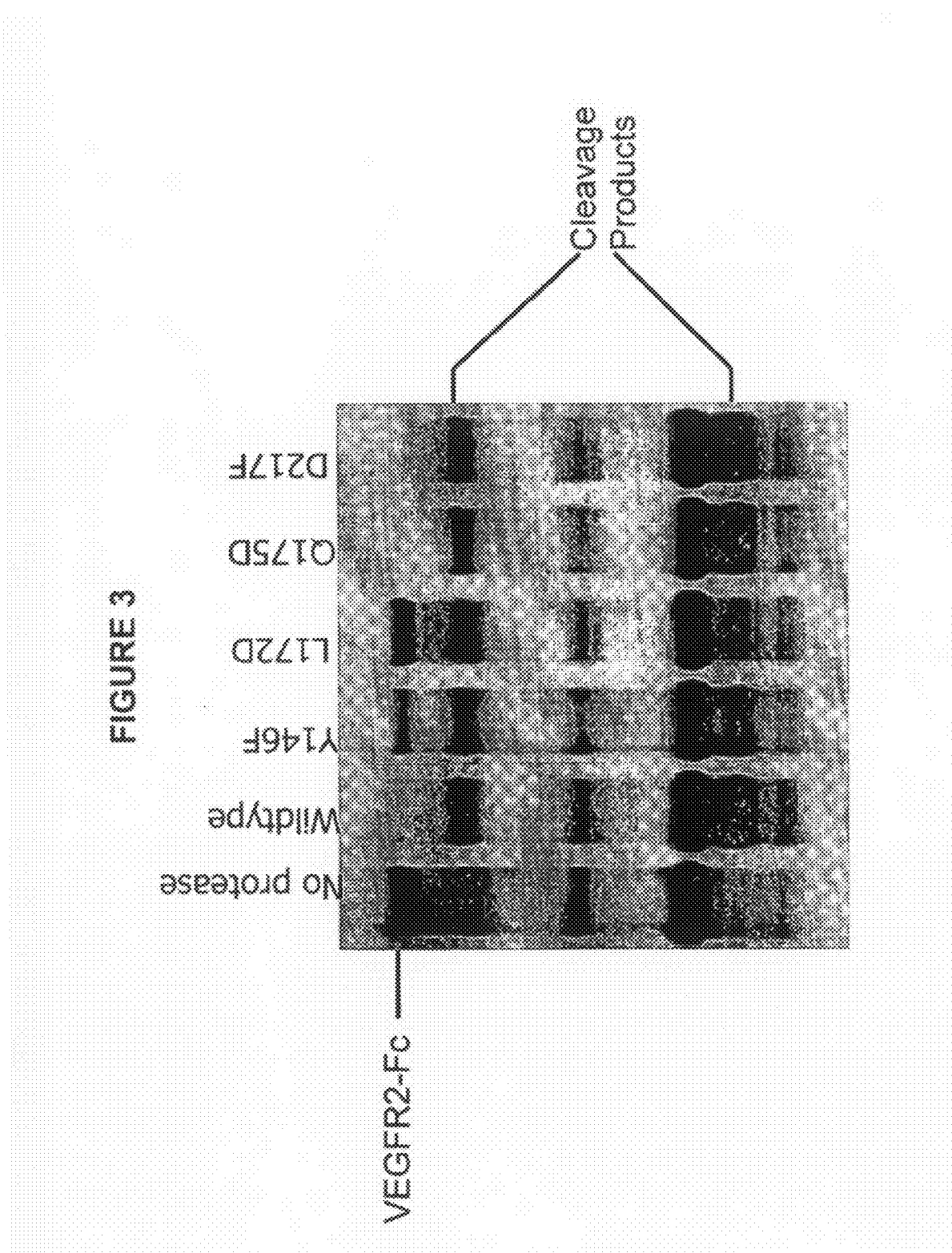

FIGURE 7
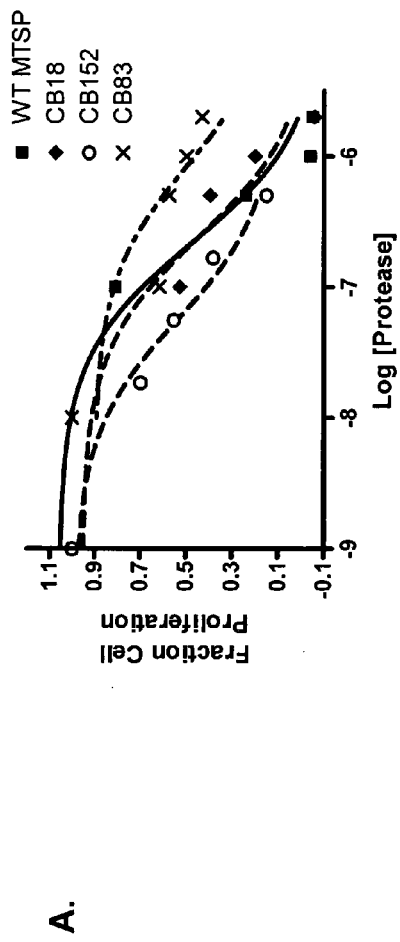
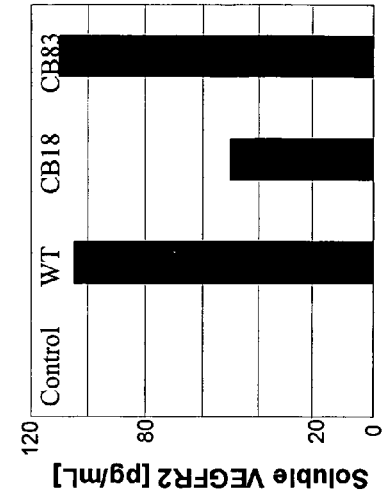
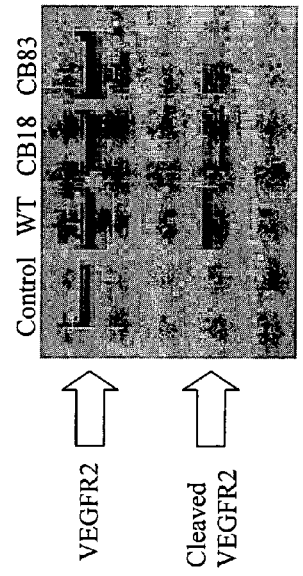

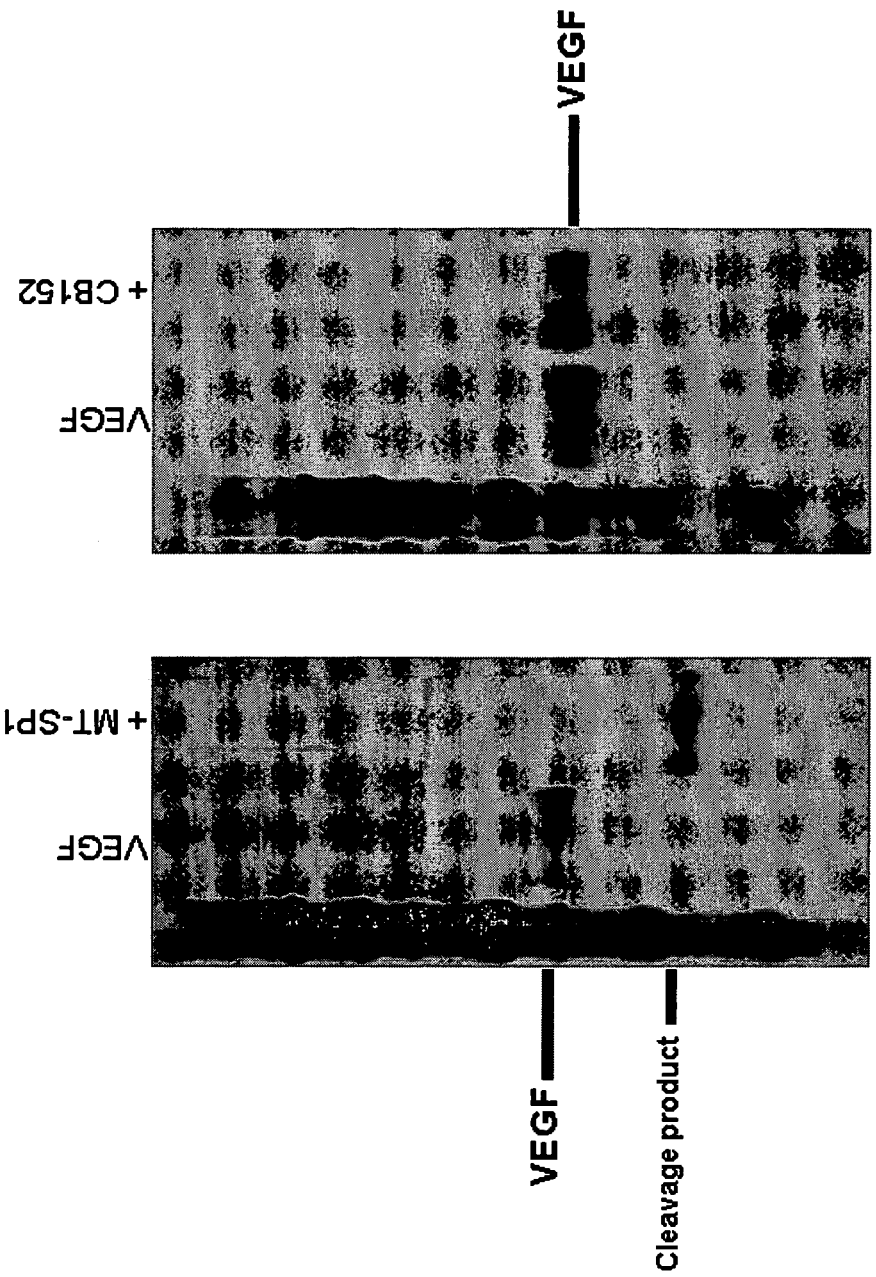

```
                          SEQUENCE LISTING

<160> NUMBER OF SEQ ID NOS: 19

<210> SEQ ID NO 1
<211> LENGTH: 855
<212> TYPE: PRT
<213> ORGANISM: Homo sapiens

<400> SEQUENCE: 1

Met Gly Ser Asp Arg Ala Arg Lys Gly Gly Gly Pro Lys Asp Phe
1               5                   10                  15

Gly Ala Gly Leu Lys Tyr Asn Ser Arg His Glu Lys Val Asn Gly Leu
                20                  25                  30

Glu Glu Gly Val Glu Phe Leu Pro Val Asn Asn Val Lys Lys Val Glu
                35                  40                  45

Lys His Gly Pro Gly Arg Trp Val Val Leu Ala Ala Val Leu Ile Gly
        50                  55                  60

Leu Leu Leu Val Leu Leu Gly Ile Gly Phe Leu Val Trp His Leu Gln
65                  70                  75                  80

Tyr Arg Asp Val Arg Val Gln Lys Val Phe Asn Gly Tyr Met Arg Ile
                85                  90                  95

Thr Asn Glu Asn Phe Val Asp Ala Tyr Glu Asn Ser Asn Ser Thr Glu
                100                 105                 110

Phe Val Ser Leu Ala Ser Lys Val Lys Asp Ala Leu Lys Leu Leu Tyr
            115                 120                 125

Ser Gly Val Pro Phe Leu Gly Pro Tyr His Lys Glu Ser Ala Val Thr
        130                 135                 140

Ala Phe Ser Glu Gly Ser Val Ile Ala Tyr Tyr Trp Ser Glu Phe Ser
145                 150                 155                 160

Ile Pro Gln His Leu Val Glu Glu Ala Glu Arg Val Met Ala Glu Glu
                165                 170                 175

Arg Val Val Met Leu Pro Pro Arg Ala Arg Ser Leu Lys Ser Phe Val
                180                 185                 190

Val Thr Ser Val Val Ala Phe Pro Thr Asp Ser Lys Thr Val Gln Arg
            195                 200                 205

Thr Gln Asp Asn Ser Cys Ser Phe Gly Leu His Ala Arg Gly Val Glu
        210                 215                 220

Leu Met Arg Phe Thr Thr Pro Gly Phe Pro Asp Ser Pro Tyr Pro Ala
225                 230                 235                 240

His Ala Arg Cys Gln Trp Ala Leu Arg Gly Asp Ala Asp Ser Val Leu
                245                 250                 255

Ser Leu Thr Phe Arg Ser Phe Asp Leu Ala Ser Cys Asp Glu Arg Gly
                260                 265                 270

Ser Asp Leu Val Thr Val Tyr Asn Thr Leu Ser Pro Met Glu Pro His
            275                 280                 285

Ala Leu Val Gln Leu Cys Gly Thr Tyr Pro Pro Ser Tyr Asn Leu Thr
        290                 295                 300

Phe His Ser Ser Gln Asn Val Leu Leu Ile Thr Leu Ile Thr Asn Thr
305                 310                 315                 320
```

-continued

```
Glu Arg Arg His Pro Gly Phe Glu Ala Thr Phe Phe Gln Leu Pro Arg
            325                 330                 335

Met Ser Ser Cys Gly Gly Arg Leu Arg Lys Ala Gln Gly Thr Phe Asn
        340                 345                 350

Ser Pro Tyr Tyr Pro Gly His Tyr Pro Pro Asn Ile Asp Cys Thr Trp
            355                 360                 365

Asn Ile Glu Val Pro Asn Asn Gln His Val Lys Val Ser Phe Lys Phe
    370                 375                 380

Phe Tyr Leu Leu Glu Pro Gly Val Pro Ala Gly Thr Cys Pro Lys Asp
385                 390                 395                 400

Tyr Val Glu Ile Asn Gly Glu Lys Tyr Cys Glu Arg Ser Gln Phe
                405                 410                 415

Val Val Thr Ser Asn Ser Asn Lys Ile Thr Val Arg Phe His Ser Asp
            420                 425                 430

Gln Ser Tyr Thr Asp Thr Gly Phe Leu Ala Glu Tyr Leu Ser Tyr Asp
            435                 440                 445

Ser Ser Asp Pro Cys Pro Gly Gln Phe Thr Cys Arg Thr Gly Arg Cys
450                 455                 460

Ile Arg Lys Glu Leu Arg Cys Asp Gly Trp Ala Asp Cys Thr Asp His
465                 470                 475                 480

Ser Asp Glu Leu Asn Cys Ser Cys Asp Ala Gly His Gln Phe Thr Cys
            485                 490                 495

Lys Asn Lys Phe Cys Lys Pro Leu Phe Trp Val Cys Asp Ser Val Asn
            500                 505                 510

Asp Cys Gly Asp Asn Ser Asp Glu Gln Gly Cys Ser Cys Pro Ala Gln
            515                 520                 525

Thr Phe Arg Cys Ser Asn Gly Lys Cys Leu Ser Lys Ser Gln Gln Cys
            530                 535                 540

Asn Gly Lys Asp Asp Cys Gly Asp Gly Ser Asp Glu Ala Ser Cys Pro
545                 550                 555                 560

Lys Val Asn Val Val Thr Cys Thr Lys His Thr Tyr Arg Cys Leu Asn
                565                 570                 575

Gly Leu Cys Leu Ser Lys Gly Asn Pro Glu Cys Asp Gly Lys Glu Asp
            580                 585                 590

Cys Ser Asp Gly Ser Asp Glu Lys Asp Cys Asp Cys Gly Leu Arg Ser
            595                 600                 605

Phe Thr Arg Gln Ala Arg Val Val Gly Gly Thr Asp Ala Asp Glu Gly
            610                 615                 620

Glu Trp Pro Trp Gln Val Ser Leu His Ala Leu Gly Gln Gly His Ile
625                 630                 635                 640

Cys Gly Ala Ser Leu Ile Ser Pro Asn Trp Leu Val Ser Ala Ala His
            645                 650                 655

Cys Tyr Ile Asp Asp Arg Gly Phe Arg Tyr Ser Asp Pro Thr Gln Trp
            660                 665                 670

Thr Ala Phe Leu Gly Leu His Asp Gln Ser Gln Arg Ser Ala Pro Gly
            675                 680                 685

Val Gln Glu Arg Arg Leu Lys Arg Ile Ile Ser His Pro Phe Phe Asn
            690                 695                 700

Asp Phe Thr Phe Asp Tyr Asp Ile Ala Leu Leu Glu Leu Glu Lys Pro
705                 710                 715                 720

Ala Glu Tyr Ser Ser Met Val Arg Pro Ile Cys Leu Pro Asp Ala Ser
                725                 730                 735

His Val Phe Pro Ala Gly Lys Ala Ile Trp Val Thr Gly Trp Gly His
            740                 745                 750
```

```
Thr Gln Tyr Gly Gly Thr Gly Ala Leu Ile Leu Gln Lys Gly Glu Ile
        755                 760                 765
Arg Val Ile Asn Gln Thr Thr Cys Glu Asn Leu Leu Pro Gln Gln Ile
        770                 775                 780
Thr Pro Arg Met Met Cys Val Gly Phe Leu Ser Gly Gly Val Asp Ser
785                 790                 795                 800
Cys Gln Gly Asp Ser Gly Gly Pro Leu Ser Ser Val Glu Ala Asp Gly
                805                 810                 815
Arg Ile Phe Gln Ala Gly Val Val Ser Trp Gly Asp Gly Cys Ala Gln
                820                 825                 830
Arg Asn Lys Pro Gly Val Tyr Thr Arg Leu Pro Leu Phe Arg Asp Trp
                835                 840                 845
Ile Lys Glu Asn Thr Gly Val
        850                 855

<210> SEQ ID NO 2
<211> LENGTH: 258
<212> TYPE: PRT
<213> ORGANISM: Homo sapiens

<400> SEQUENCE: 2

Asp Glu Lys Asp Cys Asp Cys Gly Leu Arg Ser Phe Thr Arg Gln Ala
1               5                   10                  15
Arg Val Val Gly Gly Thr Asp Ala Asp Glu Gly Glu Trp Pro Trp Gln
            20                  25                  30
Val Ser Leu His Ala Leu Gly Gln Gly His Ile Cys Gly Ala Ser Leu
        35                  40                  45
Ile Ser Pro Asn Trp Leu Val Ser Ala Ala His Cys Tyr Ile Asp Asp
    50                  55                  60
Arg Gly Phe Arg Tyr Ser Asp Pro Thr Gln Trp Thr Ala Phe Leu Gly
65                  70                  75                  80
Leu His Asp Gln Ser Gln Arg Ser Ala Pro Gly Val Gln Glu Arg Arg
                85                  90                  95
Leu Lys Arg Ile Ile Ser His Pro Phe Phe Asn Asp Phe Thr Phe Asp
            100                 105                 110
Tyr Asp Ile Ala Leu Leu Glu Leu Glu Lys Pro Ala Glu Tyr Ser Ser
        115                 120                 125
Met Val Arg Pro Ile Cys Leu Pro Asp Ala Ser His Val Phe Pro Ala
    130                 135                 140
Gly Lys Ala Ile Trp Val Thr Gly Trp Gly His Thr Gln Tyr Gly Gly
145                 150                 155                 160
Thr Gly Ala Leu Ile Leu Gln Lys Gly Glu Ile Arg Val Ile Asn Gln
                165                 170                 175
Thr Thr Cys Glu Asn Leu Leu Pro Gln Gln Ile Thr Pro Arg Met Met
            180                 185                 190
Cys Val Gly Phe Leu Ser Gly Gly Val Asp Ser Cys Gln Gly Asp Ser
        195                 200                 205
Gly Gly Pro Leu Ser Ser Val Glu Ala Asp Gly Arg Ile Phe Gln Ala
    210                 215                 220
Gly Val Val Ser Trp Gly Asp Gly Cys Ala Gln Arg Asn Lys Pro Gly
225                 230                 235                 240
Val Tyr Thr Arg Leu Pro Leu Phe Arg Asp Trp Ile Lys Glu Asn Thr
                245                 250                 255
Gly Val
```

```
<210> SEQ ID NO 3
<211> LENGTH: 230
<212> TYPE: PRT
<213> ORGANISM: Homo sapiens

<400> SEQUENCE: 3

Ile Val Asn Gly Glu Asp Ala Val Pro Gly Ser Trp Pro Trp Gln Val
1               5                   10                  15

Ser Leu Gln Asp Lys Thr Gly Phe His Phe Cys Gly Gly Ser Leu Ile
            20                  25                  30

Ser Glu Asp Trp Val Val Thr Ala Ala His Cys Gly Val Arg Thr Ser
        35                  40                  45

Asp Val Val Ala Gly Glu Phe Asp Gln Gly Ser Asp Glu Glu Asn
    50                  55                  60

Ile Gln Val Leu Lys Ile Ala Lys Val Phe Lys Asn Pro Lys Phe Ser
65                  70                  75                  80

Ile Leu Thr Val Asn Asn Asp Ile Thr Leu Leu Lys Leu Ala Thr Pro
                85                  90                  95

Ala Arg Phe Ser Gln Thr Val Ser Ala Val Cys Leu Pro Ser Ala Asp
            100                 105                 110

Asp Asp Phe Pro Ala Gly Thr Leu Cys Ala Thr Thr Gly Trp Gly Lys
        115                 120                 125

Thr Lys Tyr Asn Ala Asn Lys Thr Pro Asp Lys Leu Gln Gln Ala Ala
    130                 135                 140

Leu Pro Leu Leu Ser Asn Ala Glu Cys Lys Lys Ser Trp Gly Arg Arg
145                 150                 155                 160

Ile Thr Asp Val Met Ile Cys Ala Gly Ala Ser Gly Val Ser Ser Cys
                165                 170                 175

Met Gly Asp Ser Gly Gly Pro Leu Val Cys Gln Lys Asp Gly Ala Trp
            180                 185                 190

Thr Leu Val Gly Ile Val Ser Trp Gly Ser Asp Thr Cys Ser Thr Ser
        195                 200                 205

Ser Pro Gly Val Tyr Ala Arg Val Thr Lys Leu Ile Pro Trp Val Gln
    210                 215                 220

Lys Ile Leu Ala Ala Asn
225                 230

<210> SEQ ID NO 4
<211> LENGTH: 726
<212> TYPE: DNA
<213> ORGANISM: Homo sapiens

<400> SEQUENCE: 4
gttgttgggg gcacggatgc ggatgagggc gagtggccct ggcaggtaag cctgcatgct      60
ctgggccagg gccacatctg cggtgcttcc ctcatctctc ccaactggct ggtctctgcc     120
gcacactgct acatcgatga cagaggattc aggtactcag accccacgca gtggacggcc     180
ttcctgggct tgcacgacca gagccagcgc agcgccctg gggtgcagga gcgcaggctc     240
aagcgcatca tctcccaccc cttcttcaat gacttcacct tcgactatga catcgcgctg     300
ctggagctgg agaaaccggc agagtacagc tccatggtgc ggcccatctg cctgccggac     360
gcctcccatg tcttccctgc cggcaaggcc atctgggtca cgggctgggg acacacccag     420
tatggaggca ctggcgcgct gatcctgcaa aagggtgaga tccgcgtcat caaccagacc     480
acctgcgaga acctcctgcc gcagcagatc acgcgcgca tgatgtgcgt gggcttcctc     540
agcggcggcg tggactcctg ccaggtgat tccgggggac ccctgtccag cgtggaggcg     600
```

```
gatgggcgga tcttccaggc cggtgtggtg agctggggag acggctgcgc tcagaggaac    660
aagccaggcg tgtacacaag gctccctctg tttcgggact ggatcaaaga gaacactggg    720
gtatag                                                                726
```

```
<210> SEQ ID NO 5
<211> LENGTH: 4
<212> TYPE: PRT
<213> ORGANISM: Homo sapiens

<400> SEQUENCE: 5

Ile Ile Gly Gly
1

<210> SEQ ID NO 6
<211> LENGTH: 4
<212> TYPE: PRT
<213> ORGANISM: Homo sapiens

<400> SEQUENCE: 6

Val Val Gly Gly
1

<210> SEQ ID NO 7
<211> LENGTH: 4
<212> TYPE: PRT
<213> ORGANISM: Homo sapiens

<400> SEQUENCE: 7

Ile Val Gly Gly
1

<210> SEQ ID NO 8
<211> LENGTH: 764
<212> TYPE: PRT
<213> ORGANISM: Homo sapiens

<400> SEQUENCE: 8

Lys Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175
```

-continued

```
Ile Ser Trp Asp Ser Lys Lys Gly Phe Thr Ile Pro Ser Tyr Met Ile
            180                 185                 190
Ser Tyr Ala Gly Met Val Phe Cys Glu Ala Lys Ile Asn Asp Glu Ser
        195                 200                 205
Tyr Gln Ser Ile Met Tyr Ile Val Val Val Gly Tyr Arg Ile Tyr
    210                 215                 220
Asp Val Val Leu Ser Pro Ser His Gly Ile Glu Leu Ser Val Gly Glu
225                 230                 235                 240
Lys Leu Val Leu Asn Cys Thr Ala Arg Thr Glu Leu Asn Val Gly Ile
                245                 250                 255
Asp Phe Asn Trp Glu Tyr Pro Ser Ser Lys His Gln His Lys Lys Leu
            260                 265                 270
Val Asn Arg Asp Leu Lys Thr Gln Ser Gly Ser Glu Met Lys Lys Phe
        275                 280                 285
Leu Ser Thr Leu Thr Ile Asp Gly Val Thr Arg Ser Asp Gln Gly Leu
    290                 295                 300
Tyr Thr Cys Ala Ala Ser Ser Gly Leu Met Thr Lys Lys Asn Ser Thr
305                 310                 315                 320
Phe Val Arg Val His Glu Lys Pro Phe Val Ala Phe Gly Ser Gly Met
                325                 330                 335
Glu Ser Leu Val Glu Ala Thr Val Gly Glu Arg Val Arg Ile Pro Ala
            340                 345                 350
Lys Tyr Leu Gly Tyr Pro Pro Pro Glu Ile Lys Trp Tyr Lys Asn Gly
        355                 360                 365
Ile Pro Leu Glu Ser Asn His Thr Ile Lys Ala Gly His Val Leu Thr
    370                 375                 380
Ile Met Glu Val Ser Glu Arg Asp Thr Gly Asn Tyr Thr Val Ile Leu
385                 390                 395                 400
Thr Asn Pro Ile Ser Lys Glu Lys Gln Ser His Val Val Ser Leu Val
                405                 410                 415
Val Tyr Val Pro Pro Gln Ile Gly Glu Lys Ser Leu Ile Ser Pro Val
            420                 425                 430
Asp Ser Tyr Gln Tyr Gly Thr Thr Gln Thr Leu Thr Cys Thr Val Tyr
        435                 440                 445
Ala Ile Pro Pro Pro His His Ile His Trp Tyr Trp Gln Leu Glu Glu
    450                 455                 460
Glu Cys Ala Asn Glu Pro Ser Gln Ala Val Ser Val Thr Asn Pro Tyr
465                 470                 475                 480
Pro Cys Glu Glu Trp Arg Ser Val Glu Asp Phe Gln Gly Gly Asn Lys
                485                 490                 495
Ile Glu Val Asn Lys Asn Gln Phe Ala Leu Ile Glu Gly Lys Asn Lys
            500                 505                 510
Thr Val Ser Thr Leu Val Ile Gln Ala Ala Asn Val Ser Ala Leu Tyr
        515                 520                 525
Lys Cys Glu Ala Val Asn Lys Val Gly Arg Gly Glu Arg Val Ile Ser
    530                 535                 540
Phe His Val Thr Arg Gly Pro Glu Ile Thr Leu Gln Pro Asp Met Gln
545                 550                 555                 560
Pro Thr Glu Gln Glu Ser Val Ser Leu Trp Cys Thr Ala Asp Arg Ser
                565                 570                 575
Thr Phe Glu Asn Leu Thr Trp Tyr Lys Leu Gly Pro Gln Pro Leu Pro
            580                 585                 590
Ile His Val Gly Glu Leu Pro Thr Pro Val Cys Lys Asn Leu Asp Thr
```

```
                        595                 600                 605
Leu Trp Lys Leu Asn Ala Thr Met Phe Ser Asn Ser Thr Asn Asp Ile
        610                 615                 620
Leu Ile Met Glu Leu Lys Asn Ala Ser Leu Gln Asp Gln Gly Asp Tyr
625                 630                 635                 640
Val Cys Leu Ala Gln Asp Arg Lys Thr Lys Lys Arg His Cys Val Val
                645                 650                 655
Arg Gln Leu Thr Val Leu Glu Arg Val Ala Pro Thr Ile Thr Gly Asn
                    660                 665                 670
Leu Glu Asn Gln Thr Thr Ser Ile Gly Glu Ser Ile Glu Val Ser Cys
            675                 680                 685
Thr Ala Ser Gly Asn Pro Pro Pro Gln Ile Met Trp Phe Lys Asp Asn
        690                 695                 700
Glu Thr Leu Val Glu Asp Ser Gly Ile Val Leu Lys Asp Gly Asn Arg
705                 710                 715                 720
Asn Leu Thr Ile Arg Arg Val Arg Lys Glu Asp Glu Gly Leu Tyr Thr
                    725                 730                 735
Cys Gln Ala Cys Ser Val Leu Gly Cys Ala Lys Val Glu Ala Phe Phe
                740                 745                 750
Ile Ile Glu Gly Ala Gln Glu Lys Thr Asn Leu Glu
            755                 760

<210> SEQ ID NO 9
<211> LENGTH: 592
<212> TYPE: PRT
<213> ORGANISM: Homo sapiens

<400> SEQUENCE: 9

Ile Ile Ile Leu Val Gly Thr Ala Val Ile Ala Met Phe Phe Trp Leu
1               5                   10                  15
Leu Leu Val Ile Ile Leu Arg Thr Val Lys Arg Ala Asn Gly Gly Glu
                20                  25                  30
Leu Lys Thr Gly Tyr Leu Ser Ile Val Met Asp Pro Asp Glu Leu Pro
            35                  40                  45
Leu Asp Glu His Cys Glu Arg Leu Pro Tyr Asp Ala Ser Lys Trp Glu
        50                  55                  60
Phe Pro Arg Asp Arg Leu Lys Leu Gly Lys Pro Leu Gly Arg Gly Ala
65                  70                  75                  80
Phe Gly Gln Val Ile Glu Ala Asp Ala Phe Gly Ile Asp Lys Thr Ala
                85                  90                  95
Thr Cys Arg Thr Val Ala Val Lys Met Leu Lys Glu Gly Ala Thr His
                100                 105                 110
Ser Glu His Arg Ala Leu Met Ser Glu Leu Lys Ile Leu Ile His Ile
            115                 120                 125
Gly His His Leu Asn Val Val Asn Leu Leu Gly Ala Cys Thr Lys Pro
        130                 135                 140
Gly Gly Pro Leu Met Val Ile Val Glu Phe Cys Lys Phe Gly Asn Leu
145                 150                 155                 160
Ser Thr Tyr Leu Arg Ser Lys Arg Asn Glu Phe Val Pro Tyr Lys Thr
                165                 170                 175
Lys Gly Ala Arg Phe Arg Gln Gly Lys Asp Tyr Val Gly Ala Ile Pro
                180                 185                 190
Val Asp Leu Lys Arg Arg Leu Asp Ser Ile Thr Ser Ser Gln Ser Ser
            195                 200                 205
Ala Ser Ser Gly Phe Val Glu Glu Lys Ser Leu Ser Asp Val Glu Glu
```

```
                210                 215                 220
Glu Glu Ala Pro Glu Asp Leu Tyr Lys Asp Phe Leu Thr Leu Glu His
225                 230                 235                 240

Leu Ile Cys Tyr Ser Phe Gln Val Ala Lys Gly Met Glu Phe Leu Ala
                245                 250                 255

Ser Arg Lys Cys Ile His Arg Asp Leu Ala Ala Arg Asn Ile Leu Leu
            260                 265                 270

Ser Glu Lys Asn Val Val Lys Ile Cys Asp Phe Gly Leu Ala Arg Asp
        275                 280                 285

Ile Tyr Lys Asp Pro Asp Tyr Val Arg Lys Gly Asp Ala Arg Leu Pro
    290                 295                 300

Leu Lys Trp Met Ala Pro Glu Thr Ile Phe Asp Arg Val Tyr Thr Ile
305                 310                 315                 320

Gln Ser Asp Val Trp Ser Phe Gly Val Leu Leu Trp Glu Ile Phe Ser
                325                 330                 335

Leu Gly Ala Ser Pro Tyr Pro Gly Val Lys Ile Asp Glu Glu Phe Cys
            340                 345                 350

Arg Arg Leu Lys Glu Gly Thr Arg Met Arg Ala Pro Asp Tyr Thr Thr
        355                 360                 365

Pro Glu Met Tyr Gln Thr Met Leu Asp Cys Trp His Gly Glu Pro Ser
370                 375                 380

Gln Arg Pro Thr Phe Ser Glu Leu Val Glu His Leu Gly Asn Leu Leu
385                 390                 395                 400

Gln Ala Asn Ala Gln Gln Asp Gly Lys Asp Tyr Ile Val Leu Pro Ile
                405                 410                 415

Ser Glu Thr Leu Ser Met Glu Glu Asp Ser Gly Leu Ser Leu Pro Thr
            420                 425                 430

Ser Pro Val Ser Cys Met Glu Glu Glu Val Cys Asp Pro Lys Phe
        435                 440                 445

His Tyr Asp Asn Thr Ala Gly Ile Ser Gln Tyr Leu Gln Asn Ser Lys
    450                 455                 460

Arg Lys Ser Arg Pro Val Ser Val Lys Thr Phe Glu Asp Ile Pro Leu
465                 470                 475                 480

Glu Glu Pro Glu Val Lys Val Ile Pro Asp Asp Asn Gln Thr Asp Ser
                485                 490                 495

Gly Met Val Leu Ala Ser Glu Glu Leu Lys Thr Leu Glu Asp Arg Thr
            500                 505                 510

Lys Leu Ser Pro Ser Phe Gly Gly Met Val Pro Ser Lys Ser Arg Glu
        515                 520                 525

Ser Val Ala Ser Glu Gly Ser Asn Gln Thr Ser Gly Tyr Gln Ser Gly
    530                 535                 540

Tyr His Ser Asp Asp Thr Asp Thr Thr Val Tyr Ser Ser Glu Glu Ala
545                 550                 555                 560

Glu Leu Leu Lys Leu Ile Glu Ile Gly Val Gln Thr Gly Ser Thr Ala
                565                 570                 575

Gln Ile Leu Gln Pro Asp Ser Gly Thr Thr Leu Ser Ser Pro Pro Val
            580                 585                 590

<210> SEQ ID NO 10
<211> LENGTH: 4
<212> TYPE: PRT
<213> ORGANISM: Artficial Sequence
<220> FEATURE:
<223> OTHER INFORMATION: MT-SP1 Cleavage Sequence
<220> FEATURE:
<221> NAME/KEY: Variant
```

```
<222> LOCATION: (1)..(1)
<223> OTHER INFORMATION: Wherein Xaa is Lys or Arg.
<220> FEATURE:
<221> NAME/KEY: Variant
<222> LOCATION: (2)..(2)
<223> OTHER INFORMATION: Wherein Xaa is Gly, Ala, Val, Leu, Ile, Phe,
      Tyr, or Trp.
<220> FEATURE:
<221> NAME/KEY: Variant
<222> LOCATION: (3)..(3)
<223> OTHER INFORMATION: Wherein Xaa iis any amino acid.
<220> FEATURE:
<221> NAME/KEY: Variant
<222> LOCATION: (4)..(4)
<223> OTHER INFORMATION: Wherein Xaa is Lys or Arg.

<400> SEQUENCE: 10

Xaa Xaa Xaa Xaa
1

<210> SEQ ID NO 11
<211> LENGTH: 4
<212> TYPE: PRT
<213> ORGANISM: Artificial Sequence
<220> FEATURE:
<223> OTHER INFORMATION: MT-SP1 Cleavage Sequence
<220> FEATURE:
<221> NAME/KEY: Variant
<222> LOCATION: (1)..(1)
<223> OTHER INFORMATION: Wherein Xaa is Gly, Ala, Val, Leu, Ile, phe,
      Tyr, or Trp.
<220> FEATURE:
<221> NAME/KEY: Variant
<222> LOCATION: (2)..(2)
<223> OTHER INFORMATION: Wherein Xaa is Lys or Arg.
<220> FEATURE:
<221> NAME/KEY: Variant
<222> LOCATION: (3)..(3)
<223> OTHER INFORMATION: Wherein Xaa is any amino acid.
<220> FEATURE:
<221> NAME/KEY: Variant
<222> LOCATION: (4)..(4)
<223> OTHER INFORMATION: Wherein Xaa is Lys or Arg.

<400> SEQUENCE: 11

Xaa Xaa Xaa Xaa
1

<210> SEQ ID NO 12
<211> LENGTH: 4
<212> TYPE: PRT
<213> ORGANISM: Artificial Sequence
<220> FEATURE:
<223> OTHER INFORMATION: MT-SP1 Cleavage Sequence

<400> SEQUENCE: 12

Lys Val Gly Arg
1

<210> SEQ ID NO 13
<211> LENGTH: 4
<212> TYPE: PRT
<213> ORGANISM: Artificial Sequence
<220> FEATURE:
<223> OTHER INFORMATION: MT-SP1 Cleavage Sequence

<400> SEQUENCE: 13

Arg Val Arg Lys
1

<210> SEQ ID NO 14
<211> LENGTH: 4
```

```
<212> TYPE: PRT
<213> ORGANISM: Artificial Sequence
<220> FEATURE:
<223> OTHER INFORMATION: MT-SP1 Cleavage Sequence

<400> SEQUENCE: 14

Arg Arg Val Arg
1

<210> SEQ ID NO 15
<211> LENGTH: 4
<212> TYPE: PRT
<213> ORGANISM: Artificial Sequence
<220> FEATURE:
<223> OTHER INFORMATION: MT-SP1 Cleavage Sequence

<400> SEQUENCE: 15

Arg Lys Thr Lys
1

<210> SEQ ID NO 16
<211> LENGTH: 4
<212> TYPE: PRT
<213> ORGANISM: Artificial Sequence
<220> FEATURE:
<223> OTHER INFORMATION: MT-SP1 Cleavage Sequence

<400> SEQUENCE: 16

Lys Thr Lys Lys
1

<210> SEQ ID NO 17
<211> LENGTH: 4
<212> TYPE: PRT
<213> ORGANISM: Artificial Sequence
<220> FEATURE:
<223> OTHER INFORMATION: MT-SP1 Cleavage Sequence

<400> SEQUENCE: 17

Thr Lys Lys Arg
1

<210> SEQ ID NO 18
<211> LENGTH: 4
<212> TYPE: PRT
<213> ORGANISM: Artificial Sequence
<220> FEATURE:
<223> OTHER INFORMATION: MT-SP1 Activation Site

<400> SEQUENCE: 18

Arg Gln Ala Arg
1

<210> SEQ ID NO 19
<211> LENGTH: 4
<212> TYPE: PRT
<213> ORGANISM: Artificial Sequence
<220> FEATURE:
<223> OTHER INFORMATION: MT-SP1 Cleavage Sequence

<400> SEQUENCE: 19

Lys Glu Asp Glu
1
```

MUTANT MT-SP1 PROTEASES WITH ALTERED SUBSTRATE SPECIFICITY OR ACTIVITY

RELATED APPLICATIONS

Benefit of priority is claimed to U.S. provisional application Ser. No. 60/561,720, filed Apr. 12, 2004, entitled "CLEAVAGE OF VEGF RECEPTOR BY WILDTYPE AND MUTANT MTSP1" to Ruggles et al. The subject matter of this application is incorporated by reference in it entirety.

BACKGROUND OF THE INVENTION

The process of angiogenesis is central to the pathology of conditions including malignancy, diabetic retinopathy and macular degeneration. That cancer is angiogenesis-dependent has been recently supported by experimentation in which striking inhibition of tumor growth can be achieved not by direct treatment of the tumor, but rather by selective inhibition of the endothelial growth factor Vascular Endothelial Growth Factor (VEGF). VEGF is an endothelial cell-specific mitogen normally produced during embryogenesis and adult life. VEGF functions as a significant mediator of angiogenesis in a variety of normal and pathological processes, including tumor development. Tumor vascularization is a vital process for the progression of a tumor to a stage from which it can metastasize. Three high affinity cognate VEGF receptors (VEGFRs) have been identified: VEGFR-1/Flt-1, VEGFR-2/Flk-1/KDR, and VEGFR-3/Flt-4.

VEGFRs are cell surface receptor tyrosine kinases that function as signaling molecules during vascular development. An observation common in pre-clinical studies of anti-angiogenic agents targeting VEGF has been potent and broad-spectrum inhibition of very diverse tumor types (solid tissue and hematological), which is consistent with the widespread dependence of cancer on angiogenesis irrespective of tissue of origin. Single i.v. injections of adenoviruses expressing soluble Flk1 and Flt1 transduce the liver, express high plasma levels, and sequester VEGF from its native receptors on endothelial cells. These circulating VEGF receptors produce systemic inhibition of angiogenesis in corneal micropocket assays, and importantly produce strong and broad-spectrum inhibition of tumor angiogenesis and tumor growth in established lung, prostate, colon, brain and pancreas tumors in subcutaneous, orthotopic and transgenic models. See, e.g. Kuo et al. 2001 PNAS 98: 4605-10. Recently, the efficacy of anti-angiogenic therapy has been demonstrated in a randomized phase III trial using the anti-VEGF monoclonal AVASTIN™ (Genentech) to treat patients with metastatic colon cancer, thus providing proof of principle for this treatment strategy in human neoplasia.

SUMMARY OF THE INVENTION

Nature has engineered the hundreds of proteases in the human genome to exquisite definition so that specificity, inhibition and hydrolysis are perfectly matched to physiological niche. While it has been shown that some proteases are down regulated in cancer, to date no natural proteases are known to function in defending the body from tumorigenesis. However, there are clear applications of proteases programmed to hydrolyze proteins necessary for cancer growth. This invention pairs structure-based protein engineering techniques with positional scanning synthetic combinatorial library (PSSCL) assays to provide novel serine proteases with specificity that, collectively, match the VEGF-R2 stalk over an extended region. PSSCL profiling is a proprietary technology that generates a complete substrate specificity profile or "fingerprint" of each engineered protease in a single assay. With this technology, it is now possible to identify therapeutically relevant proteases that have enhanced specificity toward target substrates and little to no activity towards wild type substrates. In the design process, hundreds of proteases with altered specificity profiles are produced. The technology offers an unprecedented opportunity to study the structural features of specificity. With a screening of proteases with PSSCL, the determinants of serine protease selectivity and catalytic efficiency can be identified. They offer not only an opportunity to discover fundamental rules concerning serine protease function, but also additional information for the design of therapeutically relevant molecules.

The present invention provides compositions and methods for using proteases that cleave proteins known to be involved in disease. In particular, wild type and mutein membrane type serine protease-1 (MT-SP1) polypeptides are provided that cleave VEGF or VEGF receptor, which is known to be involved in angiogenesis. The resultant modified proteins are provided for use as agents for in vivo therapy of cancers and other angiogenesis-related pathologies, including but not limited to macular degeneration, inflammation and diabetes.

The invention also provides methods for the modification of proteases to alter their substrate sequence specificity, so that the modified protease specifically cleaves a VEGF or VEGF receptor protein. Cleavage of targeted VEGF or VEGFRs is provided for treatment of a broad range of cancers wherein the treatment results in reduction or inhibition of vascularization necessary for continued tumor growth. In one embodiment of the invention, this modified protease is a serine protease. In another embodiment of the invention, this modified protease is a mutein MT-SP1.

One embodiment of the invention involves generating a library of protease sequences to be used to screen for modified proteases that cleave VEGF or a VEGFR at a desired substrate sequence. In one aspect of this embodiment, each member of the library is a protease scaffold with at least one mutation made to each different member of the protease library. The remainder of the protease scaffold has the same or a similar sequence to wild-type MT-SP1 protease. The cleavage activity of each member of the protease library is measured using the desired substrate sequence from the VEGF or VEGFR target protein. As a result, proteases with the highest cleavage activity with regard to the desired substrate sequence are detected.

In another aspect of this embodiment, the number of mutations made to the protease scaffold is 1, 2-5 (e.g. 2, 3, 4 or 5), 5-10 (e.g. 5, 6, 7, 8, 9 or 10), or 10-20 (e.g. 10, 11, 12, 13, 14, 15, 16, 17, 18, 19 or 20). In a preferred embodiment, the mutation(s) confer increased substrate specificity. In a specific embodiment, the mutation(s) are positioned in the scaffold in at least one of the S1, S2, S3 and S4 sites. In certain aspects of this embodiment, the activity of the mutein protease is increased by at least 10-fold, 100-fold, or 1000-fold over the activity of the wild type protease. In related aspects, the increase is in substrate specificity.

In another embodiment of the invention, the members of a library are made up of randomized amino acid sequences, and the cleavage activity of each member of the library by the protease is measured. This type of library is referred to herein as a substrate library. Substrate sequences that are cleaved most efficiently by the protease are detected. In specific aspects of this embodiment, the substrate sequence in a substrate library is 4, 5, 6, 7, 8, 9, 10, 11, 12, 13, 14, 15, 16, 17, 18, 19 or 20 amino acids long.

In another embodiment of the invention, the members of the substrate library are made up of randomized amino acid sequences, and the cleavage selectiveness of each member of the library by the protease is measured. Substrate sequences that are cleaved most selectively by the protease are detected. In specific aspects of this embodiment, the substrate sequence in the substrate library is 4, 5, 6, 7, 8, 9, 10, 11, 12, 13, 14, 15, 16, 17, 18, 19 or 20 amino acids long.

In one embodiment of this example, the specificity is measured by observing how many different substrate sequences the protease cleaves at a given activity. Proteases that cleave fewer substrate sequences at a given activity have greater specificity than those that cleave more substrate sequences.

In one aspect of this embodiment, the substrate sequence is a part of VEGF or a VEGFR target protein. In a specific embodiment, the substrate library peptides include the VEGF or VEGFR residues of the P1, P2, P3 and P4 sites. In another aspect of this embodiment, the efficiency of cleavage by the MT-SP1 muteins of the invention of the detected substrate sequence is increased by at least 2-fold, at least 5-fold, at least 10-fold, at least 100-fold, or at least 1000-fold over the cleavage activity of wild-type MT-SP1. In another aspect of this embodiment, the sequence specificity of the MT-SP1 muteins of the invention in cleaving the substrate sequence is increased by at least 2-fold, at least 5-fold, at least 10-fold, at least 100-fold, or at least 1000-fold over the cleavage activity of the MT-SP1 muteins of the invention on other members of the substrate library. Profiling of wild type and mutein target specificity may be done by positional scanning substrate combinatorial libraries (PSSCL), as described in PCT publication WO 01/94332, incorporated herein by reference.

In yet another embodiment, the invention provides a method for treating a patient having a VEGF or VEGFR-related pathology, such as cancer, macular degeneration, inflammation and diabetes. The method involves administering to the patient a protease that cleaves VEGF or a VEGFR protein, so that cleaving the VEGF or VEGFR treats the pathology. In a related embodiment, the treatment of cancer by administration of an engineered protease is in combination with treatment with at least one other anti-cancer agent. In one aspect of this embodiment, the protease is an MT-SP1 mutein. In another aspect of this embodiment, the protease is wild-type MT-SP1.

The patient having a pathology, e.g. the patient treated by the methods of this invention, is a mammal, or more particularly, a human.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, controls. In addition, the materials, methods, and examples are illustrative only and are not intended to be limiting.

Other features and advantages of the invention will be apparent from the following detailed description and claims.

BRIEF DESCRIPTION OF THE DRAWINGS

FIGS. 2B-H are a graphic depiction of PSSCL profiles of MT-SP1 muteins CB18 (FIG. 2B), CB38 (FIG. 2C), CB159 (FIG. 2D), CB83 (FIG. 2E), CB155 (FIG. 2F), CB151 (FIG. 2G), and CB152 (FIG. 2H), showing narrowed specificity profiles. The activity is represented in relative fluorescence units along the y-axis by dividing each amino acid activity by the activity of the best amino acid within each sublibrary.

FIG. 3 is a photograph of a protein gel showing VEGFR2-Fc is efficiently cleaved by wild-type and muteins of MT-SP1.

FIG. 7A is a graphical representation of the amount of proliferation of endothelial cells treated with increased concentrations of MT-SP1 and the muteins CB18, CB83 and CB152. FIG. 7B is a photograph of a western blot showing the cleavage of VEGFR2 in HUVEC cells in the presence of MT-SP1, CB18 and CB83, respectively. FIG. 7C is a graphical representation of the amount of soluble extracellular VEGFR2 released by HUVECs upon treatment with MT-SP1, CB18 and CB83.

FIG. 11 is a photograph of a protein gel showing the cleavage of VEGF by wild-type MT-SP1 but not the selective variant CB 152.

DETAILED DESCRIPTION OF THE INVENTION

Figure 1:
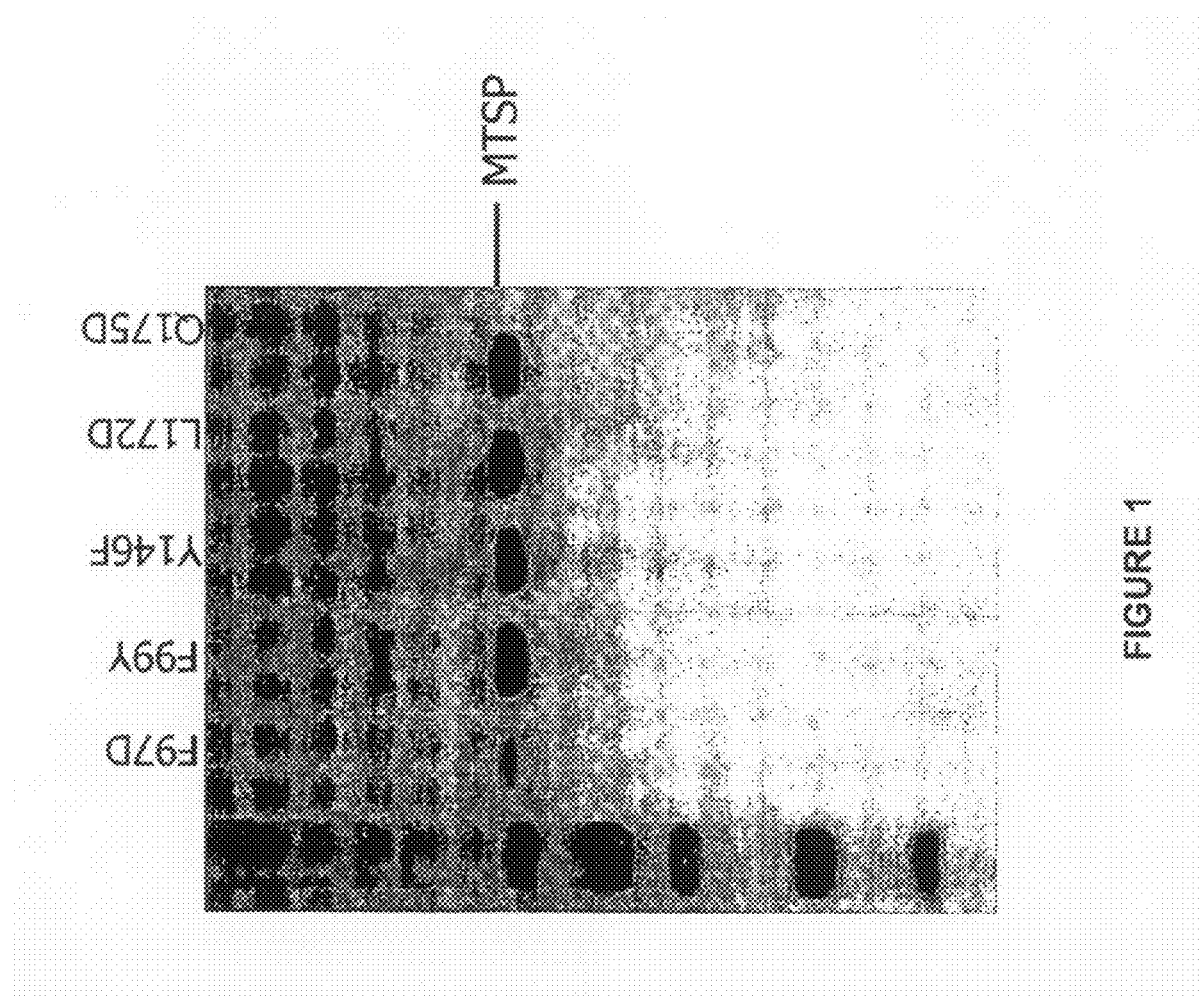
FIG. 1 is a photomicrograph of a SDS PAGE gel showing bands of MT-SP1 purified by a one-column purification procedure and then re-folded through successive dialysis steps. MT-SP1 variants were expressed in bacteria and purified from inclusion bodies. Each protease retains high catalytic activity and is >99% pure, and thus are appropriate for crystallographic studies.

Serine proteases have a highly adaptable protein scaffold. These proteases differ over a broad range in their substrate recognition properties, ranging from highly specific to completely non-specific. Despite these differences in specificity, the catalytic mechanism is well conserved, consisting of a substrate-binding pocket that correctly registers the scissile peptide in the active site. This large family of proteases can be broadly divergent among members in their sequence specificities yet highly conserved in their mechanism of catalysis. This is because substrate specificity is not only determined by local contacts directly between the substrate peptide and the enzyme (first sphere residues), but also by long range factors (second sphere residues). Both first sphere and second sphere substrate binding effects are determined primarily by loops between B-barrel domains. Because these loops are not core elements of the protein, the integrity of the fold is maintained while loop variants with novel substrate specificities can be selected during the course of evolution to fulfill necessary metabolic or regulatory niches at the molecular level.

Laboratory experiments support the theory that the serine proteases are highly adaptable enzymatic scaffolds. For instance, virtually every aspect of subtilisin has been re-engineered, including the enzyme's substrate specificity, thermostability, pH profile, catalytic efficiency, oxidative stability, and catalytic function.

To date, there have been a number of attempts to alter substrate specificity in proteases using structure-guided rational design. One notable example came from the laboratory of Wells and coworkers. See, Ballinger et al., Biochemistry. 1996 Oct. 22; 35 (42): 13579-85. Using subtilisin, an enzyme with low specificity for hydrophobic residues at the P1 position, the authors of this reference managed to alter its specificity for tribasic residues radically by making 3 point mutations in the substrate binding pocket. The resulting mutant had over a 1000-fold specificity for tribasic substrates versus the original hydrophobic substrate. In total, studies on changing the specificity of proteases suggest it is possible to alter substrate specificity radically. This invention discloses specific muteins of the serine protease MT-SP1 having altered target specificity and methods for using them to treat disease.

DEFINITION OF TERMS

Prior to setting forth the invention in detail, certain terms used herein will be defined.

The term "allelic variant" denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term "allelic variant" is also used herein to denote a protein encoded by an allelic variant of a gene.

The term "complements of polynucleotide molecules" denotes polynucleotide molecules having a complementary base sequence and reverse orientation as compared to a reference sequence. For example, the sequence 5' ATGCACGG 3' is complementary to 5' CCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

A "DNA construct" is a single or double stranded, linear or circular DNA molecule that comprises segments of DNA combined and juxtaposed in a manner not found in nature. DNA constructs exist as a result of human manipulation, and include clones and other copies of manipulated molecules.

A "DNA segment" is a portion of a larger DNA molecule having specified attributes. For example, a DNA segment encoding a specified polypeptide is a portion of a longer DNA molecule, such as a plasmid or plasmid fragment, which, when read from the 5' to the 3' direction, encodes the sequence of amino acids of the specified polypeptide.

The term "expression vector" denotes a DNA construct that comprises a segment encoding a polypeptide of interest operably linked to additional segments that provide for its transcription in a host cell. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones, as well as synthetic polynucleotides. Isolated DNA molecules of the present invention may include naturally occurring 5' and 3' untranslated regions such as promoters and terminators. The identification of associated regions will be evident to one of ordinary skill in the art (see for example, Dynan and Tijan, Nature 316:774-78, 1985). When applied to a protein, the term "isolated" indicates that the protein is found in a condition other than its native environment, such as apart from blood and animal tissue. In a preferred form, the isolated protein is substantially free of other proteins, particularly other proteins of animal origin. It is preferred to provide the protein in a highly purified form, i.e., at least 90% pure, preferably greater than 95% pure, more preferably greater than 99% pure.

The term "operably linked", when referring to DNA segments, denotes that the segments are arranged so that they function in concert for their intended purposes, e.g. transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term "nucleotides" is used for both single- and double-stranded molecules where the context permits. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered; thus all nucleotides within a double-stranded polynucleotide molecule may not be paired. Such unpaired ends will, in general, not exceed 20 nt in length.

The term "promoter" denotes a portion of a gene containing DNA sequences that provide for the binding of RNA polymerase and initiation of transcription. Promoter sequences are commonly, but not always, found in the 5' non-coding regions of genes.

A "protease" is an enzyme that cleaves peptide bonds in peptides, polypeptides and proteins. A "protease precursor" or a "zymogen" is a relatively inactive form of the enzyme that commonly becomes activated upon cleavage by another protease.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "substrate sequence" denotes a sequence that is cleaved by a protease.

The term "target protein" denotes a protein that is cleaved at its substrate sequence by a protease.

The term "scaffold" refers to a wild-type or existing variant protease to which various mutations are made. Generally, these mutations change the specificity and activity of the scaffold. One example of an existing variant protease is a protease existing in an organism which has been mutated at one or more positions compared to the wild-type protease amino acid sequence of the species to which the organism belongs.

An "isolated" or "purified" polypeptide or protein or biologically-active portion thereof is substantially free of cellular material or other contaminating proteins from the cell or tissue source from which the protein is derived, or substantially free from chemical precursors or other chemicals when chemically synthesized. The language "substantially free of cellular material" includes preparations of proteins in which the protein is separated from cellular components of the cells from which it is isolated or recombinantly-produced. In one embodiment, the language "substantially free of cellular material" includes preparations of protease proteins having less than about 30% (by dry weight) of non-protease proteins (also referred to herein as a "contaminating protein"), more preferably less than about 20% of non-protease proteins, still more preferably less than about 10% of non-protease proteins, and most preferably less than about 5% of non-protease proteins. When the protease protein or biologically-active portion thereof is recombinantly-produced, it is also preferably substantially free of culture medium, i.e., culture medium represents less than about 20%, more preferably less than about 10%, and most preferably less than about 5% of the volume of the protease protein preparation.

The language "substantially free of chemical precursors or other chemicals" includes preparations of protease proteins in which the protein is separated from chemical precursors or other chemicals that are involved in the synthesis of the protein. In one embodiment, the language "substantially free of chemical precursors or other chemicals" includes preparations of protease proteins having less than about 30% (by dry weight) of chemical precursors or non-protease chemicals, more preferably less than about 20% chemical precursors or non-protease chemicals, still more preferably less than about 10% chemical precursors or non-protease chemicals, and most preferably less than about 5% chemical precursors or non-protease chemicals.

The term "selectiveness" or "specificity" is a ratio of efficiency of cleavage of a targeted substrate site versus another substrate site that is not the targeted site. As a non-limiting example, with MT-SP1, the targeted site is RRVR (SEQ ID NO: 14) and the non-targeted site is RQAR (SEQ ID NO: 18).

The term "peptide" refers to a polypeptide of from 2 to 40 amino acids in length.

Substrate Specificity of Therapeutically Targeted Serine Proteases

Treatment of human disease by therapeutics mostly involves employing small molecules or supplying proteins such as insulin or EPO for specific alterations to cell programs. An important new class of therapeutics being developed is a class of proteases engineered to have a new substrate specificity such that they target disease-related molecules. Methods have now been developed to determine the three dimensional structures of proteases that are specificity-programmed to attack critical cell surface molecules. Structural data on engineered proteases complexed with target-like peptides provide a framework to understand direct and second shell side chain interactions that determine specificity. The correlation of three dimensional structure and protease activity and specificity are of academic and demonstrated long term clinical interest. The invention moves beyond showing the importance of second shell site alterations in the activity of a protease with altered specificity and provides novel MT-SP1 muteins and methods for using them to treat disease. See, e.g., Perona, et al. (1995) Biochemistry 34(5):1489-99.

The invention provides methods of use and methods for designing and testing disease-specific proteases programmed to target proteins critical for maintaining cancer and other diseases. These proteases provide an important new approach to the treatment of cancers, e.g., by impeding tumor growth by blocking tumor angiogenesis, as well as other diseases, including but not limited to macular degeneration, inflammation or diabetes, in which angiogenesis plays a causative or contributive role.

The invention also provides methods of use and methods for designing and testing target-specific proteases programmed to target VEGF and VEGFR which are critical for maintaining cancer and other diseases. These proteases provide an important new approach to the treatment of cancers, e.g., by impeding tumor growth by blocking tumor angiogenesis, as well as other diseases, including but not limited to macular degeneration, inflammation or diabetes, in which angiogenesis plays a causative or contributive role.

The invention also provides methods of use and methods for designing and testing angiogenesis-specific proteases programmed to target proteins critical for modulating apoptosis. These proteases provide an important new approach to the treatment of cancers, e.g., by impeding tumor growth by blocking tumor angiogenesis, as well as other diseases, including but not limited to macular degeneration, inflammation or diabetes, in which angiogenesis plays a causative or contributive role.

Methods are provided for specificity determinants in proteases, thereby allowing design of proteases for disabling proteins critical for maintaining cancer or inflammation or progressing macular degeneration or diabetes. A combination of structure-based mutagenesis and screening are used to design the targeted proteases. Engineering proteases targeted to attack disease-related proteins represents an entirely new sector in the biotechnology industry. Methods are also provided for creating selective proteases as a new therapeutic modality in human disease. Development and proof of concept experiments in animal models of disease provide an understanding of protease substrate selectivity and recognition in this class of enzymes and provide useful information for the dosing and administration of the proteases of the invention for the treatment of human disease.

This disclosure provides protease therapeutic agents, methods for their production and reagents useful therewith. The methods use proteases to address growing health concerns such as cardiovascular disease, inflammatory disorders and cancer.

In one embodiment, the invention characterizes the three-dimensional structures, activity and specificity of serine proteases with novel extended substrate specificity that are targeted to the vascular endothelial growth factor receptor 2 (VEGF-R2). These proteases were developed using protein engineering and selected using unique and powerful protease profiling technology. Built from a MT-SP1 wild-type protease scaffold, they represent a new therapeutic modality in the treatment of cancer.

Signaling by vascular endothelial growth factor (VEGF) and its receptors is implicated in pathological angiogenesis and the rapid development of tumor vasculature in cancer. Drugs that block this signaling pathway prevent the growth and maintenance of tumor blood supply, which leads to the systematic death of the tumor. The recent success of the anti-VEGF antibody AVASTIN™ in patients with metastatic colon cancer has validated VEGF as a target for anti-angiogenic therapy of cancer. Despite these encouraging results, tumor progression has still occurred in anti-VEGF treatment.

The mechanism shows that the AVASTIN™ (bevacizumab) antibody binds VEGF and prevents it from binding to its receptor. Knock-down experiments show that blocking VEGF function blocks angiogenesis. Thus, the inhibition of angiogenic signaling through VEGFR-2 represents an underdeveloped therapeutic area ideal for the development of engineered proteases with novel targeting.

Treatment with a protease that specifically cleaves and inactivates the signaling of the VEGF/VEGFR-2 complex will attenuate the angiogenic signal and create a pool of soluble receptor that lowers free VEGF levels. Variant proteases have an in vitro specificity that recognizes a critical region of the VEGF receptor, which is, in one embodiment, the Flk-1/KDR stalk, over a six amino acid region. Due to their catalytic nature and smaller size, engineered proteases provide a new therapeutic treatment with advantages over competing targeted binding proteins. The advantages are: better tumor penetration, better target saturation, higher effectiveness, and potentially lower dosing. Notably, because they bind, hydrolyze, and release, a single protease could cleave and inactivate hundreds to thousands of substrate VEGF receptors, offering substantial therapeutic amplification. Further, wild-type MT-SP1 also cleaves VEGFR, and is also used according to the invention to cleave VEGFR.

VEGF-R2 and Angiogenic Pathology

Vascular endothelial growth factor (VEGF) is a cytokine that binds and signals through a specific cell surface receptor (VEGFR) to regulate angiogenesis, the process in which new blood vessels are generated from existing vasculature. Pathological angiogenesis describes the increased vascularization associated with disease and includes events such as the growth of solid tumors [McMahon, Oncologist. 2000; 5 Suppl 1:3-10], macular degeneration, and diabetes. In cancer, solid tumors require an ever-increasing blood supply for growth and metastasis. Hypoxia or oncogenic mutation increases the levels of VEGF and VEGFR mRNA in the tumor and surrounding stromal cells leading to the extension of existing vessels and formation of a new vascular network. In wet macular degeneration, abnormal blood vessel growth forms beneath the macula. These vessels leak blood and fluid into the macula damaging photoreceptor cells. In diabetes, a lack of blood to the eyes can also lead to blindness. VEGF stimulation of capillary growth around the eye leads to disordered vessels which do not function properly.

Three tyrosine kinase family receptors of VEGF have been identified (VEGF-R-1/Flt-1, VEGF-R-2/Flk-1/KDR, VEGF-R-3/Flt-4). KDR (the mouse homolog is Flk-1) is a high affinity receptor of VEGF with a $K_d$ of 400-800 pM [Waltenberger, J Biol. Chem. 1994 Oct. 28; 269 (43):26988-95] expressed exclusively on endothelial cells. VEGF and KDR association has been identified as a key endothelial cell-specific signaling pathway required for pathological angiogenesis [Kim, Nature. 1993 Apr. 29; 362 (6423):841-4; Millauer, Nature. 1994 Feb. 10; 367 (6463):576-9; Yoshiji, Hepatology. 1999 November; 30 (5): 1179-86]. Dimerization of the receptor upon ligand binding causes autophosphorylation of the cytoplasmic domains, and recruitment of binding partners that propagate signaling throughout the cytoplasm and into the nucleus to change the cell growth programs. Treatment of tumors with a soluble VEGF-R2 inhibits tumor growth [Lin, Cell Growth Differ. 1998 January; 9 (1):49-58], and chemical inhibition of phosphorylation causes tumors cells to become apoptotic [Shaheen, Cancer Res. 1999 Nov. 1; 59 (21):5412-6].

Therapies targeting the VEGF receptors and Flk-1/KDR specifically have inhibited pathological angiogenesis and shown reduction of tumor size in multiple mouse models of human and mouse solid tumors [Prewett, Cancer Res. 1999 Oct. 15; 59 (20):5209-18; Fong, Neoplasia. 1999 April; 1 (1):31-41. Erratum in: Neoplasia 1999 June; 1 (2): 183] alone and in combination with cytotoxic therapies [Klement, J Clin Invest. 2000 April; 105 (8):R15-24]. Studies with small molecule inhibitors and antibodies validate the VEGF receptor family as a potent anti-angiogenesis target, but more effective therapeutics are still needed.

VEGFR is composed of an extracellular region of seven immunoglobin (Ig)-like domains, a transmembrane region, and two cytoplasmic tyrosine kinase domains. The first three Ig-like domains have been shown to regulate ligand binding, while domains 4 through 7 have a role in inhibiting correct dimerization and signaling in the absence of ligand. As a target for selective proteolysis by engineered proteases, it has the following promising target characteristics:

- a labile region of amino acids accessible to proteolysis;
- high sequence identity between the human, rat and mouse species;
- down regulation of signaling upon cleavage; and
- proteolytic generation of soluble receptors able to non-productively bind ligand.

Several regions of VEGF-R2 are available for specific proteolysis including the stalk region before the transmembrane region and unstructured loops between Ig-like domains.

MT-SP1 Proteases

The present invention provides methods for generating and screening MT-SP1 proteases to cleave target proteins at a given substrate sequence as well as particular muteins and methods for using them to treat disease. Proteases are protein-degrading enzymes that recognize an amino acid or an amino acid substrate sequence within a target protein. Upon recognition of the substrate sequence, proteases catalyze the hydrolysis or cleavage of a peptide bond within a target protein. Such hydrolysis of the target protein can inactivate it, depending on the location of peptide bond within the context of the full-length sequence of the target sequence. The specificity of MT-SP1 proteases can be altered through protein engineering. If a protease is engineered to recognize a substrate sequence within a target protein or proteins (i) that would alter the function i.e. by inactivation of the target protein(s) upon catalysis of peptide bond hydrolysis, and (ii) the target protein(s) is a point of molecular intervention for a particular disease or diseases, then the engineered protease has a therapeutic effect via a proteolysis-mediated inactivation event. In particular, MT-SP1 proteases can be engineered to cleave specific target receptors between their transmembrane and cytokine or growth factor binding domains. The stalk regions that function to tether protein receptors to the surface of a cell or loop regions are thereby disconnected from the globular domains in a polypeptide chain.

In one embodiment, the target protein to be cleaved by MT-SP1 proteases is involved with a pathology, where cleaving the target protein at a given substrate sequence serves as a treatment for the pathology.

The protease cleaves cell surface molecules that are responsible for modulation of angiogenesis. Where the cell surface molecule is a VEGFR signaling in tumor angiogenesis, cleavage prevents the spread of cancer. For example, cleavage of a cell surface domain from a VEGFR molecule can inactivate its ability to transmit extracellular signals, especially cell proliferation signals. Without angiogenesis to feed the tumor, cancer cells often cannot proliferate. In one embodiment, a MT-SP1 protease of the invention is therefore used to treat cancer. Also, cleavage of VEGFR can be used to modulate angiogenesis in other pathologies, such as macular degeneration, inflammation and diabetes. In one embodiment, cleaving a target VEGFR protein involved in cell cycle progression inactivates the ability of the protein to allow the cell cycle to go forward. Without the progression of the cell cycle, cancer cells cannot proliferate. Therefore, the MT-SP1 proteases of the invention which cleave VEGF or VEGFR are useful in the treatment of cancer and other cell cycle dependent pathologies.

The protease also cleaves soluble proteins that are responsible for tumorigenicity. Cleaving VEGF prevents signaling through the VEGF receptor and decreases angiogenesis, thus decreasing disease in which angiogenesis plays a role, such as cancer, macular degeneration, inflammation and diabetes. Further, VEGF signaling is responsible for the modulation of the cell cycle in certain cell types. Therefore, the MT-SP1 proteases of the invention which cleave VEGF are useful in the treatment of cancer and other cell cycle dependent pathologies.

In some embodiments, the engineered MT-SP1 protease is designed to cleave one or more of the target proteins in Table 1, thereby inactivating the activity of the protein. The MT-SP1 protease can be used to treat a pathology associated with that protein, by inactivating it.

TABLE 1

Protease Targets

| Target | Indication | Molecule class |
|---|---|---|
| VEGF | Cancer | Cytokine |
| VEGFR-1/Flt-1 | Cancer | Receptor |
| VEGFR-2/KDR | Cancer | Receptor |
| VEGFR-3/Flt-4 | Cancer | Receptor |

The protease scaffold is the MT-SP1 protein disclosed below in Table 2.

TABLE 2

Protease Scaffolds

| Code | Name | Gene | Link | Locus |
|---|---|---|---|---|
| S01.087 | membrane-type serine protease | MT-SP1 | 84000 | 11q23 |

The wild type MT-SP1 polypeptide of SEQ ID NO:1 is provided in Table 3, and is designated as TADG-15.

TABLE 3

Wild-type MT-SP1 polypeptide (SEQ ID NO: 1)

```
              1                                              50
TADG-15  MGSDRARKGG GGPKDFGAGL KYNSRHEK-               (SEQ ID NO: 1)
         VN GLEEGVEFLP VNNVKKVEKH 51                                             100
TADG-15  GPGRWVVLAA VLIGLLLVLL GIG-
         FLVWHLQ YRDVRVQKVF NGYMRITNEN 101                                            150
TADG-15  FVDAYENSNS TEFVS-
         LASKV KDALKLLYSG VPFLGPYHKE SAVTAFSEGS 151                                            200
TADG-15  VIAYYWSEFS IPQHLVEEAE RVMAEERV-
         VM LPPRARSLKS FVVTSVVAFP 201                                            250
TADG-15  TDSKTVQRTQ DNSCSFGLHA RGVELMR-
         FTT PGFPDSPYPA HARCQWALRG 251                                            300
TADG-15  DADSVLSLTF RSFDLASCDE RGS-
         DLVTVYN TLSPMEPHAL VQLCGTYPPS 301                                            350
TADG-15  YNLTFHSSQN VLLITLITNT ERRHPG-
         FEAT FFQLPRMSSC GGRLRKAQGT 351                                            400
TADG-15  FNSPYYPGHY PPNIDCTWNI EVPNNQH-
         VKV SFKFFYLLEP GVPAGTCPKD 401                                            450
TADG-15  YVEINGEKYC GERSQFVVTS NSNKITVR-
         FH SDQSYTDTGF LAEYLSYDSS 451                                            500
TADG-15  DPCPGQFTCR TGRCIRKELR CDGWADCT-
         DH SDELNCSCDA GHQFTCKNKF 501                                            550
TADG-15  CKPLFWVCDS VNDCGDNSDE QGCSC-
         PAQTF RCSNGKCLSK SQQCNGKDDC
```

TABLE 3-continued

| Wild-type MT-SP1 polypeptide (SEQ ID NO: 1) | |
|---|---|
| 551 | 600 |
| TADG-15 GDGSDEASCP KVNVVTCTKH TYR-CLNGLCL SKGNPECDGK EDCSDGSDEK | |
| 601 | 650 |
| TADG-15 DCDCGLRSFT RQARVVGGTD ADEGEWP-WQV SLHALGQGHI CGASLISPNW | |
| 651 | 700 |
| TADG-15 LVSAAHCYID DRGFRYSDPT QWTAFLGL-HD QSQRSAPGVQ ERRLKRIISH | |
| 701 | 750 |
| TADG-15 PFFNDFTFDY DIALLELEKP AEYSSM-VRPI CLPDASHVFP AGKAIWVTGW | |
| 751 | 800 |
| TADG-15 GHTQYGGTGA LILQKGEIRV INQTTCEN-LL PQQITPRMNC VGFLSGGVDS | |
| 801 | 850 |
| TADG-15 CQGDSGGPLS SVEADGRIFQ AGV-VSWGDGC AQRNKPGVYT RLPLFRDWIK | |
| TADG-15 ENTGV | |

A ClustalW alignment is provided in Table 4, comparing the wild type MT-SP1 polypeptide of SEQ ID NO:1, designated as TADG-15, to the MT-SP1 protease domain of SEQ ID NO:2. MT-SP1 protease domain residues targeted for mutagenesis are shown in bold. The MT-SP1 protease domain is composed of a pro-region and a catalytic domain. The catalytically activity portion of the sequence begins after the autoactivation site: RQAR (SEQ ID NO: 18) with the sequence VVGG (SEQ ID NO: 6) (underlined).

TABLE 4

ClustalW of MT-SP1 Protease Domain

```
PileUp
   MSF: 855   Type: P    Check: 4738  ..
 Name: MTSP_protease_domain   Len: 855    Check: 8683   Weight: 0
 Name: TADG-15      Len: 855    Check: 6055   Weight: 0
//
               1                                                50
MTSP_protease_domain.......... ..........  ..........  ..........  ..........(SEQ ID NO: 2)
            TADG-15MGSDRARKGG GGPKDFGAGL KYNSRHEK-        (SEQ ID NO: 1)
                   VN GLEEGVEFLP VNNVKKVEKH 51                                               100
MTSP_protease_domain.......... ..........  ..........  ..........  ..........
            TADG-15GPGRWVVLAA VLIGLLLVLL GIG-
                   FLVWHLQ YRDVRVQKVF NGYMRITNEN 101                                               150
MTSP_protease_domain.......... ..........  ..........  ..........  ..........
            TADG-15FVDAYENSNS TEFVS-
                   LASKV KDALKLLYSG VPFLGPYHKE SAVTAFSEGS 151                                               200
MTSP_protease_domain.......... ..........  ..........  ..........  ..........
            TADG-15VIAYYWSEFS IPQHLVEEAE RVMAEERV-
                   VM LPPRARSLKS FVVTSVVAFP 201                                               250
MTSP_protease_domain.......... ..........  ..........  ..........  ..........
            TADG-15TDSKTVQRTQ DNSCSFGLHA RGVELMR-
                   FIT PGFPDSPYPA HARCQWALRG 251                                               300
MTSP_protease_domain.......... ..........  ..........  ..........  ..........
            TADG-15DADSVLSLTF RSFDLASCDE RGS-
                   DLVTVYN TLSPMEPHAL VQLCGTYPPS 301                                               350
MTSP_protease_domain.......... ..........  ..........  ..........  ..........
            TADG-15YNLTFHSSQN VLLITLITNT ERRHPG-
                   FEAT FFQLPRMSSC GGRLRKAQGT
```

TABLE 4-continued

ClustalW of MT-SP1 Protease Domain

```
              351                                                  400
MTSP_protease_domain..........  ..........  ..........  ..........  ..........
             TADG-15FNSPYYPGHY PPNIDCTWNI EVPNNQH-
                    VKV SFKFFYLLEP GVPAGTCPKD 401                                                  450
MTSP_protease_domain..........  ..........  ..........  ..........  ..........
             TADG-15YVEINGEKYC GERSQFVVTS NSNKITVR-
                    FH SDQSYTDTGF LAEYLSYDSS 451                                                  500
MTSP_protease_domain..........  ..........  ..........  ..........  ..........
             TADG-15DPCPGQFTCR TGRCIRKELR CDGWADCT-
                    DH SDELNCSCDA GHQFTCKNKF 501                                                  550
MTSP_protease_domain..........  ..........  ..........  ..........  ..........
             TADG-15CKPLFWVCDS VNDCGDNSDE QGCSC-
                    PAQTF RCSNGKCLSK SQQCNGKDDC 551                                                  600
MTSP_protease_domain..........  ..........  ..........  ..........  .......DEK
             TADG-15GDGSDEASCP KVNVVTCTKH TYR-
                    CLNGLCL SKGNPECDGK EDCSDGSDEK 601                                                  650
MTSP_protease_domainDCDCGLRSFT RQARVVGGTD ADEGEWP-
                    WQV SLHALGQGHI CGASLISPNW
             TADG-15DCDCGLRSFT RQAR
                    VVGGTD ADEGEWPWQV SLHALGQGHI CGASLISPNW 651                                                  700
MTSP_protease_domainLVSAAHCYID DRGFRYSDPT QWTAFLGL-
                    HD QSQRSAPGVQ ERRLKRIISH
             TADG-15LVSAAHCYID DRGFRYSDPT QWTAFLGL-
                    HD QSQRSAPGVQ ERRLKRIISH 701                                                  750
MTSP_protease_domainPFFNDFTFDY DIALLELEKP AEYSSM-
                    VRPI CLPDASHVFP AGKAIWVTGW
             TADG-15PFFNDFTFDY DIALLELEKP AEYSSM-
                    VRPI CLPDASHVFP AGKAIWVTGW 751                                                  800
MTSP_protease_domainGHTQYGGTGA LILQKGEIRV INQTTCEN-
                    LL PQQITPRMMC VGFLSGGVDS
             TADG-15GHTQYGGTGA LILQKGEIRV INQTTCEN-
                    LL PQQITPRMMC VGFLSGGVDS 801                                                  850
MTSP_protease_domainCQGDSGGPLS SVEADGRIFQ AGV-
                    VSWGDGC AQRNKPGVYT RLPLFRDWIK
             TADG-15CQGDSGGPLS SVEADGRIFQ AGV-
                    VSWGDGC AQRNKPGVYT RLPLFRDWIK 851
MTSP_protease_domainENTGV
             TADG-15ENTGV
```

A ClustalW alignment is provided in Table 5, comparing the wild type MT-SP1 protease domain of SEQ ID NO:2 with human chymotrypsin. MT-SP1 protease domain residues targeted form mutagenesis are numbered according to chymotrypsin.

TABLE 5

ClustalW alignment of human chymotrypsin and MT-SP1 protease domains

```
                     16          30 31           45 46           60 61          66
Chymotrypsin B       IVNGEDAVPGSWPWQ VSLQDKTGFHFCGGS LISEDWVVTAAHCGV ---------RTS- (SEQ ID NO: 3)
                     DVV
MTSP_protease_domainVVGGTDADEGEWPWQ VSLHALGQGHIC-                              (SEQ ID NO: 2)
                    GAS LISPNWLVSAAHCYI DDRGFRYSDPTQWTA
```

TABLE 5-continued

ClustalW alignment of human chymotrypsin and MT-SP1 protease domains

|  | 67 | 80 | 81 | 95 | 96 | 110 | 111 | 125 |
|---|---|---|---|---|---|---|---|---|
| Chymotrypsin B | VAGEFDQGS-DEENI QVLKIAKVFKNPKF-S ILTVNNDITLLKLAT PARFSQTVSAVCLPS | | | | | | | |
| MTSP_protease_domain | FLGLHDQSQRSAPGV QERRLKRIISH-PFFN DFTFDYDIALLELEK PAEYSSMVRPICLPD | | | | | | | |

|  | 126 | 140 | 141 | 155 | 156 | 170 | 171 | 184 |
|---|---|---|---|---|---|---|---|---|
| Chymotrypsin B | ADDDFPAGTLCATTG WGKTKYNANKTPD-KL QQAALPLLSNAECKK SWGRRITDVMICAG- | | | | | | | |
| MTSP_protease_domain | ASHVFPAGKAIWVTG WGHTQYGG-TGALIL QKGEIRVINQTTCEN LLPQQIT-PRMMCVGF | | | | | | | |

|  | 185 | 198 | 199 | 212 | 213 | 226 | 227 | 240 |
|---|---|---|---|---|---|---|---|---|
| Chymotrypsin B | -ASGVSSCMGDSGGP L-VCQKDGAWTLVGI VSWGSDTCSTSS-PG VYARVTKLIP-WVQKI | | | | | | | |
| MTSP_protease_domain | LSGGVDSCQGDSGGP LSSVEADGRIFQAGV VSWGDG-CAQRNKPG VYTRLPLFRD-WIKEN | | | | | | | |

|  | 241 |
|---|---|
| Chymotrypsin B | LAAN |
| MTSP_protease_domina | TGV- |

A DNA sequence is provided in Table 6 which encodes the catalytic domain (SEQ ID NO:2) of wild type MT-SP1 protease domain as contained within the pQE cloning vector.

TABLE 6

The DNA sequence of the catalytic domain of wild type MT-SP1.

(SEQ ID NO: 4)
```
gtt gtt ggg ggc acg gat gcg gat-
 gag ggc gag tgg ccc tgg cag gta agc ctg cat gct ctg ggc cag ggc cac atc tgc ggt gct-
 tcc ctc atc tct ccc aac tgg ctg gtc tct gcc gca cac tgc tac atc gat gac aga gga t-
tc agg tac tca gac ccc acg cag tgg acg gcc ttc ctg ggc ttg cac gac cag agc-
 cag cgc agc gcc cct ggg gtg cag gag cgc agg ctc aag cgc atc atc tcc cac ccc ttc t-
tc aat gac ttc acc ttc gac tat gac atc gcg ctg ctg gag ctg gag aaa ccg gca gag ta-
c agc tcc atg gtg cgg ccc atc tgc ctg ccg gac gcc tcc cat gtc ttc cct gcc ggc aag-
 gcc atc tgg gtc acg ggc tgg gga cac acc cag tat gga ggc act ggc gcg ctg atc ctg-
 caa aag ggt gag atc cgc gtc atc aac cag acc acc tgc gag aac ctc ctg ccg cag ca-
g atc acg ccg cgc atg atg tgc gtg ggc ttc ctc agc ggc ggc gtg gac tcc tgc cag ggt-
 gat tcc ggg gga ccc ctg tcc agc gtg gag gcg gat ggg cgg atc ttc cag gcc ggt gtg-
 gtg agc tgg gga gac ggc tgc gct cag agg aac aag cca ggc gtg tac aca agg ctc-
 cct ctg ttt cgg gac tgg atc aaa gag aac act ggg gta tag
```

Engineering MT-SP1 Muteins

Virtually every aspect of a protease, including MT-SP1, can be re-engineered, including the enzyme substrate sequence specificity, thermostability, pH profile, catalytic efficiency, oxidative stability, and catalytic function.

Wild-type MT-SP1 protease is used in accordance with the methods of the invention as a scaffold for incorporating various mutations that change its substrate specificity. Among the determinants of substrate sequence specificity in serine proteases come from the S1-S4 positions in the active site, where the protease is in contact with the P1-P4 residues of the peptide substrate sequence. In some cases, there is little (if any) interaction between the S1-S4 pockets of the active site, such that each pocket appears to recognize and bind the corresponding residue on the peptide substrate sequence independent of the other pockets. Thus, the specificity determinants may be generally changed in one pocket without affecting the specificity of the other pockets.

For example, a MT-SP1 protease with low specificity for a residue at a particular binding site or for a particular sequence is altered in its specificity by making point mutations in the substrate sequence binding pocket. In some cases, the resulting MT-SP1 mutein has a greater than 2-fold increase in specificity at a site or for a particular sequence than does wild-type. In another embodiment, the resulting MT-SP1 mutein has a greater than 5-fold increase in specificity at a site or for a particular sequence than does wild-type. In another embodiment, the resulting MT-SP1 mutein has a greater than 10-fold increase in specificity at a site or for a particular sequence than does wild-type. In another embodiment, the resulting MT-SP1 mutein has a greater than 100-fold increase in specificity at a site or for a particular sequence than does wild-type. In another embodiment, the resulting MT-SP1 mutein has an over 1000-fold increase in specificity at a site or for a particular sequence than does wild-type.

One embodiment of this example, the specificity is measured by observing how many disparate substrate sequences a mutein protease cleaves at a given activity as compared to the number in the wild-type protease. If the mutein protease cleaves fewer substrate sequences than the wild-type, then the mutein protease has greater specificity than the wild-type. A mutein that has 10 fold higher specificity than a wild-type protease cleaves 10 fold fewer substrate sequences than the wild-type protease.

Also contemplated by the invention are libraries of MT-SP1 scaffolds with various mutations that are generated and screened using methods known in the art and those detailed herein. Libraries are screened to ascertain the substrate sequence specificity of the members. Libraries of MT-SP1 scaffolds are tested for specificity by exposing the members to substrate peptide sequences. The MT-SP1 member with the mutations that allow it to cleave the substrate sequence is identified. The MT-S P1 scaffold library is constructed with enough variety of mutation in the scaffold such that a variety of substrate peptide sequences are cleaved by various members of the MT-SP1 scaffold library. Thus, proteases specific for any target protein can be generated.

Particular protease residues that, upon mutation, affect the activity and specificity of MT-SP1 scaffold protease are described here. MT-SP1 is a serine protease. The serine proteases are members of the same family as chymotrypsin. In one embodiment of the invention, MT-SP1 muteins with altered specificity are generated by a structure-based design approach. Each protease has a series of amino acids that lines the active site pocket and makes direct contact with the substrate. Throughout the chymotrypsin family, the backbone interaction between the substrate and enzyme is completely conserved, but the side chain interactions vary considerably. The identity of the amino acids that comprise the S1-S4 pockets of the active site determines the substrate specificity of that particular pocket. Grafting the amino acids of one serine protease to another of the same fold modifies the specificity of one to the other. Scaffold residues of serine proteases are identified using chymotrypsin numbering. For example, a mutation at position 99 in the S2 pocket to a smaller amino acid confers a preference for larger hydrophobic residues in the P2 substrate position. Using this process of selective mutagenesis, followed by substrate library screening, one can generate and identify proteases with novel substrate specificities towards proteins involved with various diseases.

The amino acids of the protease that comprise the S1-S4 pockets are those that have side chains within 4 to 5 angstroms of the substrate. The interactions these amino acids have with the protease substrate are generally called "first shell" interactions because they directly contact the substrate. There are also "second shell" and "third shell" interactions that ultimately position the first shell amino acids. The invention also contemplates the mutation of those amino actions which undergo second and third shell interactions in order to change the specificity and rate of reaction of the mutein protease of the invention.

Chymotrypsin family members share sequence and structural homology with chymotrypsin. Based on chymotrypsin numbering, the active site residues are Asp102, His57, and Ser 195. The linear amino acid sequence can be aligned with that of chymotrypsin and numbered according to the β sheets of chymotrypsin. Insertions and deletions occur in the loops between the beta sheets, but throughout the structural family, the core sheets are conserved. The serine proteases interact with a substrate in a conserved β sheet manner. Up to 6 conserved hydrogen bonds can occur between the substrate and the enzyme. All serine proteases of the chymotrypsin family have a conserved region at their N-terminus that is necessary for catalytic activity. It is generally IIGG, VVGG or IVGG (SEQ ID NOS: 5, 6 and 7, respectively). Where the first amino acid in this quartet is numbered according to the chymotrypsin numbering, it is given the designation of Ile16. This numbering does not reflect the length of the precursor region. Also, in one embodiment, the muteins described herein are on the rat MT-SP1 scaffold. In another embodiment, the muteins described herein are on the human scaffold. The chymotrypsin numbering and residues referred to herein apply to the rat and human MT-SP1 scaffold. Both human and rat muteins can be made using the expression systems of the invention. MT-SP1 scaffolds isolated or cloned from other species are also encompassed within this invention.

MT-SP1 Structural Determinants

Serine protease substrate recognition sites are labeled according to the method of Schecter and Berger Biochem. Biophys. Res. Commun. 27 (1967) 157-162. Labels increase in number from P1, P2, . . . Pn for the substrate amino acids N-terminal to the scissile bond and P1', P2', . . . Pn' for the substrate amino acids C-terminal to the scissile bond. The corresponding substrate recognition pockets on the enzyme are labeled, Sn . . . S2, S1, S1', S2' . . . Sn'. Thus, P2 interacts with S2, P1 with S1, P1' with S1', etc. Amino acids in the MT-SP1 scaffold are numbered according to their alignment with the serine protease chymotrypsin. See, Blow, D. M. (1976) *Acc. Chem. Res.* 9, 145-152.

For serine proteases, the following amino acids in the primary sequence are determinants of specificity: 195, 102, 57 (the catalytic triad); 189, 190, 191, 192, and 226 (P1); 57, the loop between 58 and 64, and 99 (P2); 192, 217, 218 (P3), the loop between Cys168 and Cys182, 215 and 97 to 100 (P4). Position 189 in a serine protease is a residue buried at the bottom of the pocket that determines the P1 specificity. To make a variant protease with an altered substrate recognition profile, the amino acids in the three-dimensional structure that contribute to the substrate selectivity (specificity determinants) are targeted for mutagenesis. For the serine proteases, numerous structures of family members have defined the surface residues that contribute to extended substrate specificity (Wang et al., Biochemistry 2001 Aug. 28; 40 (34): 10038-46; Hopfner et al., Structure Fold Des. 1999 Aug. 15; 7 (8):989-96; Friedrich et al. J Biol. Chem. 2002 Jan. 18; 277 (3):2160-8; Waugh et al., Nat Struct Biol. 2000 September; 7 (9):762-5).

Structural determinants for MT-SP1 are listed in Table 7 following the numbering of chymotrypsin. The number underneath the Cys168-Cys182 and 60's loop column headings indicate the number of amino acids in the loop between the two amino acids. The yes/no designation under the Cys191-Cys220 column heading indicates whether the disulfide bridge is present in this protease. These regions are variable within the family of chymotrypsin-like serine proteases and represent structural determinants in themselves.

known in the art for site specific amino acid mutation of MT-SP1 could be used to prepare a set of MT-SP1 muteins of the invention that can be screened to identify muteins that cleave VEGF, a VEGFR, or another target protein.

MT-SP1 is a mosaic protein containing a transmembrane domain, two CUB domains, four LDLR repeats, and a serine protease domain. The protease domain of MT-SP1 has been expressed in bacteria or yeast in milligram quantities and purified. Profiling by positional scanning substrate combinatorial libraries (PSSCL) revealed that it has trypsin-like activity, demonstrating a strong preference for basic residues at the P1 position. The extended P2-P4 specificity of MT-SP1 is shown in Table 9.

TABLE 7

Structural determinants for MT-SP1.
Scaffold Residues that Determine Specificity

| | S4 | | | | | S3 | | | S2 60's loop | | S1 | | | Cys$^{220}$ |
|---|---|---|---|---|---|---|---|---|---|---|---|---|---|---|
| | 171 | 174 | 180 | 215 | Cys$^{182}$ | 192 | 218 | 99 | 57 | (58–64) | 189 | 190 | 226 | |
| MT-SP1 | Leu | Gln | Met | Trp | 13 | Gln | Asp | Phe | His | 16 | Asp | Ser | Gly | yes |

(S2 spans 60's loop area between Cys$^{168}$ and Cys$^{191}$.)

The positional scanning synthetic combinatorial library (PSSCL) results for the P1 through P4 substrate positions of MT-SP1, chymotrypsin, trypsin and thrombin are provided in Table 8. In Table 8, "Hyd" represents any hydrophobic amino acid (i.e. glycine, alanine, valine, leucine, isoleucine, phenylalanine, tyrosine, or tryptophan). "Xxx" represents any amino acid.

TABLE 8

Substrate specificities for MT-SP1 and related proteases.
Substrate Specificity

| | P4 | P3 | P2 | P1 |
|---|---|---|---|---|
| MT-SP1 | Arg | Hyd | Ser | Arg |
| | Hyd | Arg | Thr | Lys |
| Chymotrypsin | Xxx | Xxx | Val | Phe |
| | | | Pro | Val |
| Trypsin | Xxx | Xxx | Ala | Arg |
| | | | Ser | Lys |
| Thrombin | Phe | Xxx | Pro | Arg |
| | Leu | | | Lys |

TABLE 9

Extended P2–P4 Specificity of Wild Type MT-SP1

| P4 | P3 | P2 | P1 | |
|---|---|---|---|---|
| Arg/Lys | Xxx | Xxx | Arg/Lys | or |
| Xxx | Arg/Lys | Xxx | Arg/Lys | | wherein Xxx is any amino acid.

Thus MT-SP1 appears to have a specificity switch, wherein it accepts a positively charged residue in the P4 position or a positively charged residue in the P3 position. The crystal structure of the protease domain of MT-SP1 has been solved, providing a structural rationale for its substrate specificity profile.

To develop novel muteins useful for attenuating VEGF signaling for anti-angiogenesis therapy, MT-SP1 polypeptides are engineered to cleave and inactivate VEGF receptor 2 (KDR) selectively. Wildtype MT-SP1 protease domain (herein referred to as MT-SP1) and mutants thereof are cloned, expressed, purified, and profiled by PSSCL. See, PCT publication WO 01/94332, incorporated by reference herein in its entirety. Wildtype and mutant MT-SP1 are then assayed for the cleavage of purified VEGF receptor, as further described and illustrated in the Examples below.

MT-SP1 variants that are able to cleave the purified VEGF receptor are assayed for the cleavage of the receptor on endothelial cells, wherein cleavage results in abrogation of cell proliferation resulting from VEGF signaling. See, e.g. Yilmaz et al., 2003 Biochem. Biophys. Res. Commun. 306 (3): 730-736; Gerber et al., 1998 J Biol Chem. 273 (46): 30336-43. Promising variants are then tested in animal models angiogenesis and tumor growth, including the mouse micropocket corneal assay and tumor xenografts. See, e.g. Kuo et al., PNAS, 2001, 98:4605-4610.

Mutants of MT-SP1 were made by QuikChange PCR (Stratagene) according to the manufacturer's protocol. A non-limiting listing of a variety of resulting mutant MT-SP1

MT-SP1 Mutein Constructs

To change the substrate preference of a given subsite (S1-S4) for a given amino acid, the specificity determinants that line the binding pocket are mutated, either individually or in combination. The resulting set of protease muteins, each different member having a different specificity and one or more differing mutations from one another, and the coding sequences and expression vectors producing them, constitute important aspects of the present invention. In one embodiment of the invention, a saturation mutagenesis technique is used in which the residue(s) lining the pocket is mutated to each of the 20 possible amino acids. This can be accomplished using the Kunkle method (In: Current Protocols in Molecular Biology, Ausubel et al. (eds.) John Wiley and Sons, Inc., Media Pa.). Briefly, a mutagenic oligonucleotide primer is synthesized that contains either NNS or NNK-randomization at the desired codon. The primer is annealed to the single stranded DNA template, and DNA polymerase is added to synthesize the complementary strain of the template. After ligation, the double stranded DNA template is transformed into *E. coli* for amplification. Alternatively, single amino acid changes are made using standard, commercially available site-directed mutagenesis kits such as QuikChange (Stratagene). In another embodiment, any method commonly polypeptides (muteins) is provided in Table 10, and their corresponding CB numbers are provided in Table 11. The MT-SP1 wild-type residues, identified using chymotrypsin numbering, are provided in the left column, and the MT-SP1 mutants are provided in the right column. Asp60b and Arg60c are part of an insertion in MTSP not present in chymotrypsin. Therefore, all the residues in this loop are assigned to residue 60 with chymotrypsin numbering.

TABLE 10

MT-SP1 mutein constructs

| wild type MT-SP1 residue (chymotrypsin numbering) | Replacement Mutein residue |
|---|---|
| Asp60b | Ala, Arg, Ile, Phe |
| Arg60c | Ala, Asp, Ile, Phe, Trp |
| Phe97 | Ala, Arg, Asn, Asp, Glu, Trp |
| Phe99 | Ala, Arg, Asn, Asp, Glu, Tyr, Trp, Val |
| Tyr146 | Ala, Arg, Asn, Asp, Glu, Phe, Trp |
| Leu172 | Ala, Arg, Asn, Asp, Glu, Phe |
| Gln175 | Ala, Arg, Asp, Glu, Phe, Val |
| Met180 | Ala, Arg, Glu, Tyr |
| Gln192 | Ala, Arg, Asp, Phe, Val |
| Trp215 | Arg, Asp, Ile, Phe, Tyr |
| Asp217 | Ala, Arg, Glu, Phe, Val |
| Lys224 | Ala, Asp, Phe, Val |

TABLE 11

MT-SP1 muteins labeled by CB number

| CB0011 | F97N |
| CB0012 | F97D |
| CB0013 | F97E |
| CB0014 | F99Y |
| CB0015 | F99W |
| CB0016 | Y146F |
| CB0017 | L172N |
| CB0018 | L172D |
| CB0019 | L172E |
| CB0020 | Q175D |
| CB0021 | Q175E |
| CB0022 | D217A |
| CB0023 | D217V |
| CB0024 | D217F |
| CB0031 | F97A |
| CB0032 | F97W |
| CB0033 | F97R |
| CB0034 | F99N |
| CB0035 | F99D |
| CB0036 | F99E |
| CB0037 | F99A |
| CB0038 | F99V |
| CB0039 | F99R |
| CB0040 | Y146N |
| CB0041 | Y146D |
| CB0042 | Y146E |
| CB0043 | Y146A |
| CB0044 | Y146W |
| CB0045 | Y146R |
| CB0046 | L172A |
| CB0047 | L172V |
| CB0048 | L172F |
| CB0049 | L172R |
| CB0050 | Q175A |
| CB0051 | Q175V |
| CB0052 | Q175F |
| CB0053 | Q175R |
| CB0054 | D217E |
| CB0055 | D217R |
| CB0056 | W215F |
| CB0057 | W215Y |
| CB0058 | W215I |
| CB0059 | W215D |
| CB0060 | W215R |

TABLE 11-continued

MT-SP1 muteins labeled by CB number

| CB0061 | Q192A |
| CB0062 | Q192V |
| CB0063 | Q192D |
| CB0064 | Q192R |
| CB0065 | Q192F |
| CB0066 | K224A |
| CB0067 | K224F |
| CB0068 | K224V |
| CB0069 | K224D |
| CB0070 | M180E |
| CB0071 | M180Y |
| CB0072 | M180R |
| CB0073 | M180A |
| CB0074 | D60bI |
| CB0075 | D60bF |
| CB0076 | D60bR |
| CB0077 | D60bA |
| CB0078 | R60cI |
| CB0079 | R60cF |
| CB0080 | R60cD |
| CB0081 | R60cA |
| CB0082 | R60cW |
| CB0083 | L172D/Q175D |
| CB0150 | F99V/L172D |
| CB0151 | F99V/L172D/Q175D |
| CB0152 | F99V/K224F |
| CB0153 | F99V/M180E |
| CB0154 | F99V/Y146D |
| CB0155 | Y146D/K224F |
| CB0156 | Y146D/M180E |
| CB0157 | Y146D/L172D/Q175D |
| CB0158 | F99V/Y146D/L172D/Q175D |
| CB0159 | F99I/L172D/Q175D |
| CB0160 | F99L/L172D/Q175D |
| CB0161 | F99T/L172D/Q175D |
| CB0162 | F99A/L172D/Q175D |
| CB0173 | F99I/K224F |
| CB0174 | F99L/K224F |
| CB0175 | F99T/K224F |
| CB0176 | F99V/Y146D/K224F |
| CB0177 | F99I/Y146D/K224F |
| CB0178 | F99L/Y146D/K224F |
| CB0179 | F99T/Y146D/K224F |

In Table 11, mutations are identified using the chymotrypsin numbering system. Thus, W215Y means that a tryptophan at position 215 of MT-SP1 according to the chymotrypsin numbering system is changed to a tyrosine at that position.

In any given embodiment, a mutated MT-SP1 polypeptide ("mutein") may contain a single mutation per polypeptide, or may contain two or more mutated residues per polypeptide, in any combination. Exemplary replacements of wild-type residues are provided in Table 10. In one exemplary embodiment, a Leu residue at position 172 is replaced with an Asp residue, wherein the mutein is designated as L172D. In another exemplary embodiment, an Asp60b residue is replaced by any one of Ala, Arg, Ile or Phe. In a further exemplary embodiment a variant MT-SP1 includes at least one of Y146F, L172D, Q175D and D217F, and may contain two, three, four or more such residue replacements.

Expression And Purification of MT-SP1 Muteins

In one embodiment, the protease is expressed in an active form. In another embodiment, the protease is expressed in an inactive, zymogen form. In one embodiment, the protease is expressed by a heterologous expression system such as an *E. coli, Pichia pastoris, S. cerevisiae*, or a baculovirus expression system. In a preferred embodiment, the protease is expressed in a mammalian cell culture expression system. Exemplary mammalian cell cultures are derived from rat, mouse, or preferably human cells. The protein can either be expressed in an intracellular environment or excreted (secreted) into the media. The protease can also be expressed in an in vitro expression system.

To purify variant MT-SP1 proteases, column chromatography can be used. The protease may be engineered to contain a 6-His tag for purification on a Nickel column. Depending on the pI of the protease, a cation or anion exchange column can be used in the purification method for the protease. Purification can also be accomplished through immunoabsorption, gel filtration, or any other purification method used in the art. The protease can be stored in a low pH buffer that minimizes its catalytic activity so that it will not degrade itself. This is further illustrated in Example 2.

Synthesis of Libraries for Characterization of MT-SP1 Muteins

Those of skill in the art will recognize that many methods can be used to prepare the peptides and the libraries of the invention. Suitable embodiments are further illustrated in Example 3.

Determination of Specificity Changes for MT-SP1 Muteins

Essential amino acids in the MT-SP1 muteins generated using the methods of the present invention are identified according to procedures known in the art, such as site-directed mutagenesis or saturation mutagenesis of active site residues, or disclosed herein. In one technique, residues that form the S1-S4 pockets that have been shown to be important determinants of specificity are mutated to every possible amino acid, either alone or in combination. See, e.g., Legendre, et al., JMB (2000) 296: 87-102. Substrate specificities of the resulting mutants will be determined using the ACC positional scanning libraries and by single substrate kinetic assays. See, e.g., Harris, et al. PNAS, 2000, 97:7754-7759.

Multiple amino acid substitutions are made and tested using known methods of mutagenesis and screening, such as those disclosed herein or already known in the art. See, e.g., Reidhaar-Olson and Sauer 1988 Science 241:53-57, or Bowie and Sauer 1989 Proc. Natl. Acad. Sci. USA 86:2152-2156. Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display based methods (e.g., Legendre et al., JMB, 2000: 296:87-102; Lowman et al., Biochem. 30:10832-10837, 1991; Ladner et al., U.S. Pat. No. 5,223,409; Huse, PCT Publication WO 92/06204) and region-directed mutagenesis (Derbyshire et al., Gene 46:145, 1986; Ner et al., DNA 7:127, 1988).

Mutagenesis methods as disclosed above can be combined with high-throughput, automated screening methods to detect activity of cloned, mutagenized polypeptides in host cells. Mutagenized DNA molecules that encode proteolytically active proteins or precursors thereof are recovered from the host cells and rapidly sequenced using modern equipment. These methods allow the rapid determination of the importance of individual amino acid residues in a polypeptide of interest, and can be applied to polypeptides of unknown structure.

In one embodiment, protease phage display is used to screen the libraries of mutant proteases of the invention for various affinities to specific substrate sequences as described in the art. See, e.g., Legendre et al., JMB, 2000: 296:87-102, and Corey et al., Gene, 1993 Jun. 15; 128 (1):129-34.

The invention also provides methods for detecting and quantitating an enzymatically active protease of the invention. The method includes: (a) contacting a sample with a protease, in such a manner whereby a fluorogenic moiety is released from a peptide substrate sequence upon action of the protease, thereby producing a fluorescent moiety; and (b) observing whether the sample undergoes a detectable change in fluorescence, the detectable change being an indication of the presence of the enzymatically active protease in the sample.

In one embodiment, these methods are used select for an MT-SP1 mutein that specifically cleaves a target sequence in VEGF or VEGFR, and preferably for an enzymatically active protease. In another embodiment, these methods are used to determine the sequence specificity of an MT-SP1 mutein. Suitable methods for determining specificity of MT-SP1 muteins are further illustrated in Examples 3-5.

The methods illustrated in Examples 1-5 can be repeated iteratively or in parallel to create a variant protease that has the desired specificity and selectivity at each of the extended binding subsites, P2, P3, and P4. In some cases, mutations in serine proteases have shown that each of the subsites that form the active site (S1-S4) function independently of one another, such that modification of specificity at one subsite has little influence on specificity at adjacent subsites. Thus, engineering substrate specificity and selectivity throughout the extended binding site can be accomplished in a step-wise manner.

Mutant proteases that match the desired specificity profiles, as determined by substrate libraries, are then assayed using individual peptide substrates corresponding to the desired cleavage sequence. Variant proteases are also assayed to ascertain that they will cleave the desired sequence when presented in the context of the full-length protein. The activity of the target protein is also assayed to verify that its function has been destroyed by the cleavage event. The cleavage event is monitored by SDS-PAGE after incubating the purified full-length protein with the variant protease. In another embodiment, mutations are combined to acquire the specificity of multiple proteases. A mutation at one residue of a scaffold, which produces specificity at one site, is combined in the same protease with another mutation at another site on the scaffold to make a combined specificity protease.

Any number of mutations at discrete sites on the same scaffold can be used to create a combined specificity protease. In one embodiment, the MT-SP1 scaffold comprises a polypeptide 95% identical to the amino acid sequence of wild type MT-SP1 of SEQ ID NO:1, and the polypeptide has at least one mutation at one or more of the positions 171, 174, 180, 215, 192, 218, 99, 57, 189, 190, 226, 146, 172, 175, 41, 58, 59, 60, 61, 62, 63, 97, 98, 100, 102, 151, 169, 170, 171A, 173, 176, 177, 178, 179, 181, 191, 195 or 224 or 217, wherein the numbering is for chymotrypsin.

These sites belong to the following S pockets:
S1': 146, 151,
S1: 189, 190, 226, 191, 195
S2: 99, 41, 57, 58, 59, 60, 61, 62, 63, 97, 98, 100, 102
S3: 192, 218, 146
S4: 171, 174, 179, 180, 215, 99, 172, 175, 97. 98, 169, 170, 171A, 173, 176, 177, 178, 181, 224, 217

In an exemplary embodiment, the mutein is L172D comprising leucine replaced with aspartic acid at position 172. In another embodiment, the mutein is Y146F comprising tyrosine replaced with phenylalanine at position 146. In a another embodiment, the mutein is Q175D comprising glutamine replaced with aspartic acid at position 175. In another embodiment, the mutein is D217F comprising aspartic acid replaced with phenylalanine at position 217. In one embodiment, at least one residue is replaced as compared to the MT-SP1 wild type polypeptide sequence of SEQ ID NO:1. Further nonlimiting contemplated MT-SP1 muteins are provided herein.

Proteins targeted for cleavage and inactivation can be identified by the following criteria: 1) the protein is involved in pathology; 2) there is strong evidence the protein is the critical point of intervention for treating the pathology; 3) proteolytic cleavage of the protein will likely destroy its function. By these criteria, VEGF and the VEGFRs are excellent targets for protease-mediated therapies of the invention. Cleavage sites within target proteins are identified by the following criteria: 1) they are located on the exposed surface of the protein; 2) they are located in regions that are devoid of secondary structure (i.e. not in β sheets or α helices), as determined by atomic structure or structure prediction algorithms (these regions tend to be loops on the surface of proteins or stalks on cell surface receptors); or 3) they are located at sites that are likely to inactivate the protein, based on its known function. Cleavage sequences are e.g., four residues in length to match the extended substrate specificity of many serine proteases, but can be longer or shorter.

In one embodiment of the invention, target protein-assisted catalysis is used to generate proteases specific for a target VEGF or VEGFR protein. A single mutation in the substrate sequence binding site of the protease can alter its specificity and cause it to have a change in substrate sequence specificity. Thus, substrate sequence specificity can be altered using one or only a small number of mutations.

Using the methods disclosed above, one of ordinary skill in the art can identify and/or prepare a variety of polypeptides that are substantially homologous to a protease scaffold or allelic variants thereof and retain the proteolysis activity of the wild-type protein scaffold but vary from it in specificity. In one embodiment, these polypeptides are based on the scaffold amino acid sequence of MT-SP1. Such polypeptides may optionally include a targeting moiety comprising additional amino acid residues that form an independently folding binding domain. Such domains include, for example, an extracellular ligand-binding domain (e.g., one or more fibronectin type III domains) of a cytokine receptor; immunoglobulin domains; DNA binding domains (see, e.g., He et al., Nature 378:92-96, 1995); affinity tags; and the like. Such polypeptides may also include additional polypeptide segments as generally disclosed above.

Protease Polypeptides

The protease muteins and protease libraries of the invention include polypeptides having an amino acid sequence of one or more of the proteases described herein. The invention also provides mutant or variant proteases that, relative to MT-SP1, has residues different from the corresponding residues of MT-SP1, while still maintaining its protease activity and physiological functions, and functional fragments thereof. In a preferred embodiment, the mutations in the MT-SP1 muteins of the invention occur in the S1-S4 regions of the protease as detailed herein.

In general, a protease variant that preserves protease-like function includes any variant in which residues at a particular position in the sequence have been substituted by other amino acids, and further include variants produced by, relative to the wild-type or parent protein sequence, inserting an additional residue or residues between two residues of the parent protein as well as by deleting one or more residues from the parent sequence. Any amino acid substitution, insertion, or deletion is contemplated by the methods, muteins, and mutein libraries of the invention. In favorable circumstances, the substitution is a conservative substitution, as described above.

One aspect of the invention pertains to isolated proteases, and biologically-active portions thereof, as well as derivatives, fragments, analogs or homologs thereof. Also provided are polypeptide fragments suitable for use as immunogens to raise anti-protease antibodies. In one embodiment, proteases of the invention are produced by recombinant DNA techniques. As an alternative to recombinant expression, a protease protein or polypeptide can be synthesized chemically using standard peptide synthesis techniques, as described above.

Biologically-active portions of protease proteins include peptides comprising amino acid sequences homologous to or derived from the amino acid sequences of the full-length protease proteins, but with fewer amino acids than the full-length protease proteins, and that exhibit at least one activity of the full-length protease protein. Typically, biologically-active portions comprise a domain or motif with at least one activity of the protease protein. A biologically-active portion of a protease protein is a polypeptide which is, for example, 10, 25, 50, 60, 70, 80, 90, 100, 110, 120, 130, 140, 150, 160, 170, 180, 190, 200, 210, 220, 230, 240, 250, 260, 270, 280, 290, 300 or more amino acid residues in length, and increasing in amino acid length in whole integers of one (1), up to a length of 855 amino acids, wherein wild-type full length MT-SP1 is considered to be 855 amino acids in length (SEQ ID NO:1), and mature is less than 855 aa in length. In general, a "fragment" or a "portion" of a polypeptide contains at least one less amino acid residue than the full length polypeptide. The one or more deleted amino acids may be removed from the N-terminus, the C-terminus, or an internal portion.

Moreover, other biologically-active portions of a protein, from which other regions of the protein have been deleted, can be prepared by recombinant techniques and evaluated for one or more of the functional activities of a native protease.

In one embodiment, the protease has an amino acid sequence of MT-SP1 or one of the mutants of the MT-SP1 scaffold. Thus, the protease protein is substantially homologous to MT-SP1 or one of its muteins, and retains the functional activity of MT-SP1, yet differs in amino acid sequence due to natural allelic variation or mutagenesis, and may differ in specificity, as described herein. Representative MT-SP1 muteins are disclosed in Tables 10 and 11 herein.

Determining Homology Between Two or More Sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid or amino acid sequence homology may be determined as the degree of identity between two sequences. The homology may be determined using computer programs known in the art, such as GAP software provided in the GCG program package. See, Needleman and Wunsch, 1970. *J Mol Biol* 48: 443-453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides protease chimeric or fusion proteins. As used herein, a protease "chimeric protein" or "fusion protein" comprises a protease polypeptide operatively-linked to a non-protease polypeptide. A "protease polypeptide" refers to a polypeptide having an amino acid sequence corresponding to one of the scaffolds such as MT-SP1 described herein or one of the mutants of the MT-SP1 scaffold, whereas a "non-protease polypeptide" refers to a polypeptide having an amino acid sequence corresponding to a protein that is not substantially homologous to one of the scaffolds, e.g., a protein that is different from the scaffold and that is derived from the same or a different organism. Within a protease fusion protein, the protease polypeptide can correspond to all or a portion of a parent or scaffold protease protein. In one embodiment, a protease fusion protein comprises at least one biologically-active portion of a protease protein. In another embodiment, a protease fusion protein comprises at least two biologically-active portions of a protease protein. In yet another embodiment, a protease fusion protein comprises at least three biologically-active portions of a protease protein. Within the fusion protein, the term "operatively-linked" is intended to indicate that the protease polypeptide and the non-protease polypeptide are fused in-frame with one another. The non-protease polypeptide can be fused to the N-terminus or C-terminus of the protease polypeptide.

In one embodiment, the fusion protein is a GST-protease fusion protein in which the protease sequences are fused to the N-terminus of the GST (glutathione S-transferase) sequences. Such fusion proteins can facilitate the purification of recombinant protease polypeptides.

In another embodiment, the fusion protein is an Fc fusion in which the protease sequences are fused to the N-terminus of the Fc domain from immunoglobulin G. Such fusion proteins can have better pharmacodynamic properties in vivo.

In another embodiment, the fusion protein is a protease protein containing a heterologous signal sequence at its N-terminus. In certain host cells (e.g., mammalian host cells), expression and/or secretion of protease can be increased through use of a heterologous signal sequence.

A protease chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A protease-encoding nucleic acid can be cloned into such an expression vector such that the fusion moiety is linked in-frame to the protease protein.

Protease Agonists and Antagonists

The invention also pertains to variants of the protease proteins that function as either protease agonists (i.e., mimetics) or as protease antagonists. Variants of the protease protein can be generated by mutagenesis (e.g., discrete point mutation or truncation of the protease protein). An agonist of the protease protein retains substantially the same, or a subset of, the biological activities of the naturally occurring form of the protease protein. For example, an agonist protease activates a target protein (e.g., a cell surface receptor) by cleaving a substrate sequence within the protein. An antagonist of the protease protein can inhibit one or more of the activities of the naturally occurring form of the protease protein by, for example, cleaving the same target protein as the protease protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the protease proteins.

Protease Therapy in Combination with Anti-Cancer Agents

Signaling by vascular endothelial growth factor (VEGF) and its receptors is implicated in pathological angiogenesis and the rapid development of tumor vasculature in cancer. Drugs that block this signaling pathway prevent the growth and maintenance of tumor blood supply, and lead to the systematic death of the tumor. The recent success of the anti-VEGF antibody AVASTIN™ in patients with metastatic colon cancer has validated VEGF as a target for anti-angiogenic therapy of cancer. Despite these encouraging results, tumor progression has still occurred despite anti-VEGF treatment. The mechanisms of antibody affecting VEGF function and how the antibody impedes tumor growth are unknown. Knock down experiments show that blocking VEGF function blocks angiogenesis. Thus the inhibition of angiogenic signaling through VEGFR-2 represents an underdeveloped therapeutic area ideal for the development of engineered proteases with novel targeting.

Due to their catalytic nature and smaller size, engineered proteases promise a new therapeutic treatment with advantages over competing targeted binding proteins. The expected advantages include, but are not limited to: better tumor penetration, better target saturation, higher effectiveness, and potentially lower dosing. Notably, because they bind, hydrolyze, and release, a single protease could cleave and inactivate hundreds to thousands of substrate VEGF receptors, offering substantial therapeutic amplification.

In one embodiment, treatment of a pathology, such as a cancer, is provided comprising administering to a subject in need thereof therapeutically effective amounts of a protease that specifically cleaves and inactivates the signaling of the VEGF/VEGFR-2 complex, such as protease MT-SP1 or an MT-SP1 mutein described herein, which is administered alone or in combination with at least one anti-cancer agent. Anti-angiogenic therapy has proven successful against both solid cancers and hematological malignancies. See, e.g., Ribatti et al. 2003 J Hematother Stem Cell Res. 12 (1), 11-22. Therefore, compositions of the invention provided as anti-angiogenic therapy will facilitate the treatment of both hematological and sold tissue malignancies. Compositions and methods of treatment provided in the invention may be administered alone or in combination with any other appropriate anti-cancer treatment known to one skilled in the art. For example, the MT-SP1 and MT-SP1 muteins of the invention can be administered in combination with or in place of AVASTIN™ in any therapy where AVASTIN™ administration provides therapeutic benefit.

In one embodiment, the anti-cancer agent is at least one chemotherapeutic agent. In a related embodiment, the administering of the protease is in combination with at least one radiotherapy. Administration of the combination therapy will attenuate the angiogenic signal and create a pool of soluble receptor that lowers free VEGF levels. In a specific embodiment, a variant MT-SP1 protease of the invention has an in vitro specificity that matches a critical region of the receptor, the Flk-1/KDR stalk, over a six amino acid region.

The MT-SP1 mutein polypeptide of the invention may be administered in a composition containing more than one therapeutic agent. The therapeutic agents may be, for example, therapeutic radionuclides, drugs, hormones, hormone antagonists, receptor antagonists, enzymes or proenzymes activated by another agent, autocrines, cytokines or any suitable anti-cancer agent known to those skilled in the art. In one embodiment, the anti-cancer agent co-administered with the MT-SP1 or MT-SP1 mutein is AVASTIN™. Toxins also can be used in the methods of the present invention. Other therapeutic agents useful in the present invention include anti-DNA, anti-RNA, radiolabeled oligonucleotides, such as antisense oligonucleotides, anti-protein and anti-chromatin cytotoxic or antimicrobial agents. Other therapeutic agents are known to those skilled in the art, and the use of such other therapeutic agents in accordance with the present invention is specifically contemplated.

The antitumor agent may be one of numerous chemotherapy agents such as an alkylating agent, an antimetabolite, a hormonal agent, an antibiotic, an antibody, an anti-cancer biological, Gleevec, colchicine, a vinca alkaloid, L-asparaginase, procarbazine, hydroxyurea, mitotane, nitrosoureas or an imidazole carboxamide. Suitable agents are those agents that promote depolarization of tubulin or prohibit tumor cell proliferation. Chemotherapeutic agents contemplated as within the scope of the invention include, but are not limited to, anti-cancer agents listed in the Orange Book of Approved Drug Products With Therapeutic Equivalence Evaluations, as compiled by the Food and Drug Administration and the U.S. Department of Health and Human Services. In addition to the above chemotherapy agents, the MT-SP1 proteases of the invention may also be administered together with radiation therapy treatment. Additional treatments known in the art are contemplated as being within the scope of the invention.

The therapeutic agent may be a chemotherapeutic agent. Chemotherapeutic agents are known in the art and include at least the taxanes, nitrogen mustards, ethylenimine derivatives, alkyl sulfonates, nitrosoureas, triazenes, folic acid analogs, pyrimidine analogs, purine analogs, vinca alkaloids, antibiotics, enzymes, platinum coordination complexes, substituted urea, methyl hydrazine derivatives, adrenocortical suppressants, or antagonists. More specifically, the chemotherapeutic agents may be one or more agents chosen from the non-limiting group of steroids, progestins, estrogens, antiestrogens, or androgens. Even more specifically, the chemotherapy agents may be azaribine, bleomycin, bryostatin-1, busulfan, carmustine, chlorambucil, cisplatin, CPT-11, cyclophosphamide, cytarabine, dacarbazine, dactinomycin, daunorubicin, dexamethasone, diethylstilbestrol, doxorubicin, ethinyl estradiol, etoposide, fluorouracil, fluoxymesterone, gemcitabine, hydroxyprogesterone caproate, hydroxyurea, L-asparaginase, leucovorin, lomustine, mechlorethamine, medroprogesterone acetate, megestrol acetate, melphalan, mercaptopurine, methotrexate, mithramycin, mitomycin, mitotane, phenyl butyrate, prednisone, procarbazine, semustine streptozocin, tamoxifen, taxanes, taxol, testosterone propionate, thalidomide, thioguanine, thiotepa, uracil mustard, vinblastine, or vincristine. The use of any combinations of chemotherapy agents is also contemplated. The administration of the chemotherapeutic agent may be before, during or after the administration of the MT-SP1 or the MT-SP1 mutein polypeptide.

Other suitable therapeutic agents for use in combination or for co-administration with the proteases of the invention are selected from the group consisting of radioisotope, boron addend, immunomodulator, toxin, photoactive agent or dye, cancer chemotherapeutic drug, antiviral drug, antifungal drug, antibacterial drug, antiprotozoal drug and chemosensitizing agent (See, U.S. Pat. Nos. 4,925,648 and 4,932,412). Suitable chemotherapeutic agents are described, for example, in REMINGTON'S PHARMACEUTICAL SCIENCES, 19th Ed. (Mack Publishing Co. 1995), and in Goodman and Gilman's THE PHARMACOLOGICAL BASIS OF THERAPEUTICS (Goodman et al., Eds. Macmillan Publishing Co., New York, 1980 and 2001 editions). Other suitable chemotherapeutic agents, such as experimental drugs, are known to those of skill in the art. Moreover a suitable therapeutic radioisotope is selected from the group consisting of α-emitters, β-emitters, γ-emitters, Auger electron emitters, neutron capturing agents that emit α-particles and radioisotopes that decay by electron capture. Preferably, the radioisotope is selected from the group consisting of $^{225}$Ac, $^{198}$Au, $^{32}$P, $^{125}$I, $^{131}$I, $^{90}$Y, $^{186}$Re, $^{188}$Re, $^{67}$Cu, $^{177}$Lu, $^{213}$Bi, $^{10}$B, and $^{211}$At.

Where more than one therapeutic agent is used in combination with the proteases of the invention, they may be of the same class or type or may be from different classes or types. For example, the therapeutic agents may comprise different radionuclides, or a drug and a radionuclide.

In another embodiment, different isotopes that are effective over different distances as a result of their individual energy emissions are used as first and second therapeutic agents in combination with the proteases of the invention. Such agents can be used to achieve more effective treatment of tumors, and are useful in patients presenting with multiple tumors of differing sizes, as in normal clinical circumstances.

Few of the available isotopes are useful for treating the very smallest tumor deposits and single cells. In these situations, a drug or toxin may be a more useful therapeutic agent for co-administration with a protease of the invention. Accordingly, in some embodiments of the present invention, isotopes are used in combination with non-isotopic species such as drugs, toxins, and neutron capture agents and co-administered with a protease of the invention. Many drugs and toxins are known which have cytotoxic effects on cells, and can be used in combination with the proteases of the present invention. They are to be found in compendia of drugs and toxins, such as the Merck Index, Goodman and Gilman, and the like, and in the references cited above.

Drugs that interfere with intracellular protein synthesis can also be used in combination with a protease in the therapeutic methods of the present invention; such drugs are known to those skilled in the art and include puromycin, cycloheximide, and ribonuclease.

The therapeutic methods of the invention may be used for cancer therapy. It is well known that radioisotopes, drugs, and toxins can be conjugated to antibodies or antibody fragments which specifically bind to markers which are produced by or associated with cancer cells, and that such antibody conjugates can be used to target the radioisotopes, drugs or toxins to tumor sites to enhance their therapeutic efficacy and minimize side effects. Examples of these agents and methods are reviewed in Wawrzynczak and Thorpe (in *Introduction to the Cellular and Molecular Biology of Cancer*, L. M. Franks and N. M. Teich, eds, Chapter 18, pp. 378-410, Oxford University Press. Oxford, 1986), in *Immunoconjugates: Antibody Conjugates in Radioimaging and Therapy of Cancer* (C. W. Vogel, ed., 3-300, Oxford University Press, N.Y., 1987), in Dillman, R. O. (*CRC Critical Reviews in Oncology/Hematology* 1:357, CRC Press, Inc., 1984), in Pastan et al. (*Cell* 47:641, 1986), in Vitetta et al. (*Science* 238:1098-1104, 1987), and in Brady et al. (*Int. J. Rad. Oncol. Biol. Phys.* 13:1535-1544, 1987). Other examples of the use of immunoconjugates for cancer and other forms of therapy have been disclosed, inter alia, in U.S. Pat. Nos. 4,331,647, 4,348,376, 4,361,544, 4,468,457, 4,444,744, 4,460,459, 4,460,561 4,624,846, 4,818,709, 4,046,722, 4,671,958, 4,046,784, 5,332,567, 5,443,953, 5,541,297, 5,601,825, 5,635,603, 5,637,288, 5,677,427, 5,686,578, 5,698,178, 5,789,554, 5,922,302, 6,187,287, and 6,319,500.

Additionally, the treatment methods of the invention include those in which a protease of the invention is used in combination with other compounds or techniques for preventing, mitigating or reversing the side effects of certain cytotoxic agents. Examples of such combinations include, e.g., administration of IL-1 together with an antibody for rapid clearance, as described in e.g., U.S. Pat. No. 4,624,846. Such administration can be performed from 3 to 72 hours after administration of a primary therapeutic treatment with a MT-SP1 mutein in combination with a anti-cancer agent (e.g., with a radioisotope, drug or toxin as the cytotoxic component). This can be used to enhance clearance of the conjugate, drug or toxin from the circulation and to mitigate or reverse myeloid and other hematopoietic toxicity caused by the therapeutic agent.

In another aspect of the invention, and as noted above, cancer therapy may involve a combination of more than one tumoricidal agent, e.g., a drug and a radioisotope, or a radioisotope and a Boron-10 agent for neutron-activated therapy, or a drug and a biological response modifier, or a fusion molecule conjugate and a biological response modifier. The cytokine can be integrated into such a therapeutic regimen to maximize the efficacy of each component thereof.

Similarly, certain antileukemic and antilymphoma antibodies conjugated with radioisotopes that are β or α emitters may induce myeloid and other hematopoietic side effects when these agents are not solely directed to the tumor cells. This is observed particularly when the tumor cells are in the circulation and in the blood-forming organs. Concomitant and/or subsequent administration of at least one hematopoietic cytokine (e.g., growth factors, such as colony stimulating factors, such as G-CSF and GM-CSF) is preferred to reduce or ameliorate the hematopoietic side effects, while augmenting the anticancer effects.

It is well known in the art that various methods of radionuclide therapy can be used for the treatment of cancer and other pathological conditions, as described, e.g., in Harbert, "Nuclear Medicine Therapy", New York, Thieme Medical Publishers, 1087, pp. 1-340. A clinician experienced in these procedures will readily be able to adapt the cytokine adjuvant therapy described herein to such procedures to mitigate any hematopoietic side effects thereof. Similarly, therapy with cytotoxic drugs, co-administered with MT-SP1 or a MT-SP1 mutein, can be used, e.g., for treatment of cancer, infectious or autoimmune diseases, and for organ rejection therapy. Such treatment is governed by analogous principles to radioisotope therapy with isotopes or radiolabeled antibodies. Thus, the ordinary skilled clinician will be able to adapt the description of cytokine use to mitigate marrow suppression and other such hematopoietic side effects by administration of the cytokine before, during and/or after the primary anticancer therapy.

Pharmaceutical Compositions

Sequential or substantially simultaneous administration of each therapeutic MT-SP1 and other therapeutic agents combined with the protease can be effected by any appropriate route including, but not limited to, oral routes, intravenous routes, intramuscular routes, and direct absorption through mucous membrane tissues. MT-SP1 and other therapeutic agents can be administered by the same route or by different routes. For example, MT-SP1 may be administered by intravenous injection while the other therapeutic agent(s) of the combination may be administered orally. Alternatively, for example, the other therapeutic agent(s) may be administered by intravenous injection. The sequence in which the therapeutic agents are administered is not narrowly critical.

Administration of MT-SP1 also can be accompanied by the administration of the other therapeutic agents as described above in further combination with other biologically active ingredients and non-drug therapies (e.g., surgery or radiation treatment) or with non-drug therapies alone with MT-SP1. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Thus, MT-SP1 and the other pharmacologically active agent may be administered to a patient simultaneously, sequentially or in combination. If administered sequentially, the time between administrations generally varies from 0.1 to about 48 hours. It will be appreciated that when using MT-SP1 with other therapeutic agent(s), they may be in the same pharmaceutically acceptable carrier and therefore administered simultaneously. They may be in separate pharmaceutical carriers such as conventional oral dosage forms which are taken simultaneously.

A therapy for a angiogenic condition includes MT-SP1 and AVASTIN™. In one embodiment, this condition is cancer.

A therapy for cancer, inflammation, diabetes or macular degeneration includes MT-SP1. In another embodiment, this therapy further includes another therapeutic as defined above.

Advantages attributed to the administration of MT-SP1 and at least a second agent as part of a specific treatment regimen includes, but is not limited to, pharmacokinetic or pharmacodynamic co-action resulting from the combination of therapeutic agents. In one embodiment, the co-action of the therapeutic agents is additive. In another embodiment, the co-action of the therapeutic agents is synergistic. In another embodiment, the co-action of the therapeutic agents improves the therapeutic regimen of one or both of the agents.

The invention further relates to kits for treating patients having an angiogenic condition, such as cancer, comprising a therapeutically effective dose of MT-SP1 for treating or at least partially alleviating the symptoms of the condition (e.g., AVASTIN™), either in the same or separate packaging, and instructions for its use.

The present invention is suitable for the reduction of cancer symptoms. These cancer symptoms include blood in the urine, pain or burning upon urination, frequent urination, cloudy urine, pain in the bone or swelling around the affected site, fractures in bones, weakness, fatigue, weight loss, repeated infections, nausea, vomiting, constipation, problems with urination, weakness or numbness in the legs, bumps and bruises that persist, dizziness, drowsiness, abnormal eye movements or changes in vision, weakness, loss of feeling in arms or legs or difficulties in walking, fits or convulsions, changes in personality, memory or speech, headaches that tend to be worse in the morning and ease during the day, that may be accompanied by nausea or vomiting, a lump or thickening of the breast, discharge from the nipple, change in the skin of the breast, a feeling of heat, or enlarged lymph nodes under the arm, rectal bleeding (red blood in stools or black stools), abdominal cramps, constipation alternating with diarrhea, weight loss, loss of appetite, weakness, pallid complexion, dull ache or pain in the back or side, lump in kidney area, sometimes accompanied by high blood pressure or abnormality in red blood cell count, weakness, paleness, fever and flu-like symptoms, bruising and prolonged bleeding, enlarged lymph nodes, spleen, liver, pain in bones and joints, frequent infections, weight loss, night sweats, wheezing, persistent cough for months, blood-streaked sputum, persistent ache in chest, congestion in lungs, enlarged lymph nodes in the neck, change in mole or other bump on the skin, including bleeding or change in size, shape, color, or texture, painless swelling in the lymph nodes in the neck, underarm, or groin, persistent fever, feeling of fatigue, unexplained weight loss, itchy skin and rashes, small lumps in skin, bone pain, swelling in the abdomen, liver or spleen enlargement, a lump in the mouth, ulceration of the lip, tongue or inside of the mouth that does not heal within a couple of weeks, dentures that no longer fit well, oral pain, bleeding, foul breath, loose teeth, changes in speech, abdominal swelling, abnormal vaginal bleeding, digestive discomfort, upper abdominal pain, unexplained weight loss, pain near the center of the back, intolerance of fatty foods, yellowing of the skin, abdominal masses, enlargement of liver and spleen, urination difficulties due to blockage of the urethra, bladder retains urine, creating frequent feelings of urgency to urinate, especially at night, bladder not emptying completely, burning or painful urination, bloody urine, tenderness over the bladder, dull ache in the pelvis or back, indigestion or heartburn, discomfort or pain in the abdomen, nausea and vomiting, diarrhea or constipation, bloating after meals, loss of appetite, weakness and fatigue, bleeding—vomiting blood or blood in the stool, abnormal vaginal bleeding, a watery bloody discharge in postmenopausal women, a painful urination, pain during intercourse, and pain in pelvic area Preferably, treatment should continue as long as cancer symptoms are suspected or observed.

The present invention is suitable for the reduction of macular degeneration symptoms. These macular degeneration symptoms include blurring of vision, lines forming in vision and gradual or quick loss of vision.

The present invention is suitable for the reduction of diabetes symptoms. These diabetes symptoms include loss of vision and blindness.

To evaluate whether a patient is benefiting from the (treatment), one would examine the patient's symptoms in a quantitative way, by decrease in the frequency of relapses, or increase in the time to sustained progression, or improvement and compare the patient's status measurement before and after treatment. In a successful treatment, the patient status will have improved. Measurement number or frequency of relapses will have decreased, or the time to sustained progression will have increased.

As for every drug, the dosage is an important part of the success of the treatment and the health of the patient. In every case, in the specified range, the physician has to determine the best dosage for a given patient, according to gender, age, weight, height, pathological state and other parameters.

The pharmaceutical compositions of the present invention contain a therapeutically effective amount MT-SP1. The amount of the compound will depend on the patient being treated. The patient's weight, severity of illness, manner of administration and judgment of the prescribing physician should be taken into account in deciding the proper amount. The determination of a therapeutically effective amount of MT-SP1 or other therapeutic agent is well within the capabilities of one with skill in the art.

In some cases, it may be necessary to use dosages outside of the ranges stated in pharmaceutical packaging insert to treat a patient. Those cases will be apparent to the prescribing physician. Where it is necessary, a physician will also know how and when to interrupt, adjust or terminate treatment in conjunction with a response of a particular patient.

Formulation (Separately or Together) and Administration

The compounds of the present invention are administered separately or co-formulated in a suitable co-formulated dosage form. Compounds, including those used in combination therapies are administered to a patient in the form of a pharmaceutically acceptable salt or in a pharmaceutical composition. A compound that is administered in a pharmaceutical composition is mixed with a suitable carrier or excipient such that a therapeutically effective amount is present in the composition. The term "therapeutically effective amount" refers to an amount of the compound that is necessary to achieve a desired endpoint (e.g., decreasing symptoms associated with cancer).

A variety of preparations can be used to formulate pharmaceutical compositions containing MT-SP1 and other therapeutic agents. Techniques for formulation and administration may be found in "Remington: The Science and Practice of Pharmacy, Twentieth Edition," Lippincott Williams & Wilkins, Philadelphia, Pa. Tablets, capsules, pills, powders, granules, dragees, gels, slurries, ointments, solutions suppositories, injections, inhalants and aerosols are examples of such formulations. The formulations can be administered in either a local or systemic manner or in a depot or sustained release fashion. Administration of the composition can be performed in a variety of ways. The compositions and combination therapies of the invention may be administered in combination with a variety of pharmaceutical excipients, including stabilizing agents, carriers and/or encapsulation formulations as described herein.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including creams, lotions, mouthwashes, inhalants and the like.

For human administration, preparations should meet sterility, pyrogenicity, general safety and purity standards as required by the FDA.

Administration of compounds alone or in combination therapies may be, e.g., subcutaneous, intramuscular or intravenous injection, or any other suitable route of administration. A particularly convenient frequency for the administration of the compounds of the invention is once a day.

Upon formulation, therapeutics will be administered in a manner compatible with the dosage formulation, and in such amount as is pharmacologically effective. The formulations are easily administered in a variety of dosage forms, such as the injectable solutions described, but drug release capsules and the like can also be employed. In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals.

A carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Suitable preservatives for use in solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

The compounds and combination therapies of the invention can be formulated by dissolving, suspending or emulsifying in an aqueous or nonaqueous solvent. Vegetable (e.g., sesame oil, peanut oil) or similar oils, synthetic aliphatic acid glycerides, esters of higher aliphatic acids and propylene glycol are examples of nonaqueous solvents. Aqueous solutions such as Hank's solution, Ringer's solution or physiological saline buffer can also be used. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for subcutaneous or intramuscular injection is also contemplated. In this regard, the use of DMSO as solvent is preferred as this will result in extremely rapid penetration, delivering high concentrations of the active compound(s) or agent(s) to a small area.

Where one or both active ingredients of the combination therapy is given orally, it can be formulated through combination with pharmaceutically acceptable carriers that are well known in the art. The carriers enable the compound to be formulated, for example, as a tablet, pill, capsule, solution, suspension, sustained release formulation; powder, liquid or gel for oral ingestion by the patient. Oral use formulations can be obtained in a variety of ways, including mixing the compound with a solid excipient, optionally grinding the resulting mixture, adding suitable auxiliaries and processing the granule mixture. The following list includes examples of excipients that can be used in an oral formulation: sugars such as lactose, sucrose, mannitol or sorbitol; cellulose preparations such as maize starch, wheat starch, potato starch, gelatin, gum tragacanth, methyl cellulose, hydroxypropylmethylcellulose, sodium carboxymethylcellulose and polyvinylpyrrolidone (PVP). Oral formulations include such normally employed excipients as, for example, pharmaceutical grades of mannitol, lactose, starch, magnesium stearate, sodium saccharine, cellulose, magnesium carbonate and the like.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabensas preservatives, a dye and flavoring, such as cherry or orange flavor.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

The subject treated by the methods of the invention is a mammal, more preferably a human. The following properties or applications of these methods will essentially be described for humans although they may also be applied to non-human mammals, e.g., apes, monkeys, dogs, mice, etc. The invention therefore can also be used in a veterinarian context.

The following examples are nonlimiting and meant only to illustrate various aspects of the invention.

EXAMPLES

Example 1

Methods of Cloning and Characterizing Engineered MT-SP1 Protease with Altered Substrate Specificity Based on Well Understood Starting Scaffolds The serine protease MT-SP1 has been chosen as scaffold protease for mutagenesis towards specific proteolysis of VEGF and VEGFR in part because it has been well characterized with biochemical and structural techniques [Harris, Recent Results Cancer Res. 1998; 152:341-52].

Figure 4A:
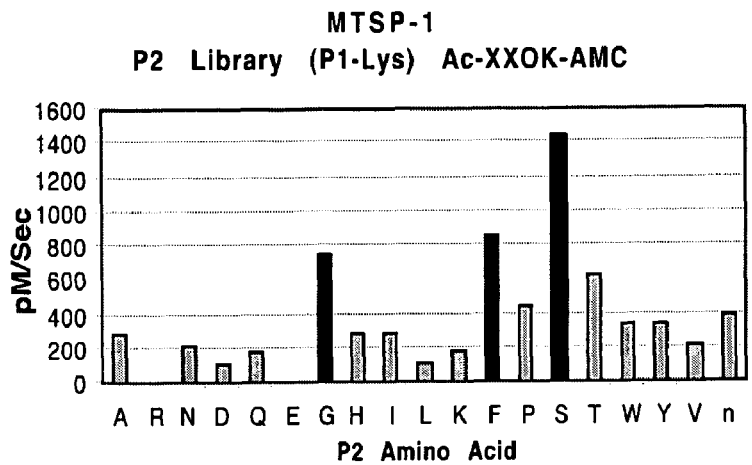
FIGS. 4A, 4B and 4C are graphical depictions of the PSSCL substrate specificity profile at P2, P3 and P4, respectively, of human MT-SP1 in a P1-Lys fixed library. The library format for each extended position is listed above the profile. The activity is represented in pM/sec on the y-axis for each amino acid along the x-axis.
Figure 4B:
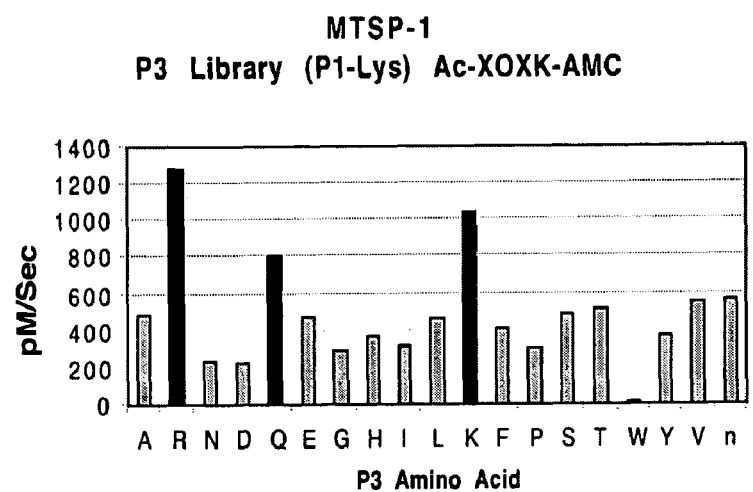
Figure 4C:
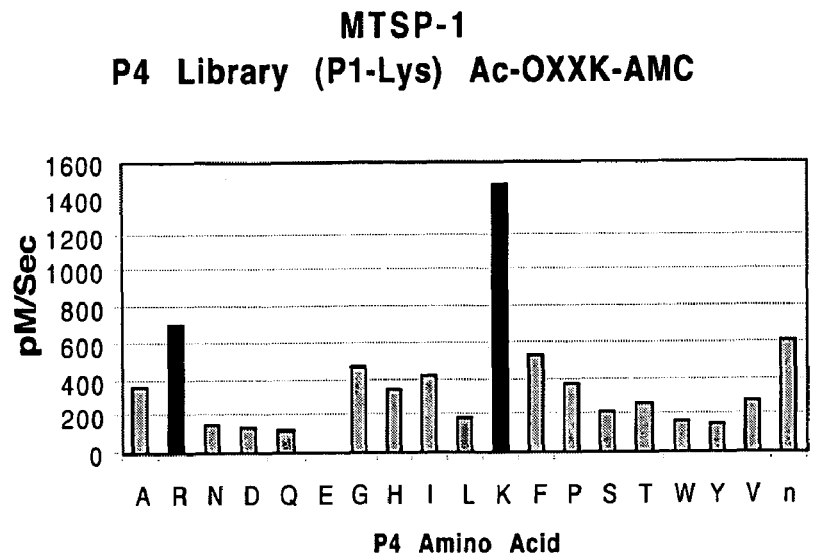

MT-SP1 is a membrane bound serine protease with multiple extracellular protein-protein interaction domains. The protease domain alone has been profiled using the totally diverse and P1-Lys PSSCL (FIG. 4A-4C) revealing an extended specificity of (basic)-(non-basic)-Ser-Arg or (non-basic)-(basic)-Ser-Arg/Lys. The X-ray crystallographic structure of MT-SP1 reveals components proposed to regulate activity and a nine amino acid insertion in the 60's loop that may determine P2 specificity Variants of MT-SP1 have been created and characterized. Various protease muteins have been expressed and purified, as described below. Initial activity to verify activity and specificity have been performed, and sample results are provided in FIGS. 1-11.

Example 2

Expression and Purification of MT-SP1

A mutated MT-SP1 polypeptide ("mutein") may contain a single mutation per polypeptide, or may contain two or more mutated residues in any combination, as illustrated in Table 11.

Wild-type and mutant MT-SP1 are cloned into the pQE bacterial expression vector (Qiagen) containing an N-terminal 6 histidine tag, prodomain, and protease domain and the resulting constructs transformed into BL21 E. coli cells. Cells are grown in 100 mL cultures to an OD of 0.6, and expression of the protease in inclusion bodies is induced by adding IPTG to a final concentration of 1 mM. After 4-6 hours, the bacteria are pelleted by centrifugation and the pellet resuspended in 50 mM Tris pH 8, 500 mM KCl, and 10% glycerol (buffer A). Cells are lysed by sonication and pelleted by centrifugation at 6000×g. Pellets are resuspended in 50 mM Tris pH 8, 6 M urea, 100 mM NaCl and 1% 2-mercaptoethanol (buffer B). Membrane and organelles are pelleted by centrifugation at 10,000×g and the supernatant is passed over a nickel NTA column (Qiagen). The column is washed with 50 mM Tris pH8, 6 M urea, 100 mM NaCl, 20 mM imidazole, 1% 2-mercaptoethanoland 0.01% Tween 20 (buffer D). The column is washed again with buffer D without Tween 20. The protease is then eluted from the column with 50 mM Tris pH 8, 6 M urea, 100 mM NaCl, 1% 2-mercaptoethanol and 250 mM imidazole (buffer E). The protease is then concentrated to a volume of ~1 mL and then dialyzed at 4° C. overnight in 1 L of 50 mM Tris pH8, 3 M urea, 100 mM NaCl, 1% 2-mercaptoethanol, and 10% glycerol. Finally, the protease is dialyzed into 50 mM Tris pH 8, 100 mM NaCl, and 10% glycerol at 4° C. overnight. During the last dialysis step; the protease becomes autoactivated by self-cleavage, resulting in the removal of the 6 histidine tag and prodomain.

Result. Multi-milligram quantities are obtained using this bacterial expression system. The protease is produced in inclusion bodies and is purified by a one-column purification procedure and then re-folded through successive dialysis steps (FIG. 1). Once refolded, the protease activates itself by cleavage at the juncture between the prodomain and the protease domain at the sequence RQAR (SEQ ID NO: 18)/VVGG (SEQ ID NO:6).

Example 3

Synthesis and Screening of Combinatorial Libraries for Characterization of MT-SP1 Wild-Type and Muteins Fixed P1 Amino Acid Method Individual P1-substituted Fmoc-amino acid ACC-resin (ca. 25 mg, 0.013 mmol) was added to wells of a Multi-Chem 96-well reaction apparatus. The resin-containing wells were solvated with DMF (0.5 mL). A 20% piperidine in DMF solution (0.5 mL) was added followed by agitation for 30 min. The wells of the reaction block were filtered and washed with DMF (3×0.5 mL). In order to introduce the randomized P2 position, an isokinetic mixture (Ostresh, J. M., et al., (1994) Biopolymers 34:1681-9) of Fmoc-amino acids (4.8 mmol, 10 equiv/well; Fmoc-amino acid, mol %: Fmoc-Ala-OH, 3.4; Fmoc-Arg(Pbf)-OH, 6.5; Fmoc-Asn(Trt)-OH, 5.3; Fmoc-Asp(O-t-Bu)-OH, 3.5; Fmoc-Glu(O-t-Bu)-OH, 3.6; Fmoc-Gln(Trt)-OH, 5.3; Fmoc-Gly-OH, 2.9; Fmoc-His(Trt)-OH, 3.5; Fmoc-Ile-OH, 17.4; Fmoc-Leu-OH, 4.9; Fmoc-Lys (Boc)-OH, 6.2; Fmoc-Nle-OH, 3.8; Fmoc-Phe-OH, 2.5; Fmoc-Pro-OH, 4.3; Fmoc-Ser(O-t-Bu)-OH, 2.8; Fmoc-Thr (O-t-Bu)-OH, 4.8; Fmoc-Trp(Boc)-OH, 3.8; Fmoc-Tyr(O-t-Bu)-OH, 4.1; Fmoc-Val-OH, 11.3) was pre-activated with DICI (390 µL, 2.5 mmol), and HOBt (340 mg, 2.5 mmol) in DMF (10 mL). The solution (0.5 mL) was added to each of the wells. The reaction block was agitated for 3 h, filtered, and washed with DMF (3×0.5 mL). The randomized P3 and P4 positions were incorporated in the same manner. The Fmoc of the P4 amino acid was removed and the resin was washed with DMF (3×0.5 mL), and treated with 0.5 mL of a capping solution of AcOH (150 μL, 2.5 mmol), HOBt (340 mg, 2.5 mmol) and DICI (390 μL, 2.5 mmol) in DMF (10 mL). After 4 h of agitation, the resin was washed with DMF (3×0.5 mL), $CH_2Cl_2$ (3×0.5 mL), and treated with a solution of 95:2.5:2.5 TFA/TIS/$H_2O$. After incubating for 1 h the reaction block was opened and placed on a 96 deep-well titer plate and the wells were washed with additional cleavage solution (2×0.5 mL). The collection plate was concentrated, and the substrate-containing wells were diluted with EtOH (0.5 mL) and concentrated twice. The contents of the individual wells were lyophilized from $CH_3CN:H_2O$ mixtures. The total amount of substrate in each well was conservatively estimated to be 0.0063 mmol (50%) based upon yields of single substrates.

P1-Diverse Amino Acid Method

7-Fmoc-aminocoumarin-4-acetic acid was prepared by treating 7-aminocoumarin-4-acetic acid with Fmoc-Cl. 7-Aminocoumarin-4-acetic acid (10.0 g, 45.6 mmol) and $H_2O$ (228 ml) were mixed. $NaHCO_3$ (3.92 g, 45.6 mmol) was added in small portions followed by the addition of acetone (228 ml). The solution was cooled with an ice bath, and Fmoc-Cl (10.7 g, 41.5 mmol) was added with stirring over the course of 1 h. The ice bath was removed and the solution was stirred overnight. The acetone was removed with rotary evaporation and the resulting gummy solid was collected by filtration and washed with several portions of hexane. ACC-resin was prepared by condensation of Rink Amide AM resin with 7-Fmoc-aminocoumarin-4-acetic acid. Rink Amide AM resin (21 g, 17 mmol) was solvated with DMF (200 ml). The mixture was agitated for 30 min and filtered with a filter cannula, whereupon 20% piperidine in DMF (200 ml) was added. After agitation for 25 min, the resin was filtered and washed with DMF (3 times, 200 ml each). 7-Fmoc-aminocoumarin-4-acetic acid (15 g, 34 mmol), HOBt (4.6 g, 34 mmol), and DMF (150 ml) were added, followed by diisopropylcarbodiimide (DICI) (5.3 ml, 34 mmol). The mixture was agitated overnight, filtered, washed (DMF, three times with 200 ml; tetrahydrofuran, three times with 200 ml; MeOH, three times with 200 ml), and dried over $P_2O_5$. The substitution level of the resin was 0.58 mmol/g (>95%) as determined by Fmoc analysis.

P1-Diverse Library Synthesis

Individual P1-substituted Fmoc-amino acid ACC-resin (~25 mg, 0.013 mmol) was added to wells of a MultiChem 96-well reaction apparatus. The resin-containing wells were solvated with DMF (0.5 ml). After filtration, 20% piperidine in DMF solution 30 (0.5 ml) was added, followed by agitation for 30 min. The wells of the reaction block were filtered and washed with DMF (three times with 0.5 ml). To introduce the randomized P2 position, an isokinetic mixture of Fmoc-amino acids [4.8 mmol, 10 eq per well; Fmoc-amino acid, mol %: Fmoc-Ala-OH, 3.4; Fmoc-Arg(Pbf)-OH, 6.5; Fmoc-Asn(Trt)-OH, 5.3; Fmoc-Asp(O-t-Bu)-OH, 3.5; Fmoc-Glu (O-t-Bu)-OH, 3.6; Fmoc-Gln(Trt)-OH, 5.3; Fmoc-Gly-OH, 2.9; Fmoc-His(Trt)-OH, 3.5; Fmoc-Ile-OH, 17.4; Fmoc-Leu-OH, 4.9; Fmoc-Lys(Boc)-OH, 6.2; Fmoc-Nle-OH, 3.8; Fmoc-Phe-OH, 2.5; Fmoc-Pro-OH, 4.3; Fmoc-Ser(O-t-Bu)-OH, 2.8; Fmoc-Thr(O-t-Bu)-OH, 4.8; Fmoc-Trp(Boc)-OH, 3.8; Fmoc-Tyr(O-t-Bu)-OH, 4.1; Fmoc-Val-OH, 11.3] was preactivated with DICI (390 μl, 2.5 mmol), and HOBt (340 mg, 2.5 mmol) in DMF (10 ml). The solution (0.5 ml) was added to each of the wells. The reaction block was agitated for 3 h, filtered, and washed with DMF (three times with 0.5 ml). The randomized P3 and P4 positions were incorporated in the same manner. The Fmoc of the P4 amino acid was removed and the resin was washed with DMF (three times with 0.5 ml) and treated with 0.5 ml of a capping solution of AcOH (150 μl, 2.5 mmol), HOBt (340 mg, 2.5 mmol), and DICI (390 μl, 2.5 mmol) in DMF (10 ml). After 4 h of agitation, the resin was washed with DMF (three times with 0.5 ml) and $CH_2Cl_2$ (three times with 0.5 ml), and treated with a solution of 95:2.5:2.5 TFA/TIS/$H_2O$. After incubation for 1 h the reaction block was opened and placed on a 96-deep-well titer plate and the wells were washed with additional cleavage solution (twice with 0.5 ml). The collection plate was concentrated, and the material in the substrate-containing wells was diluted with EtOH (0.5 ml) and concentrated twice. The contents of the individual wells were lyophilized from $CH_3CN/H_2O$ mixtures. The total amount of substrate in each well was conservatively estimated to be 0.0063 mmol (50%) on the basis of yields of single substrates.

Screening Methods Using Both Libraries

Multigram quantities of P1-substituted ACC-resin can be synthesized by the methods described. Fmoc-amino acid-substituted ACC resin was placed in 57 wells of a 96-well reaction block: sub-libraries were denoted by the second fixed position (P4, P3, P2) of 19 amino acids (cysteine was omitted and norleucine was substituted for methionine). Synthesis, capping, and cleavage of the substrates were identical to those described in the previous section, with the exception that for P2, P3, and P4 sub-libraries, individual amino acids (5 eq of Fmoc-amino acid monomer, 5 eq of DICI, and 5 eq of HOBt in DMF), rather than isokinetic mixtures, were incorporated in the spatially addressed P2, P3, or P4 positions.

Preparation of the complete diverse and P1-fixed combinatorial libraries was carried out as described above. The library was aliquoted into 96-well plates to a final concentration of 250 μM. Variant proteases were diluted in MTSP activity buffer (50 mM Na Hepes, pH 8.0, 100 mM NaCl, 0.01% Tween-20) to concentrations between 50 nM and 1 μM. Initial activity against Ac-QGR-AMC was used to adjust the variant protease concentration to one approximately equal to 50 nM wild type rat MT-SP1. Enzymatic activity in the P1-Arg library was assayed for one hour at 30° C. on a Spectra-Max Delta flourimeter (Molecular Devices). Excitation and emission were measured at 380 nm and 460 nm, respectively.

Synthesis and Fluorescence Screening of Libraries.

P1-Diverse Library

A(i). Synthesis

P1-diverse libraries were synthesized as provided above. The specificity of the various MT-SP1 muteins were characterized as compared to wild-type MT-SP1.

A(ii). Enzymatic Assay of Library

The concentration of proteolytic enzymes was determined by absorbance measured at 280 nm (Gill, S. C., et al., (1989) Anal Biochem 182:319-26). The proportion of catalytically active thrombin, plasmin, trypsin, uPA, tPA, and chymotrypsin was quantitated by active-site titration with MUGB or MUTMAC (Jameson, G. W., et al., (1973) Biochemical Journal 131:107-117).

Substrates from the PSSCLs were dissolved in DMSO. Approximately $1.0 \times 10^{-9}$ mol of each P1-Lys, P1-Arg, or P1-Leu sub-library (361 compounds) was added to 57 wells of a 96-well microfluor plate (Dynex Technologies, Chantilly, Va.) for a final concentration of 0.1 μM. Approximately $1.0 \times 10^{-10}$ mol of each P1-diverse sub-library (6859 compounds) was added to 20 wells of a 96-well plate for a final concentration of 0.01 μM in each compound. Hydrolysis reactions were initiated by the addition of enzyme (0.02 nM-100 nM) and monitored fluorimetrically with a Perkin Elmer LS50B Luminescence Spectrometer, with excitation at 380 nm and emission at 450 nm or 460 nm. Assays of the serine proteases were performed at 25° C. in a buffer containing 50 mM Tris, pH 8.0, 100 mM NaCl, 0.5 mM CaCl$_2$, 0.01% Tween-20, and 1% DMSO (from substrates). Assay of the cysteine proteases, papain and cruzain, was performed at 25° C. in a buffer containing 100 mM sodium acetate, pH 5.5, 100 mM NaCl, 5 mM DTT, 1 mM EDTA, 0.01% Brij-35, and 1% DMSO (from substrates).

B. Profiling Proteases with a P1-Diverse Library of 137, 180 Substrate Sequences To test the possibility of attaching all amino acids to the P1-site in the substrate sequence a P1-diverse tetrapeptide library was created. The P1-diverse library consists of 20 wells in which only the P1-position is systematically held constant as all amino acids, excluding cysteine and including norleucine. The P2, P3, and P4 positions consist of an equimolar mixture of all amino acids for a total of 6,859 substrate sequences per well. Several serine and cysteine proteases were profiled to test the applicability of this library for the identification of the optimal P1 amino acid. Chymotrypsin showed the expected specificity for large hydrophobic amino acids. Trypsin and thrombin showed preference for P1-basic amino acids (Arg>Lys). Plasmin also showed a preference for basic amino acids (Lys>Arg). Granzyme B, the only known mammalian serine protease to have P1-Asp specificity, showed a distinct preference for aspartic acid over all other amino acids, including the other acidic amino acid, Glu. The P1-profile for human neutrophil elastase has the canonical preference for alanine and valine. The cysteine proteases, papain and cruzain showed the broad P1-substrate sequence specificity that is known for these enzymes, although there is a modest preference for arginine. The MT-SP1 wild type protease preferred Arg or Lys.

C. Profiling MT-SP1 Proteases with the P1-Constant Library

A P1-constant tetrapeptide library is created as disclosed above. The P1-constant library consists of 20 wells in which only the P1-position is systematically held constant as all amino acids, excluding cysteine and including norleucine. The P2, P3, and P4 positions consist of an equimolar mixture of all amino acids for a total of 6,859 substrate sequences per well. Several serine and cysteine proteases were profiled to test the applicability of this library for the identification of the optimal P1 amino acid. MT-SP1 prefers the amino acids Arg and Lys at P1.

Example 4

Determination of the Extended Specificity of MT-SP1 Variants by PSSCL

The P1-Arg fixed PSSCL library is resuspended in DMSO and arrayed in opaque black 96-well plates at a concentration of 5-10 nanomoles per well. Variant proteases are diluted into 50 mM Tris pH 8, 50 mM NaCl, and 0.01% Tween 20 (MTSP activation buffer) at a concentration of 5 nM to 5 µM. One hundred microliters of the protease solution is added to each well and fluorescence of the ACC leaving group is measured by excitation at 380 nm and emission at 460 nm using a Spectramax fluorescent plate reader (Molecular Devices). The specificity of variant proteases at each of the P4-P2 extended subsites is determined by the fluorescence of each of the arrayed amino acids in the P4-P2 PSSC libraries.

Figure 2A:
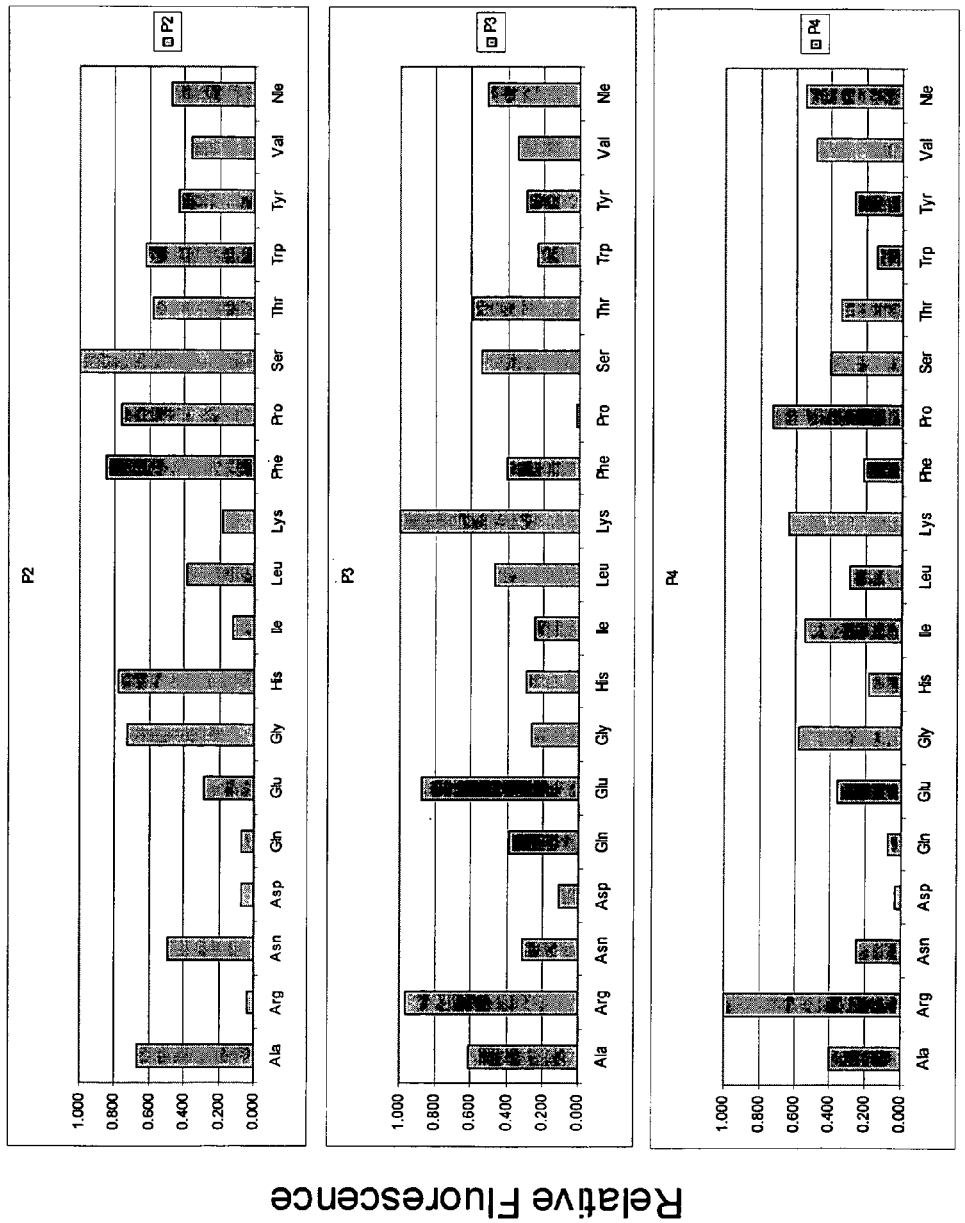
FIG. 2A-H are graphical representations of PSSCL profiles of wild type MT-SP1 and six variants. The MT-SP1 profile (FIG. 2A) shows that its specificity is somewhat broad, such that a variety of amino acids will be accepted in the P4 and P3 positions in addition to Arg or Lys.
Figure 2B:
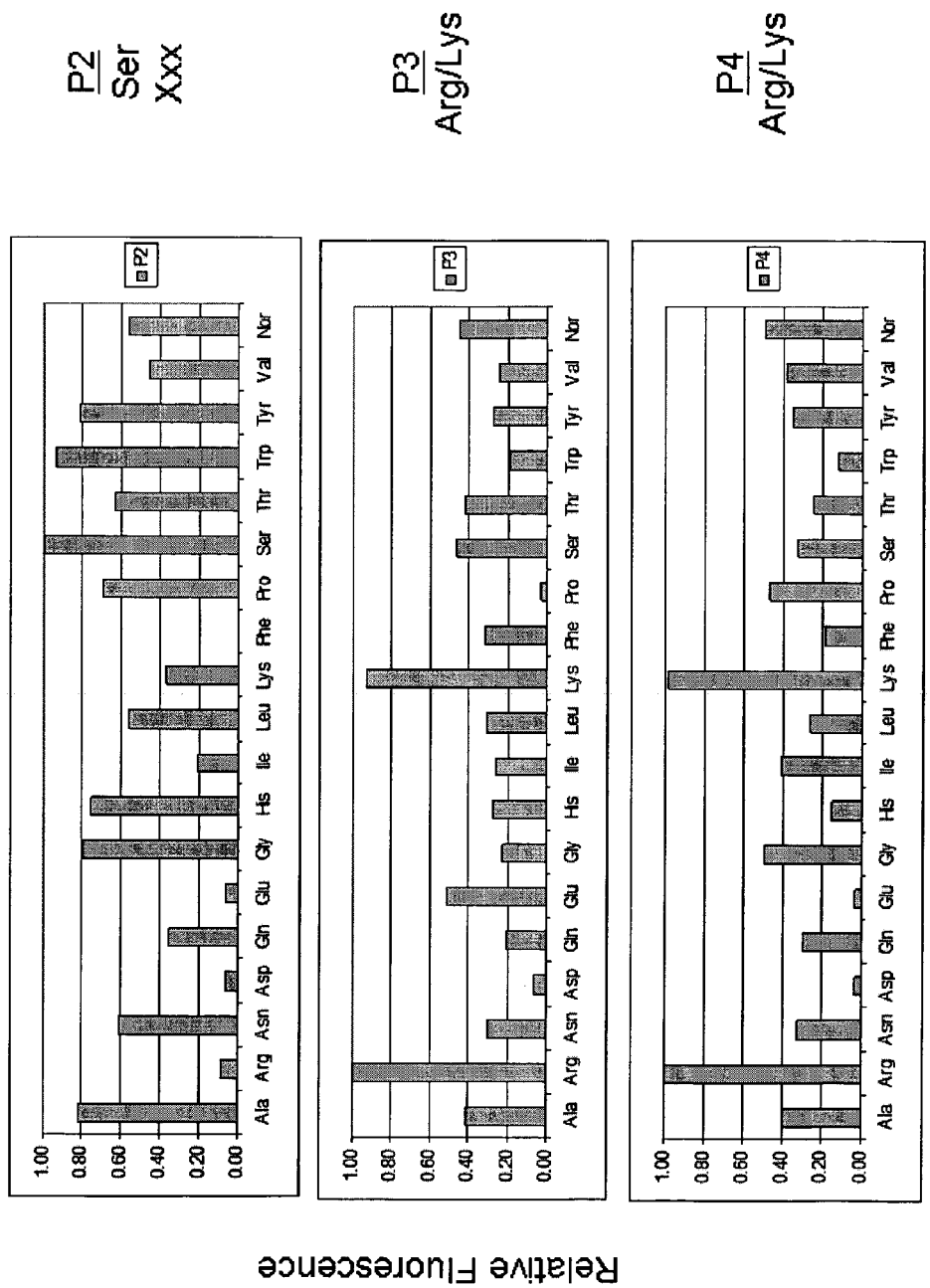

Result. Screening by PSSCL confirms that wildtype MT-SP1 has a preference for basic (Arg, Lys) at the P4 and P3 positions, in agreement with published data by Takeuchi et al., J. Biol. Chem., Vol. 275, Issue 34, 26333-26342, Aug. 25, 2000. However, the PSSCL profile also reveals that its specificity is somewhat broad, such that a variety of amino acids will be accepted in the P4 and P3 positions in addition to Arg or Lys (FIG. 2A). A number of mutants were generated (see above) to narrow the substrate specificity and to direct it towards potential cleavage sites identified in the VEGF receptor (see below). One mutant, L172D (CB18), shows a very narrow specificity profile, such that Arg or Lys is strongly preferred over any other amino acid in the P4 and P3 positions (FIG. 2B). A potential cleavage sequence has been identified in VEGFR2 (RRVR) that closely matches the specificity profile for L172D (RRXR). Variants of MT-SP1 have been profiled with the P1-Arg PSSCL (for specific variants, see Table 11). All variants show an increase in selectivity at one or more substrate sequence positions. Representative profiles are shown in FIGS. 2A through H.

Example 5

Selection of MT-SP1 Variants Capable of Peptide Sequence Specific Target Cleavage Using Protease Phage Display The phagemid is constructed such that it (i) carries all the genes necessary for M13 phage morphogenesis; (ii) it carries a packaging signal which interacts with the phage origin of replication to initiate production of single-stranded DNA; (iii) it carries a disrupted phage origin of replication; and (iv) it carries an ampicillin resistance gene.

The combination of an inefficient phage origin of replication and an intact plasmid origin of replication favors propagation of the vector in the host bacterium as a plasmid (as RF, replicating form, DNA) rather than as a phage. It can therefore be maintained without killing the host. Furthermore, possession of a plasmid origin means that it can replicate independent of the efficient phage-like propagation of the phagemid. By virtue of the ampicillin resistance gene, the vector can be amplified, which in turn increases packaging of phagemid DNA into phage particles.

Fusion of the MT-SP1 variant gene to either the gene 3 or gene 8 M13 coat proteins can be constructed using standard cloning methods. (Sidhu, Methods in Enzymology, 2000, V328, p 333). A combinatorial library of variants within the gene encoding MT-SP1 is then displayed on the surface of M13 as a fusion to the p3 or p8 M13 coat proteins and panned against an immobilized, aldehyde-containing peptide corresponding to the target cleavage of interest. The aldehyde moiety will inhibit the ability of the protease to cleave the scissile bond of the protease, however, this moiety does not interfere with protease recognition of the peptide. Variant protease-displayed phage with specificity for the immobilized target peptide will bind to target peptide coated plates, whereas non-specific phage will be washed away. Through consecutive rounds of panning, proteases with enhanced specificity towards the target sequence can be isolated. The target sequence can then be synthesized without the aldehyde and isolated phage can be tested for specific hydrolysis of the peptide.

Example 6

Identification of MT-SP1 Mutein Cleavage in the Stalk Region of VEGFR2

The polypeptide sequence of VEGF receptor 2 (VEGF-R2/KDR), showing the respective sequences of the extracellular (SEQ ID NO:8) and intracellular (SEQ ID NO:9) domains, is provided in Table 12. Sequences that closely match the P4-P1 native substrate specificity of MT-SP1 are shown in bold. Two sequences match the recognition profile of both L172D and wild-type MT-SP1: the boxed sequence RVRK (SEQ ID NO: 13) and the double underlined sequence RRVR (SEQ ID NO: 14).

L172D cleaves full-length VEGFR2 but at a reduced rate compared to the wild-type. Several mutants (Q175D and D217F) cleave the receptor with higher efficiency than wild-type. None of the protease variants or wild-type cleave the Fc domain.

TABLE 12

VEGFR2/KDR Substrate Specificity of Targeted MT-SP1 Proteases

Extra-cellular
KQSKVLLAVALWLCVETRAASVGLPSVSLDLPRLSIQKDILTIKANTTLQITCRGQRDLD
WLWPNNQSGSEQRVEVTECSDGLFCKTLTIPKVIGNDTGAYKCFYRETDLASVIYVYVQD
YRSPFIASVSDQHGVVYITENKNKTVVIPCLGSISNLNVSLCARYPEKRFVPDGNRISWD
SKKGFTIPSYMISYAGMVFCEAKINDESYQSIMYIVVVVGYRIYDVVLSPSHGIELSVGE
KLVLNCTARTELNVGIDFNWEYPSSKHQHKKLVNRDLKTQSGSEMKKFLSTLTIDGVTRS
DQGLYTCAASSGLMTKKNSTFVRVHEKPFVAFGSGMESLVEATVGERVRIPAKYLGYPPP
EIKWYKNGIPLESNHTIKAGHVLTIMEVSERDTGNYTVILTNPISKEKQSHVVSLVVYVP
PQIGEKSLISPVDSYQYGTTQTLTCTVYAIPPPHHIHWYWQLEECANEPSQAVSVTNPY
PCEEWRSVEDFQGGNKIEVNKNQFALIEGKNKTVSTLVIQAANSALYKCEAVNKVGRGE
RVISFHVTRGPEITLQPDMQPTEQESVSLWCTADRSTFENLTWYKLGPQPLPIHVGELPT
PVCKNLDTLWKLNATMFSNSTNDILIMELKNASLQDQGDYVCLAQDRKTKKRHCVVRQLT
VLERV<u>APTIT</u>GNLENQTTSIGESIEVSCTASGNPPPQIMWFKDNETLVEDSGIVLKDGNR
NLTIR│RVRK│EDEGLYTCQACSVLGCAKVEAFFIIEGAQEKTNLE (SEQ ID NO: 8)

Intra-cellular
IIILVGTAVIAMFFWLLLVIILRTVKRANGGELKTGYLSIVMDPDELPLDEHCERLPYDA
SKWEFPRDRLKLGKPLGRGAFGQVIEADAFGIDKTATCRTVAVKMLKEGATHSEHRALMS
ELKILIHIGHHLNVVNLLGACTKPGGPLMVIVEFCKFGNLSTYLRSKRNEFVPYKTKGAR
FRQGKDYVGAIPVDLKRRLDSITSSQSSASSGFVEEKSLSDVEEEEAPEDLYKDFLTLEH
LICYSFQVAKGMEFLASRKCIHRDLAARNILLSEKNVVKICDFGLARDIYKDPDYVRKGD
ARLPLKWMAPETIFDRVYTIQSDVWSFGVLLWEIFSLGASPYPGVKIDEEFCRRLKEGTR
MRAPDYTTPEMYQTMLDCWHGEPSQRPTFSELVEHLGNLLQANAQQDGKDYIVLPISETL
SMEEDSGLSLPTSPVSCMEEEEVCDPKFHYDNTAGISQYLQNSKRKSRPVSVKTEDIPL
EEPEVKVIPDDNQTDSGMVLASEELKTLEDRTKLSPSFGGMVPSKSRESVASEGSNQTSG
YQSGYHSDDTDTTVYSSEEAELLKLIEIGVQTGSTAQILQPDSGTTLSSPPV
(SEQ ID NO: 9)

Purified extracellular domain of VEGF-R2 (Flk1) fused to the Fc domain of mouse IgG (2.5 µg) was resuspended with 1 µM MT-SP1 and variant proteases in 17.1 uL of MTSP activation buffer. The reaction was incubated at 37° C. for 2 hours, deglycosylated with PNGaseF, and separated by SDS-PAGE electrophoresis. Full length Flk1-Fc and cleavage products were identified by staining with Coomassie brilliant blue and the N-termini sequenced by the Edman protocol. Purified VEGFR2-Fc is cleaved by wild-type and mutant MT-SP1 at the sequence RRVR (SEQ ID NO: 14)/KEDE (SEQ ID NO: 19) in the extracellular stalk region of the receptor. Thus, the present invention provides proteases that can cleave the VEGFR in the stalk region, and in one embodiment of the invention, such proteases are administered to a patient in need of treatment for cancer, macular degeneration, or another disease in which angiogenesis plays a causative or contributive role.

Example 7

Assaying Cleavage of Purified VEGF Receptor

Purified extracellular domain of VEGF-R2 fused to the Fc domain of mouse IgG (3-10 µg) is resuspended in MTSP activation buffer (20 µL). Variant proteases are added to a final concentration of 100 nM to 1 µM. The reaction is incubated at 37° C. for 1-2 hours and then separated by SDS-PAGE electrophoresis. Bands are visualized by Coomassie blue staining, silver staining, and/or Western blot.

Result. The purified VEGFR2-Fc is efficiently cleaved by wild-type and mutant MT-SP1 (FIG. 3). Cleavage by variant proteases yields cleavage products with apparent molecular weights of ~80 kDa and 30 kDa; analysis of potential cleavage sites in VEGFR2 suggests that MT-SP1 variants target the stalk (membrane proximal) region of VEGFR2. The mutant Example 8

Assaying for Cleavage of VEGF Receptor from Endothelial Cells

Human umbilical vein endothelial cells (HUVECs) were purchased from Cambrex and cultured in EBM-2 (endothelial cell basal medium, Cambrex) with full supplements including 2% fetal calf serum (FCS) and antimycotics-antibiotics. For survival assays, cells were plated at a density of 2×10$^5$ cells/ml in EBM-2 into 96-well plates overnight. The next day, cells were serum-starved by replacing the media with DMEM+10% FCS for 24 hours. Proteases were then added at varying concentrations from 10-1000 nM and the cells were incubated in the presence of the proteases for 2 hours. VEGF was added at a final concentration of 20 ng/mL and the cells were incubated for 72 hours. At the end of the 72 hours, cell count was determined by MTT assay (Sigma) according to the manufacturer's protocol.

To visualize the cleavage of the VEGF receptor from the surface of endothelial cells, cells were grown to ~70% confluence in 24-well plates, at which point the media was removed and 200 uL of DMEM plus 10% FCS was added to each well. Proteases to be tested were added at final concentrations of 100-1000 nM. Cells were incubated in the presence of the proteases for 1-3 hours and the media was removed. Cells were washed with 1 mL ice cold PBS (3 times) and were scraped off the plate using a pipette tip. The resuspended cells were centrifuged at 5000 rpm and the supernatant was removed. The cells were lysed in 50 uL lysis buffer (PBS+0.1% NP40) by three freeze-thaw cycles on dry ice. The cell solution was centrifuged at 15,000 rpm to remove membranes and organelles, and 30 uL of the supernatant was separated by SDS gel electrophoresis. Proteins were transferred to a PVDF membrane and probed with an anti-VEGFR2 antibody recognizing the intracellular domain (Chemicon).

Release of the soluble VEGF receptor from the surface of endothelial cells by proteolytic cleavage was detected using a sandwich ELISA. HUVECs were grown in 24-well plates and treated with proteases as described above. After 3 hours incubation, 100 uL of media was removed and the protease inhibitor Pefabloc (Roche) was added to a final concentration of 1 mg/mL. The media was then added to Maxisorp plates (Nunc) that had been treated with a monoclonal antibody recognizing the extracellular domain of VEGFR2 (MAB3573, R & D Systems, 1:125 dilution in PBS). After 1 hour incubation, the plates were washed with PBS+0.01% Tween 20 (PBST), and were treated with a biotinylated polyclonal antibody also recognizing the extracellular domain (BAF357, R & D Systems, 1:500 dilution). After 1 hour incubation, plates were washed with PBST and then treated with streptavidin conjugated horseradish peroxidase (Upstate). Plates were incubated for 1 hour and then washed with PBST, and developed using TMB substrate (Amersham) according to the manufacturer's protocol.

Results. Wildtype MTSP and the more specific mutants, including CB18, CB83 and CB152, efficiently inhibited VEGF-dependent proliferation of endothelial cells in a dose-dependent manner (FIG. 7A). Consistent with the prediction that the MTSP variants inhibit VEGF-dependent cell proliferation by inactivating the VEGF receptor, FIG. 7B shows that the MTSP variants cleave the VEGF receptor on the surface of endothelial cells. Shown is a Western blot in which HUVECs are incubated with the buffer control or MTSP variants, and then cell extracts are probed with an antibody recognizing the intracellular domain of VEGFR2. Wild-type MTSP and variants cleave the full-length receptor (upper band) to generate a truncated form (lower band). In addition, the extracellular domain (ectodomain) of the cleaved receptor can be detected in the media, as shown by the ELISA in FIG. 7C; the released ectodomain is detectable in samples treated with MTSP and variants, but not in the control.

Example 9

Cornea Micropocket Model

To determine the acute maximum tolerated dose, escalating doses of purified wild-type and variant MTSPs were injected i.v. into C57BL/6 mice. The mice were observed for outward signs of toxicity and death.

For the cornea micropocket assay, C57BL/6 mice are anesthetized with avertin i.p. and the eye was treated with topical proparacaine.HCl (Allergan, Irvine, Calif.). Hydron/sucralfate pellets containing VEGF-A$_{165}$ (100 ug, R & D Systems) were implanted into a corneal micropocket at 1 mm from the limbus of both eyes under an operating microscope (Zeiss) followed by intrastomal linear keratotomy by using a microknife (Medtroni Xomed, Jacksonville, Fla.). A corneal micropocket was dissected toward the limbus with a von Graefe knife #3 (2×30 mm), followed by pellet implantation and application of topical erythromycin. After 8 days, neovascularization is quantitated by using a slit lamp biomicroscope and the formula 2πx(vessel length/10)×(clock hours). P values were determined by using a two-tailed t test assuming unequal variances (Microsoft EXCEL). Varying doses of proteases were injected by i.p. twice a day at 12 hour intervals starting at day 0 until day 7.

Figure 8:
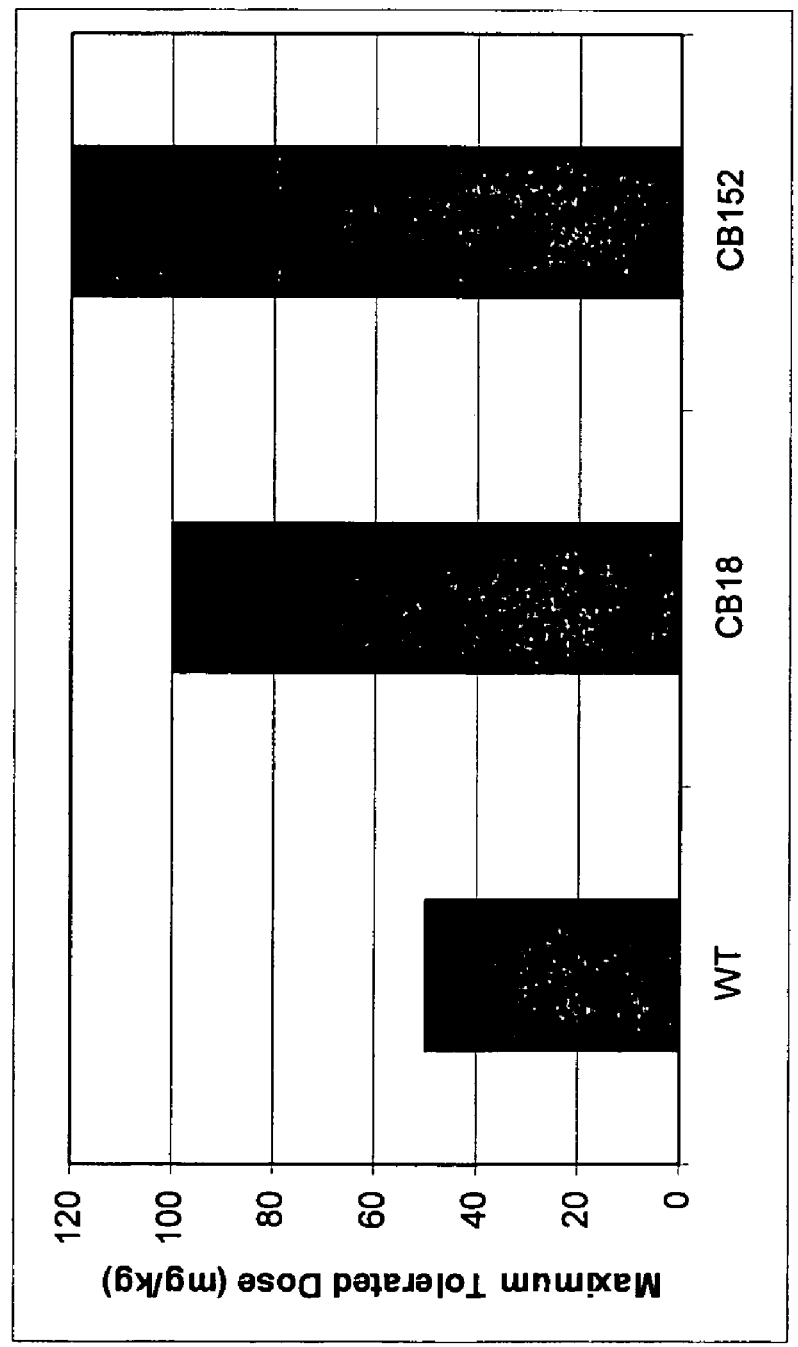
FIG. 8 is a graphical representation of the maximum dose of MT-SP1, CB18 and CB152 that can be tolerated by mice.

Results. Wild-type MT-SP1 was well tolerated by mice, with an acute maximum tolerated dose (MTD) determined to be 50 mg/kg (FIG. 8). Significantly, some of the MT-SP1 variants that were shown to have narrower selectivity in the profiling libraries (see FIG. 2) were better tolerated (i.e. had lower toxicities), resulting in higher maximum tolerated doses. CB18 and CB152, for instance, were tolerated at doses that resulted in death for wild-type MT-SP1. This demonstrates that narrowing the selectivity can be a mechanism for reducing the toxicity of protease drugs.

Figure 9:
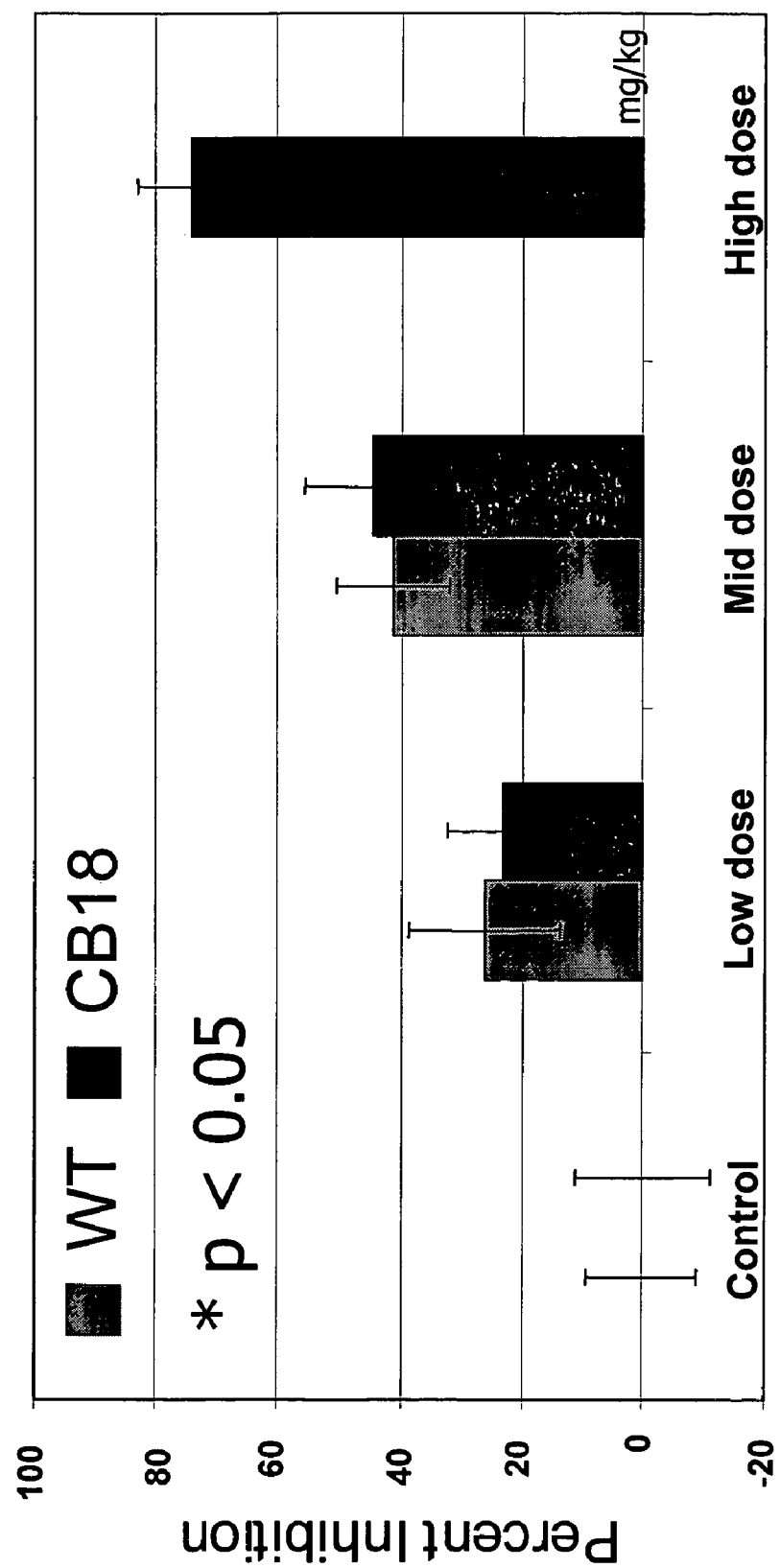
FIG. 9 is a graphical representation of the extent of inhibition of neovascularization by a dose of MT-SP1 and CB18.

Wild-type MT-SP1 and variants were tested for their ability to inhibit VEGF-induced angiogenesis in the mouse cornea micropocket model. As outlined above, a pellet of VEGF was implanted into the cornea of mice, which is normally avascular, and the amount of neovascularization was quantitated after 8 days. When mice were treated with either wild-type or variant MT-SP1, neovascularization was inhibited in a dose dependent manner (FIG. 9). Treatment of mice with wild-type MT-SP1 at the MTD (50 mg/kg) resulted in 42% inhibition of neovascularization. In the case of CB18, it was possible to dose at a higher concentration due to the lower toxicity, and at the higher dose (80 mg/kg) an inhibition of 75% was achieved. Thus, even though wild-type MT-SP1 was effective at inhibiting VEGF-induced angiogenesis, better efficacy was obtained with CB18 due to the fact that it could be dosed at a higher level.

Example 10

Miles Assay for Vascular Permeability

In addition to angiogenesis, VEGF also induces the permeability of blood vessels, resulting in the leakage of fluids into the surrounding tissue. VEGF-induced vascular permeability was measured using the Miles assay. Briefly, nude (athymic) mice were injected with 0.5% Evan's blue dye (100 μL, in PBS, Sigma) by tail vein injection. One hour after dye injection, 100 ng of VEGF in 20 μL PBS was injected intradermally into the back of the mice in duplicate spots. Vascular permeability is visualized by the appearance of blue spots at the site of VEGF injection due to the leakage of the dye. The extent of vascular permeability can be measured semi-quantitatively by measuring the area of the blue spots. To determine if they inhibited vascular permeability, wild-type MT-SP1 and variants were injected i.p. at varying doses immediately after injection of the dye, and the amount of vascular permeability was determined by measuring the area of dye leakage.

Figure 10:
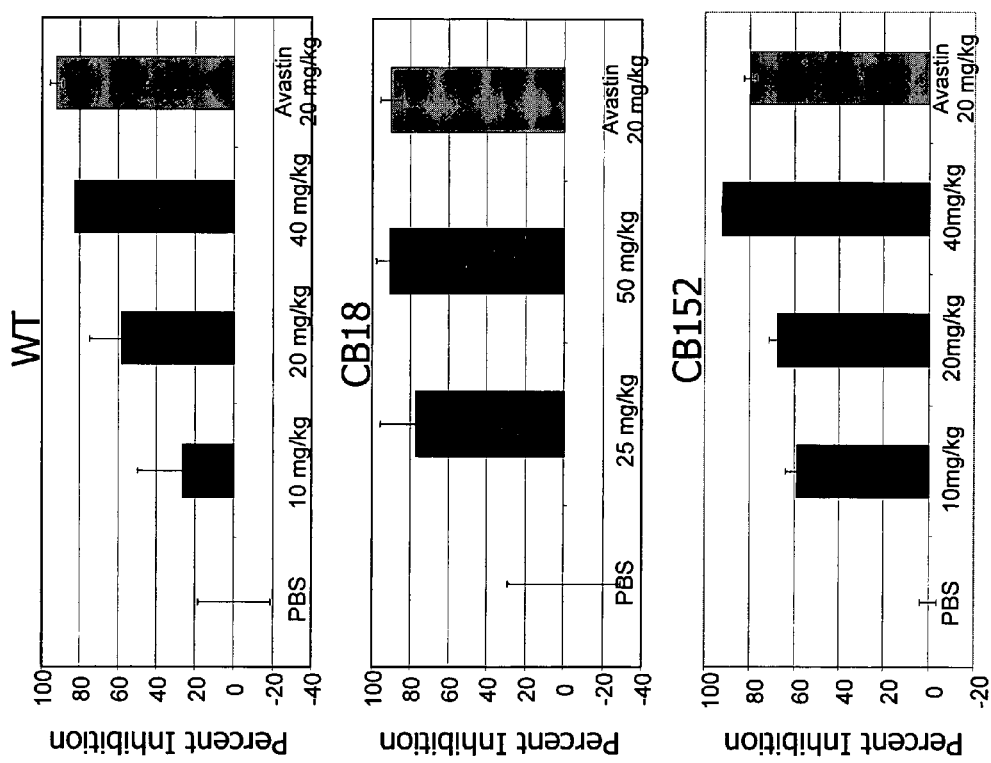
FIG. 10 is a graphical representation of the inhibition of vascular permeability by MT-SP1, CB18 and CB152 in the mouse Miles assay.

Results. Injection of wild-type and variant MT-SP1 resulted in dose-dependent inhibition of vascular permeability (FIG. 10). At the highest dose tested, wild-type MT-SP1 inhibited vascular permeability up to 80%. Similarly, both CB18 and CB152 inhibited vascular permeability, with CB152 showing higher efficacy at the low 10 mg/kg dose than wild-type (60% inhibition for CB152 compared to 25% inhibition for wildtype). At their highest doses, all three proteases had comparable efficacy to AVASTIN™, an anti-VEGF antibody approved for colon cancer.

Example 11

Tumor Xenograft Model

Murine Lewis lung carcinoma (LLC) cells are passaged on the dorsal midline of C57BL/6 mice or in DMEM/10% FCS/penicillin/streptomycin (PNS)/L-glutamine. T241 murine fibrosarcoma is grown in DMEM/10% FCS/PNS/L-glutamine and human pancreatic BxPc3 adenocarcinoma in RPMI medium 1640/10% FCS/PNS. Tumor cells ($10^6$) are injected s.c. into the dorsal midline of C57BL/6 mice (8-10 weeks old) for murine tumors and severe combined immunodeficient (SCID) mice for human tumors, grown to 100-200 mm³ (typically 10-14 days) to demonstrate tumor take, and 10⁹ pfu of protease-encoding adenoviruses or the control adenovirus Ad Fc given by i.v. tail-vein injection. Tumor size in mm³ is calculated by caliper measurements over a 10- to 14-day period by using the formula 0.52×length (mm)×width (mm), using width as the smaller dimension. See, e.g., Kuo et al., PNAS, 2001, 98:4605-4610. P values were determined by using a two-tailed t test assuming unequal variances (Microsoft EXCEL).

Results. Given that cleavage of VEGFR2 will inactivate the receptor, then the systemic delivery of therapeutically effective amounts of protease—either as purified protein or encoded by adenovirus—will result in inhibition of LLC tumor growth. Failure to inhibit tumor growth may be due to the inactivation of the protease by endogenous protease inhibitors (serpins). In such an event, the covalent binding of the serpin to the protease will be detectable as an increase in size of the protease by SDS-PAGE. Mutations can be made in the protease that will make it resistant to serpin inactivation.

Example 12

VEGFR Cleavage

As shown in FIG. 1, scaffold proteases and variants have been successfully expressed as active proteases in yeast or bacterial expression systems at multi-milligram quantities. See, e.g., protocols described in Harris 1998 and Takeuchi, 2000. MT-SP1 was engineered to obtain muteins that selectively cleave Flk-1/KDR.

Additional MT-SP1 muteins, shown in Table 11, were cloned and expressed as described above. As shown in FIG. 1, MT-SP1 variants were expressed in bacteria and purified from inclusion bodies. Each protease retains high catalytic activity and is >99% pure making them appropriate for crystallographic studies.

Table 13 depicts the potential target cleavage sequences for wild-type and mutein MT-SP1. In the table, "Hyd" represents any hydrophobic amino acid (i.e. glycine, alanine, valine, leucine, isoleucine, phenylalanine, tyrosine, or tryptophan), and "Xxx" represents any amino acid.

TABLE 13

Potential MT-SP1 Cleavage Sequences

| | P4 | | P3 | | P2 | | P1 | SEQ ID NO |
|---|---|---|---|---|---|---|---|---|
| MT-SP1 | | | | | | | | |
| Native specificity | K/R | — | Hyd | — | Xxx | — | K/R | 10 |
| | Hyd | — | K/R | — | Xxx | — | K/R | 11 |
| VEGFR2 sequences | K | — | V | — | G | — | R | 12 |
| | R | — | V | — | R | — | K | 13 |
| | R | — | R | — | V | — | R | 14 |
| | R | — | K | — | T | — | K | 15 |
| | K | — | T | — | K | — | K | 16 |
| | T | — | K | — | K | — | R | 17 |

Example 13

Figure 2C:
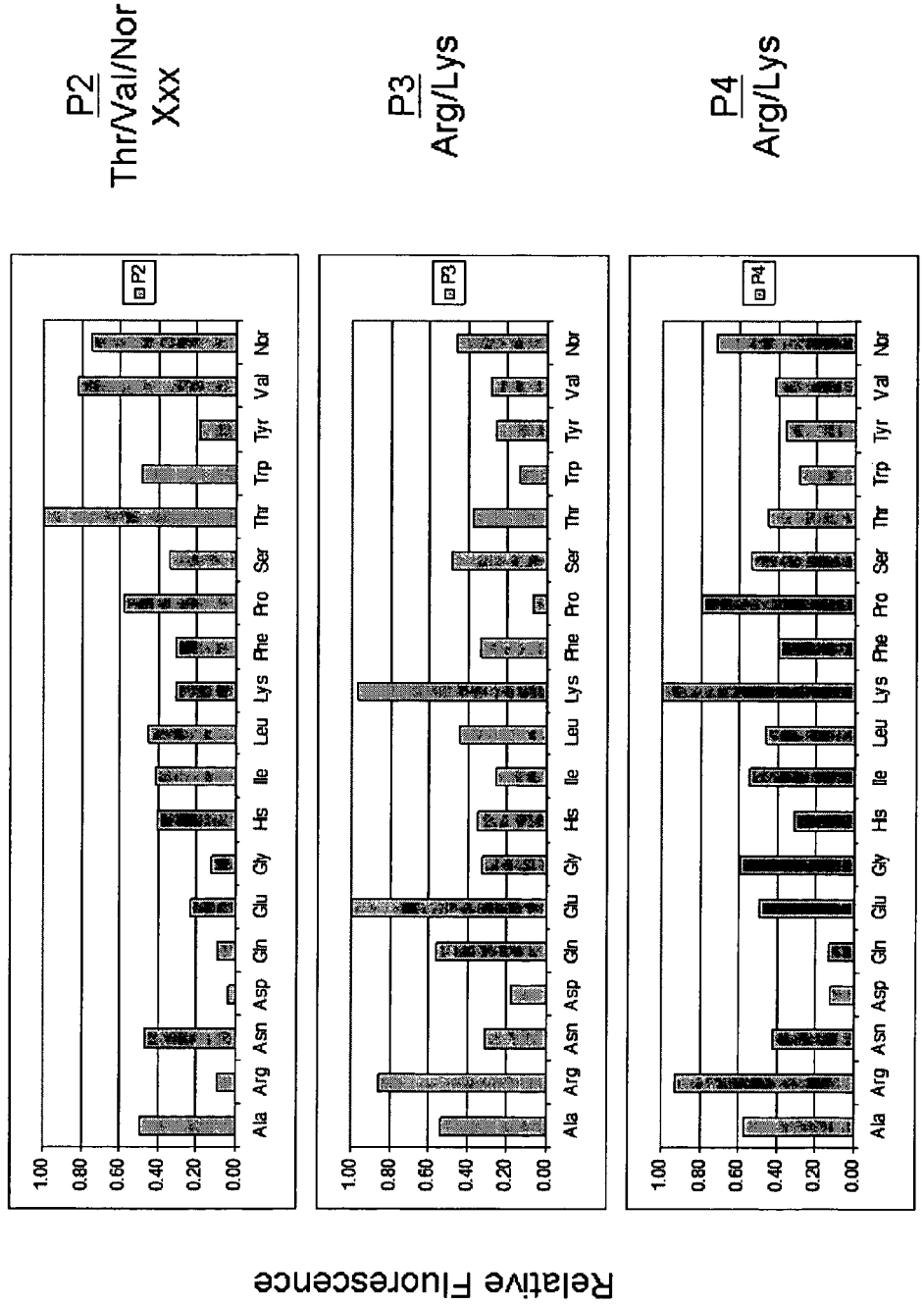
Figure 2D:
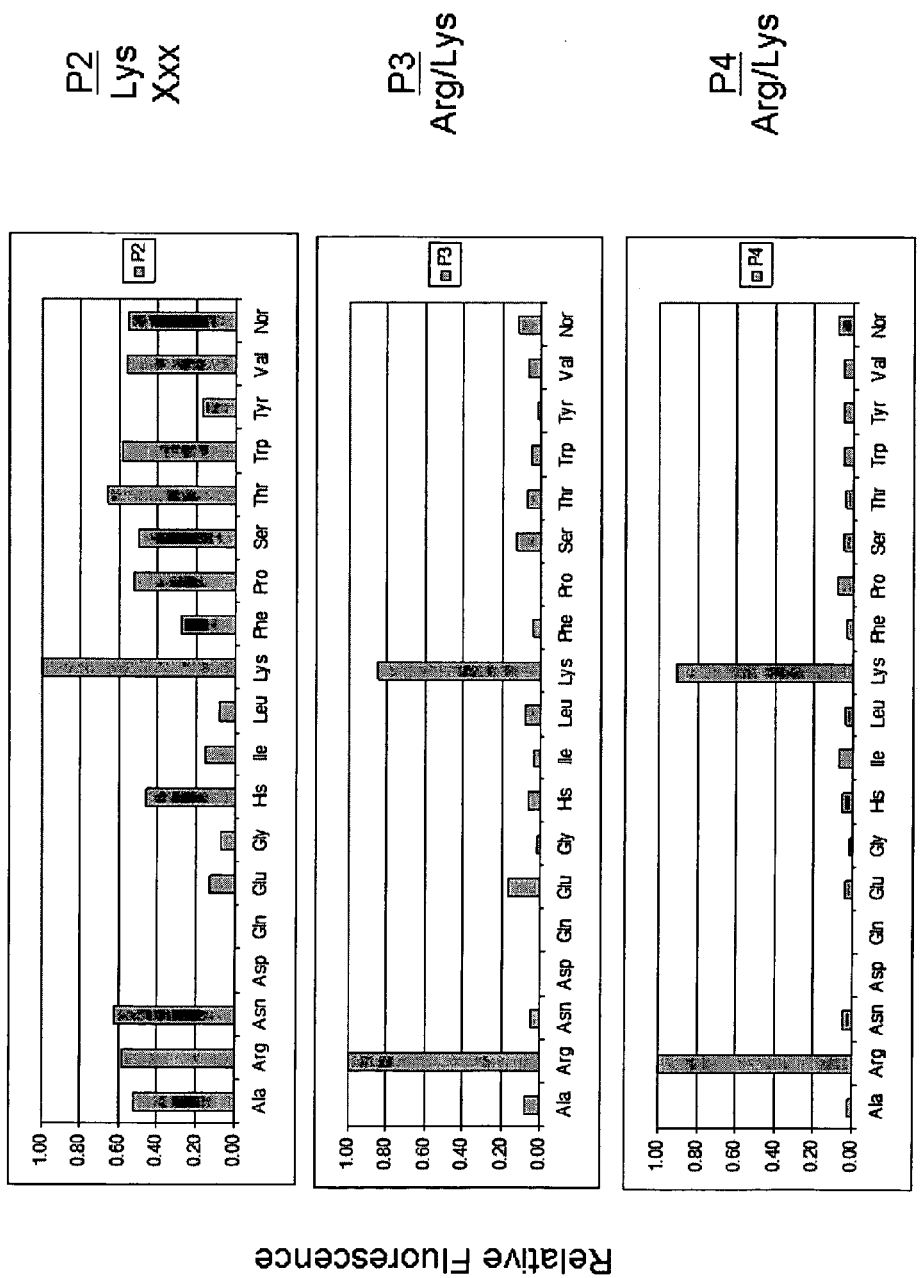

Muteins Consisting of One, Two and Three Mutations with Increased Selectivity Towards VEGFR Stalk Region Sequence, RRVR Multiple muteins were characterized by PSSCL profiling showing increased selectivity towards the RRVR (SEQ ID NO: 14) target cleavage sequence (FIGS. 2A-H). They were grouped into two sub-classes based on which subsite profile was most affected by the mutation: P2 or P3&P4. Mutations of Phe99 to Ala, Ile, and Val increased the protease's P2 selectivity towards Val, and reduced the specificity of Ala containing substrates. This effect is seen in the variants F99V MT-SP1 (CB38), and F99I/L172D/Q175D MT-SP1 (CB159) (FIGS. 2C&D). Mutations such as Phe99 to Trp, Asn, Asp, Ala, or Arg increased the P2 selectivity for Ala, Ser, Trp, Lys and Ile containing substrates. Additional mutations that affected the P2 selectivity were Met180 to Glu and Ala and Trp215 to Tyr and Phe.

Figure 2E:
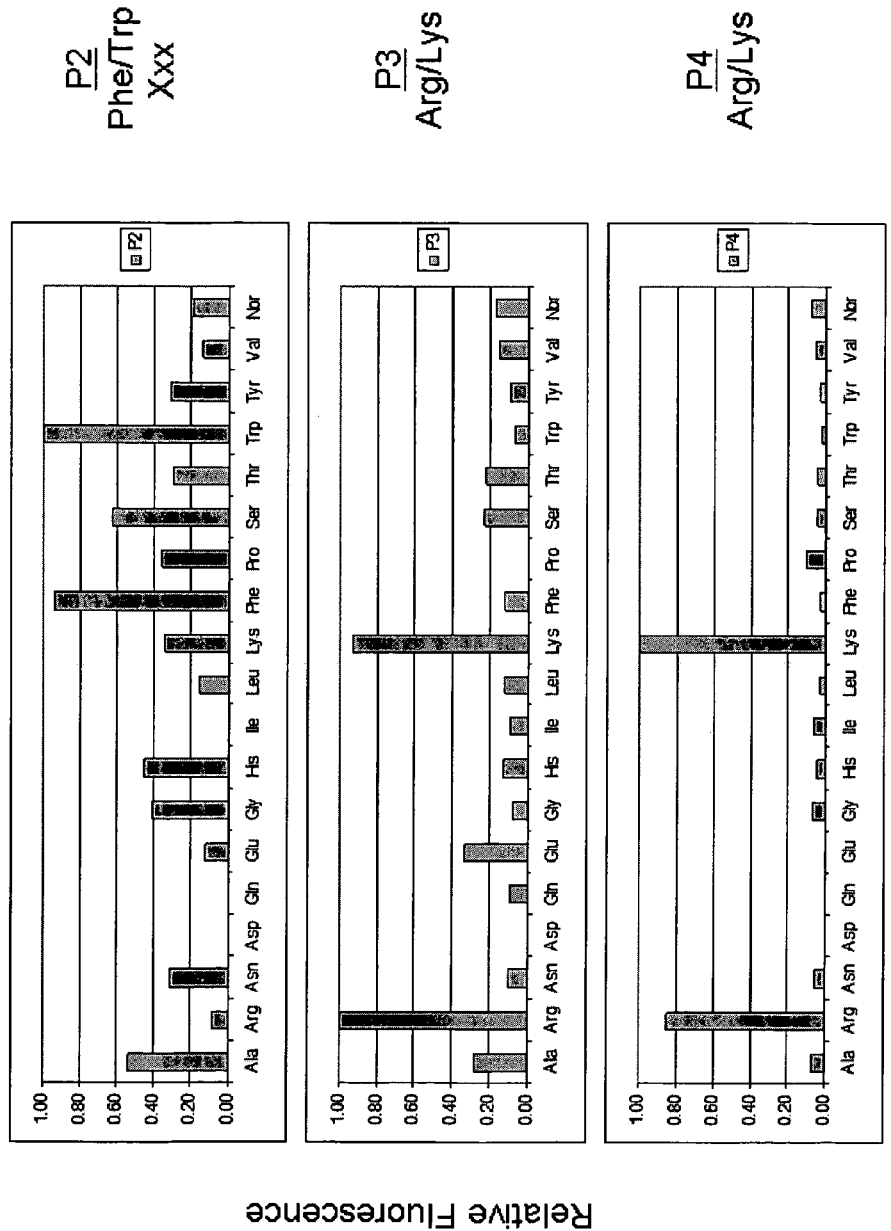
Figure 2F:
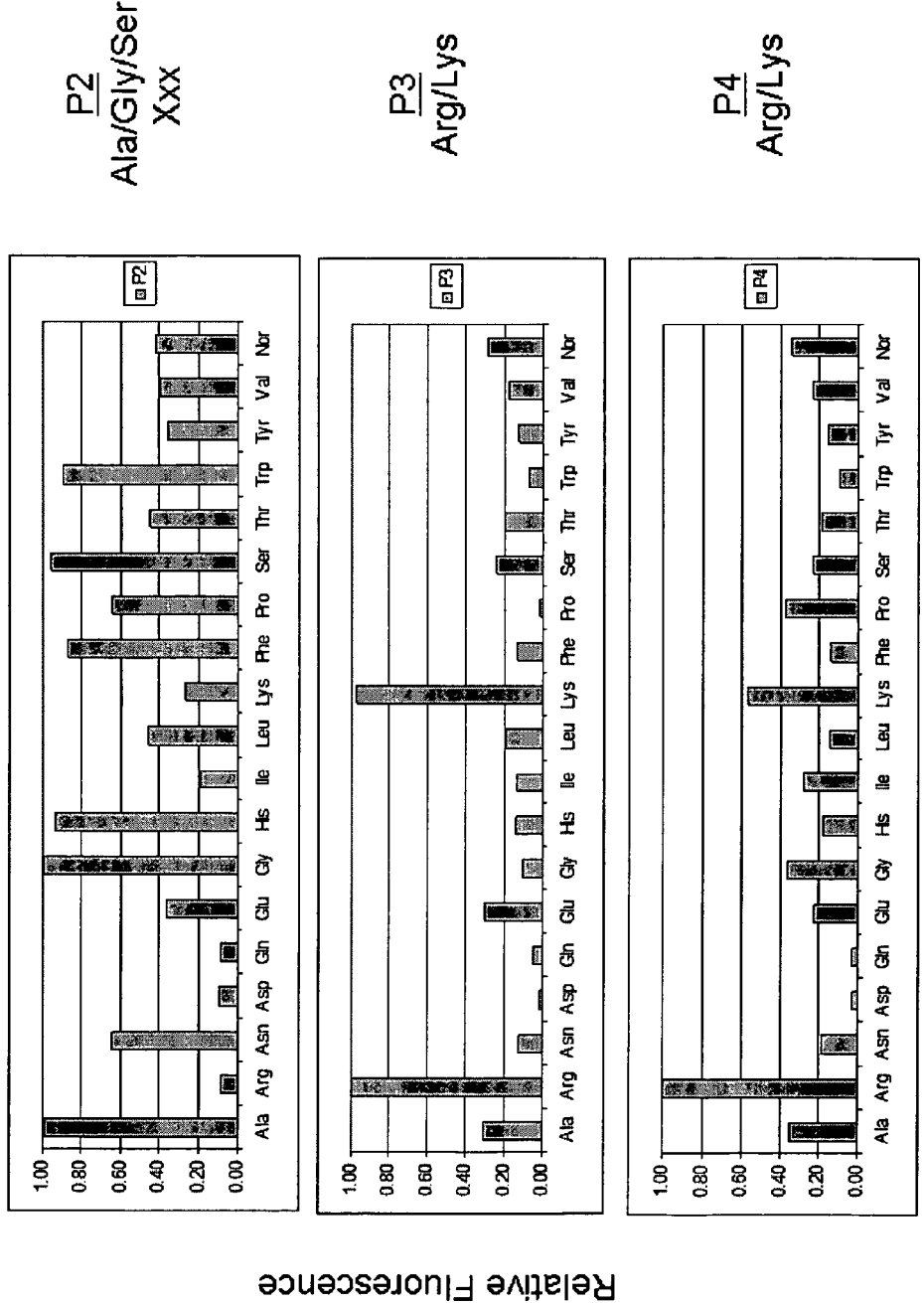

Mutation of Gln192 to Arg and Glu altered the P3 selectivity alone. Mutations at Tyr 146 (Asp), Leu172 (Asp), Gln175 (Asp), Lys224 (Phe), and Met180 (Glu) increased the selectivity of the variants towards both P3 and P4 Arg and Lys containing substrates as in variant L172D (CB18) (FIG. 2B). Grouping these individual mutations together resulted in variant proteases with highly selective P3 and P4 profiles, such as the variants L172D/Q175D (CB83) and Y146D/K224F (CB155) (FIGS. 2E&F).

Figure 2G:
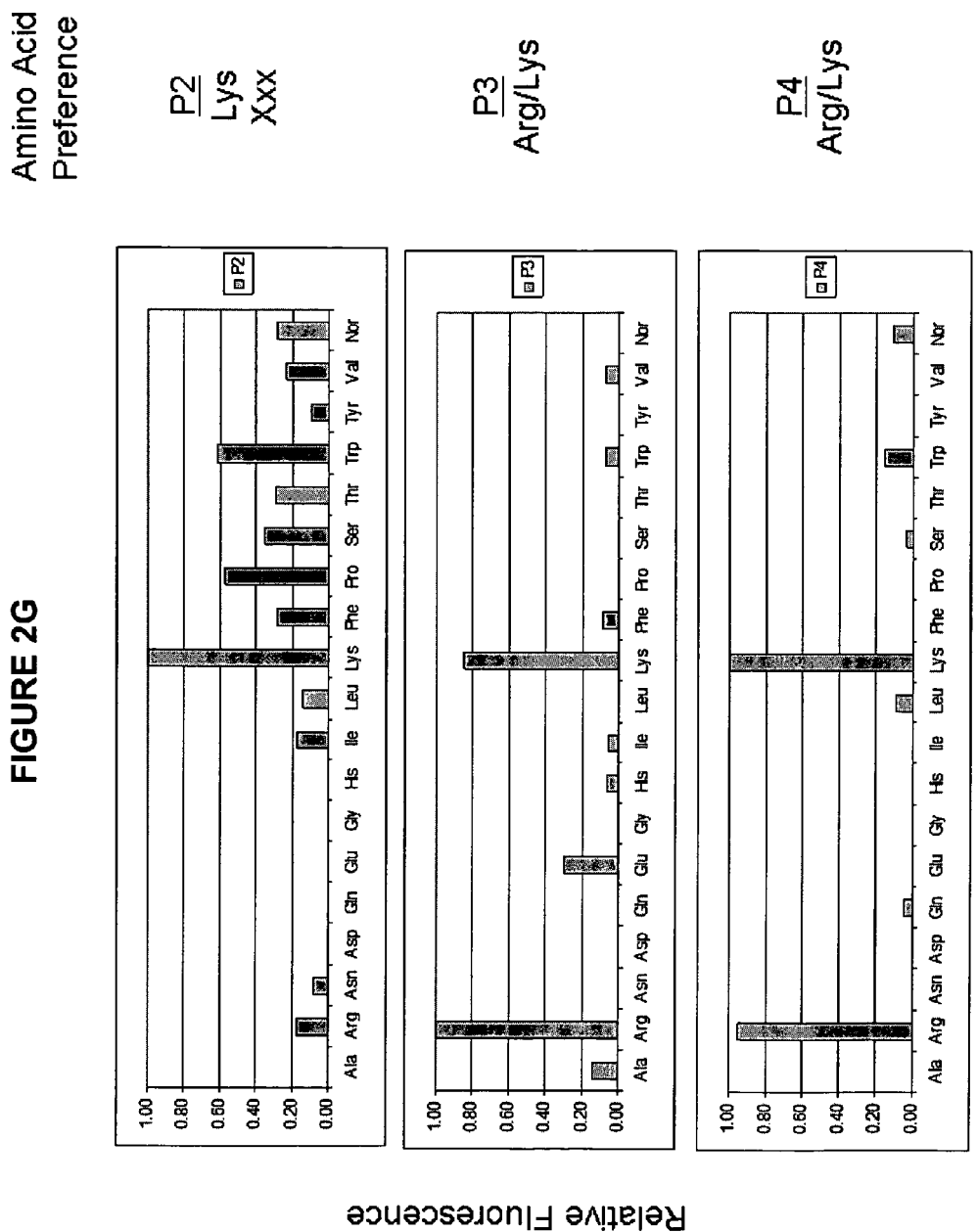
Figure 2H:
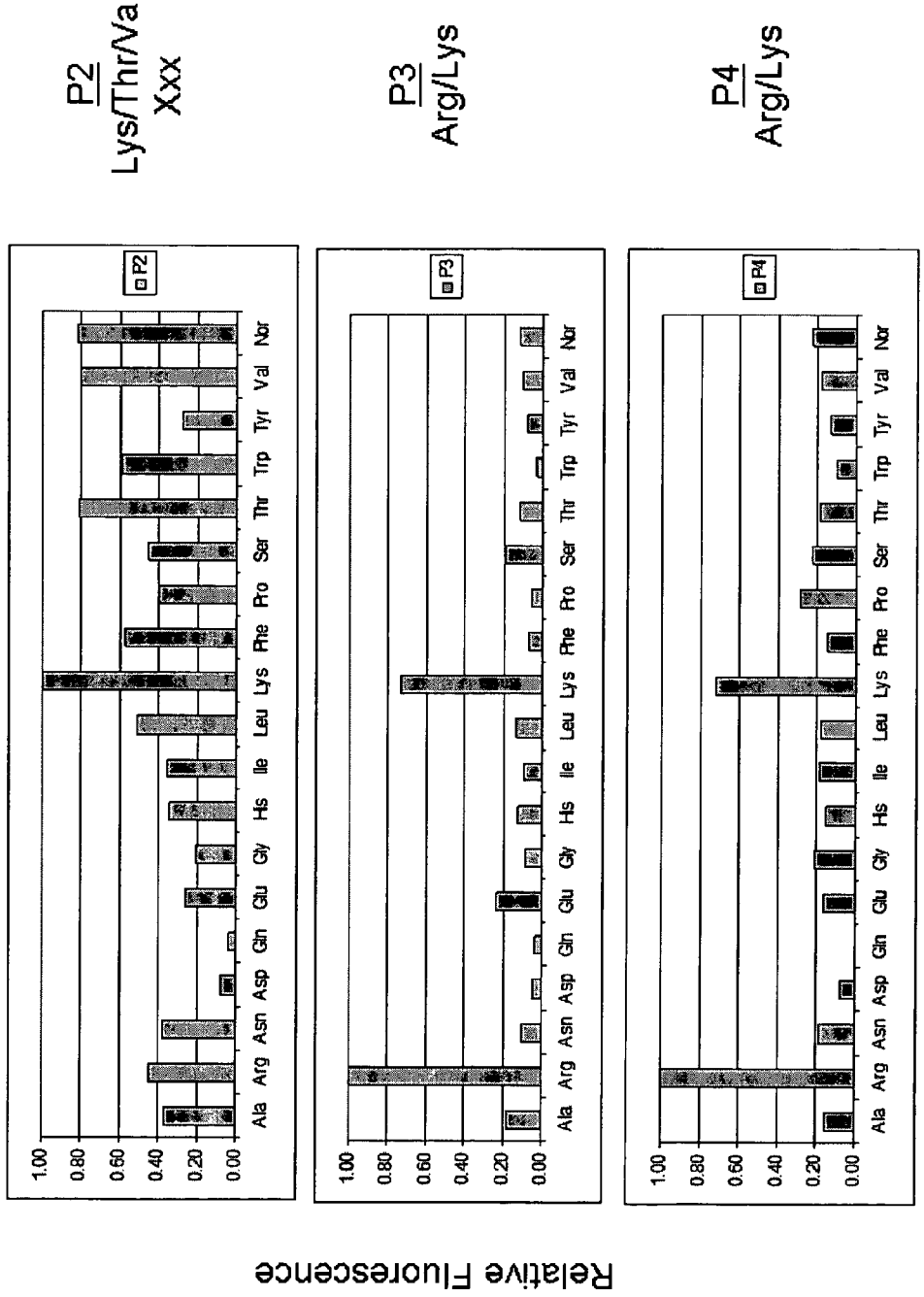

Results. By grouping mutations identified individually to narrow the protease selectivity at P2 and at P3/P4, multiple variants were made that had greater than four fold selectivity towards Arg and Lys residues at the P3 and P4 positions, and altered P2 specificity. Two variants F99V/L172D/Q175D (CB151) and F99V/K224F (CB152) are at least 3 fold more selective of Arg and Lys than other amino acids at the P3 and P4 subsites, and twice as selective for Val over Ala at the P2 subsite (FIGS. 2G&H). These characteristics in the PSSCL demonstrate the efficacy of mutations from Table 10 on altering the selectivity of the MT-SP1 protease towards the desired RRVR sequence.

Example 14

Screening for Preferential Cleavage of RRVR Versus RQAR Substrates

Mutant proteases that match the desired specificity profiles, as determined by substrate libraries, were assayed using individual peptide substrates corresponding to the desired cleavage sequence to determine the magnitude of the change in selectivity. Two substrates were designed: Ac-RRVR (SEQ ID NO:14)-AMC and Ac-RQAR (SEQ ID NO: 18)-AMC. The second sequence, RQAR, is a preferred sequence of MT-SP1 as determined by substrate profiling. It also matches the sequence in the full length protease that must be cleaved for protease activation.

Micheallis-Menton kinetic constants were determined by the standard kinetic methods. Briefly, the substrate is diluted in a series of 12 concentrations between 1 mM and 2 µM in 50 µL total volume of MT-SP1 activity buffer in the wells of a Costar 96 well black half-area assay plate. The solution is warmed to 30° C. for five minutes, and 50 µL of a protease solution between 0.1 and 20 nM was added to the wells of the assay. The fluorescence was measured in a fluorescence spectrophotometer (Molecular Devices Gemini XPS) at an excitation wavelength of 380 nm, an emission wavelength of 450 nm and using a cut-off filter ser at 435 nm. The rate of increase in fluorescence was measured over 30 minutes with readings taken at 30 second intervals. The kinetic constants $k_{cat}$, $K_m$ and $k_{cat}/K_m$ were calculated by graphing the inverse of the substrate concentration versus the inverse of the velocity of substrate cleavage, and fitting to the Lineweaver-Burk equation $(1/\text{velocity}=(K_m/V_{max})(1/[S])+1/V_{max}$; where $V_{max}=[E]*k_{cat})$. The specificity constant $(k_{cat}/K_m)$ is a measure of how well a substrate is cut by a particular protease.

Figure 6:
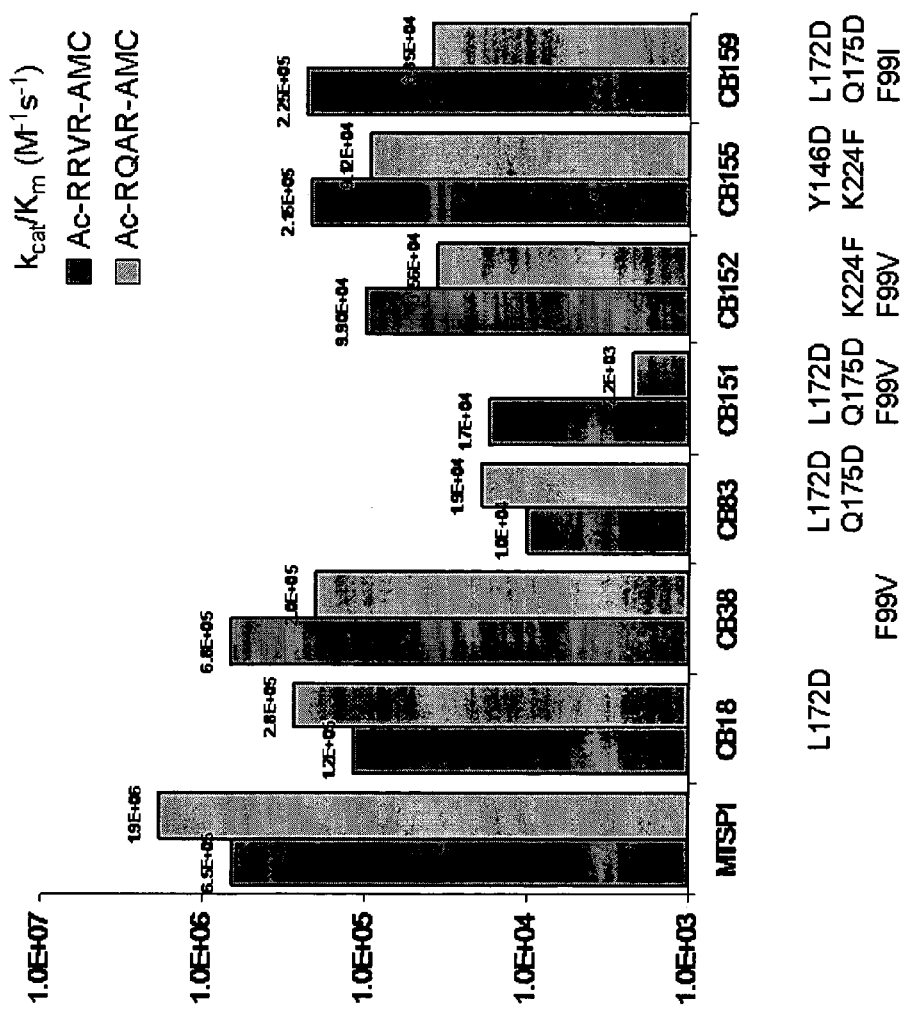
FIG. 6 is a graphical representation of the specificity constants for MT-SP1 and the muteins CB18, CB38, CB83, CB151, CB152, CB155 and CB159 on the tetrapeptide synthetic substrates Ac-RQAR-AMC and Ac-RRVR-AMC. The variants are shown along the x-axis while specificity constants are shown along the y-axis.

Results: The specificity constants (kcat/Km) for wild type MT-SP1 and seven variants (FIG. 6) demonstrate that the semi-quantitative results for relative selectivity between RQAR (SEQ ID NO: 18) and RRVR (SEQ ID NO: 14) derived from the PSSCL are consistent when measured for individual substrates. The wild-type protease, MT-SP1, prefers the RQAR (SEQ ID NO: 18) substrate two times more than the RRVR (SEQ ID NO: 14) substrate. Five of the six variant proteases prefer the target sequence RRVR (SEQ ID NO: 14) over RQAR (SEQ ID NO: 18). Two variants, CB152 and CB159, prefer RRVR (SEQ ID NO: 14) to RQAR (SEQ ID NO: 18) by greater than 8 fold. The only exception is CB38 where the profile suggested that the selectivity was exclusively at the P4 subsite. In addition to the relative preference of RQAR (SEQ ID NO: 18) versus RRVR (SEQ ID NO: 14), individual substrate kinetic measurements define the efficiency of substrate cleavage for each variant. The variants CB155 and CB159 cut the Ac-RRVR (SEQ ID NO: 14)-AMC substrate at 2.2 and 2.3×105 M-1s-1, respectively (FIG. 6). These rates are within 3 fold of the wild type, MT-SP1.

Example 15

Screening for Cleavage of Individual Substrates

Mutant proteases that match the desired specificity profiles, as determined, for example, by substrate libraries, are assayed using individual peptide substrates corresponding to the desired cleavage sequence. Individual kinetic measurements are performed using a Spectra-Max Delta fluorimeter (Molecular Devices). Each protease is diluted to between 50 nM and 1 µM in assay buffer. All ACC substrates are diluted with MeSO to between 5 and 500 µM, while AMC [DEFINED] substrates are diluted to between 20 and 2000 µM. Each assay contains less than 5% MeSO. Enzymatic activity is monitored every 15 seconds at excitation and emission wavelengths of 380 nm and 460 nm, respectively, for a total of 10 minutes. All assays are performed in 1% DMSO.

Example 16

Screening for Cleavage of Full-Length Proteins

Variant proteases are assayed to ascertain that they will cleave the desired sequence when presented in the context of the full-length protein, and the activity of the target protein is assayed to verify that its function has been destroyed by the cleavage event. The cleavage event is monitored by SDS-PAGE after incubating the purified full-length protein with the variant protease. The protein is visualized using standard Coomasie blue staining, by autoradiography using radio labeled protein, or by Western blot using the appropriate antibody. Alternatively, if the target protein is a cell surface receptor, cells expressing the target protein are exposed to the variant protease. The cleavage event is monitored by lysing the cells and then separating the proteins by SDS-PAGE, followed by visualization by Western blot. Alternatively, the soluble receptor released by proteolysis is quantified by ELISA.

Cleavage of VEGF.

Vascular endothelial growth factor (VEGF) is an endothelial cell-specific mitogen normally produced during embryogenesis and adult life. VEGF is a significant mediator of angiogenesis in a variety of normal and pathological processes, including tumor development. Three high affinity cognate receptors to VEGF have been identified: VEGFR-1/Flt-1, VEGFR-2/KDR, and VEGFR-3/Flt-4.

To determine if MT-SP1 cleaves both the signaling molecule in addition to the receptor, a 165 amino acid recombinant version of VEGF, VEGF165, was assayed by SDS-PAGE. VEGF165 was reconstituted in PBS to a concentration of 0.2 µg/µL and diluted to a final concentration of 5 µM. Solutions with no protease and 100 nM MT-SP1 or CB152 were incubated with the VEGF at 37° C. for five hours. The resulting protein cleavage products were deglycosylated, separated by SDS-PAGE, and silver stained (FIG. 11). MT-SP1 efficiently cleaves VEGF165 under the assay conditions while the more selective variant CB152 does not. This result demonstrates that wild-type MT-SP1 can be used to block VEGF signaling through two different mechanisms: cleavage of the mitogen and cleavage of the receptor. CB152, a variant with narrow selectivity to the RRVR (SEQ ID NO: 14) sequence in the stalk region of VEGFR2, does not cleave VEGF, but does cleave VEGFR and can be dosed at higher concentrations due to reduced toxicity.

Cleavage of VEGFR.

$^{125}$I-VEGFR (40,000 cpm) is incubated with varying concentrations of protease, samples are boiled in SDS-PAGE sample buffer and examined on a 12% polyacrylamide gel. The gels are dried and exposed to x-ray film (Kodak) at −70° C.

VEGFR Binding Assay.

$^{125}$I-VEGFR or PMN are incubated with varying concentrations of proteases as above. The binding of $^{125}$I-VEGFR exposed to proteases to normal PMN, or the binding of normal $^{125}$I-VEGFR to PMN exposed to proteases, are quantified using scintillation. Briefly, $10^5$ cells are incubated with varying concentrations of $^{125}$I-VEGFR in 96-well filter plates (Millipore) in the presence of protease inhibitors. Cells are washed three times by vacuum aspiration and 30 µL of scintillation fluid (Wallac) are added to each well. Scintillation are counted on a Wallac Microbeta scintillation counter (adapted from van Kessel et al., J. Immunol. (1991) 147: 3862-3868 and Porteau et al., JBC (1991) 266:18846-18853).

Example 17

Measuring Activity of MT-SP1 in Serum

The activity of MT-SP1 and trypsin was assayed in the presence of increasing concentrations of fetal calf serum. The high concentrations of macromolecular protease inhibitors present in serum makes it a good in vitro system to test whether a protease would be active in vivo. MTSP and trypsin were resuspended in Dulbecco's Modified Eagle's Medium (DMEM) at 100 nM and 80 nM, respectively, with increasing serum concentrations (0-10%) in a final volume of 100 µL. A fluorogenic peptide substrate (Leu-Val-Arg-aminomethyl-coumarin) was added to a final concentration of 15 µM and fluorescence was detected in a fluorescence plate reader (Molecular Devices) with an excitation wavelength of 380 nm and an emission wavelength of 460 nm.

Figure 5:
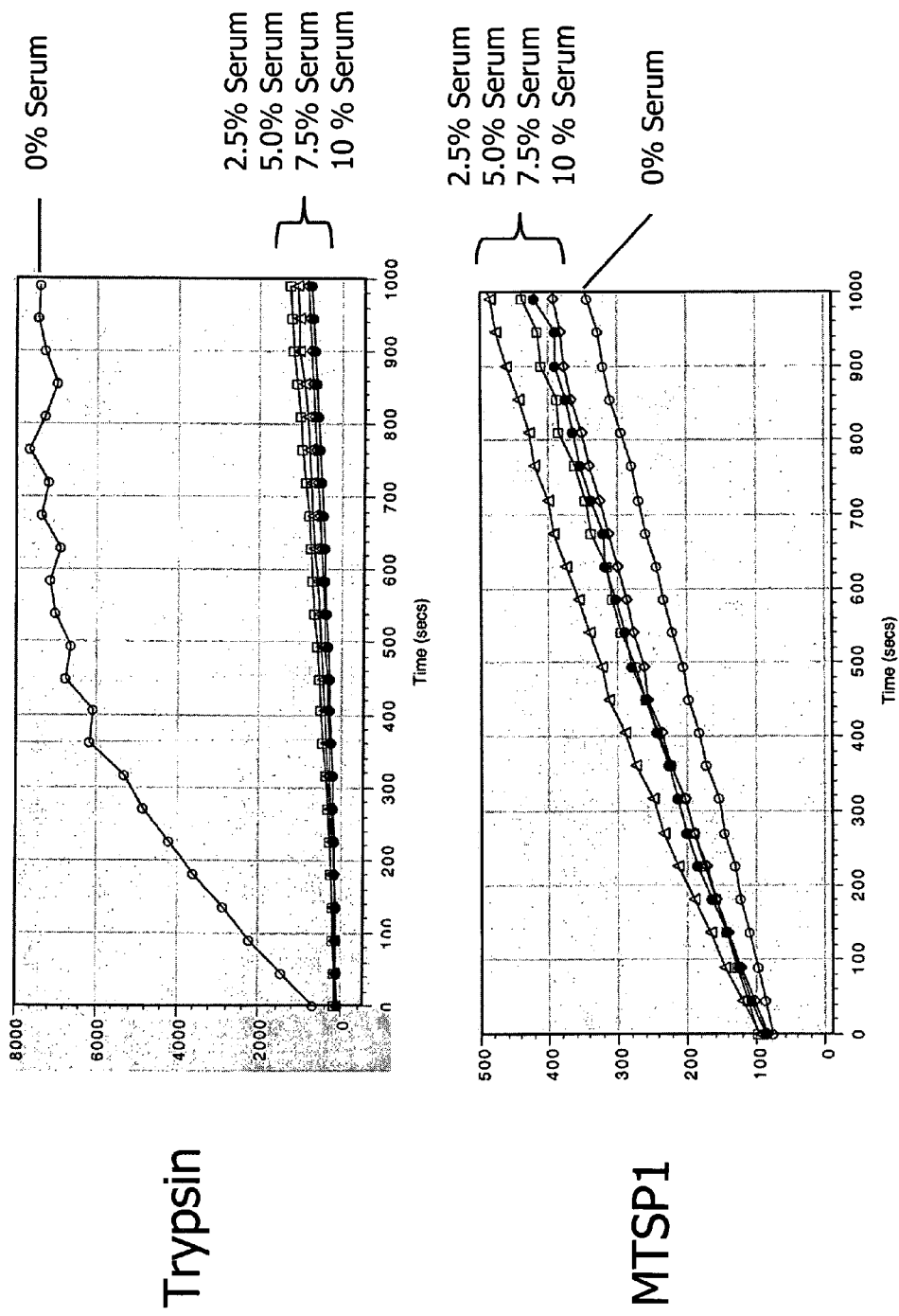
FIG. 5 is a graphical representation of trypsin and MT-SP1 protease activity over time in the presence of increasing levels of serum.

As shown in FIG. 5, trypsin shows very strong activity in 0% serum, with the enzyme using up all the substrate after ~400 seconds. However, even in the lowest concentration of serum (2.5%), trypsin activity is drastically reduced, presumably due to the binding of macromolecular protease inhibitors. MT-SP1, on the other hand, shows virtually the same activity in all concentrations of serum, suggestive that there are no endogenous protease inhibitors in serum that inactivate MT-SP1.

EQUIVALENTS

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. The choice of screening method, protease scaffold, or library type is believed to be a matter of routine for a person of ordinary skill in the art with knowledge of the embodiments described herein. Other aspects, advantages, and modifications considered to be within the scope of the following claims.

What is claimed is:

1. A mutein membrane type serine protease 1 (MT-SP1) protease that comprises at least one mutation in a scaffold MT-SP1 polypeptide, whereby the substrate specificity or activity of the mutein MT-SP1 polypeptide is altered compared to the scaffold MT-SP1 polypeptide, wherein:
the scaffold MT-SP1 polypeptide comprises a sequence of amino acids that is at least 95% identical or is identical to the amino acid sequence of a wild type MT-SP1 whose sequence is set forth in SEQ ID NO:1 or SEQ ID NO:2 or is a species variant of the wild type MT-SP1 of SEQ ID NO:1, or is a catalytically active portion thereof;
the mutein MT-SP1 comprises a mutation at a position selected from among amino acid positions 41, 146, 151, 169, 170, 172, 173, 175, 176, 177, 178, 179, 181, and 224; and
the numbering is for chymotrypsin.

2. The mutein MT-SP1 protease of claim 1, wherein the mutein MT-SP1 comprises a mutation at a position selected from among 146, 172, 175 and 224.

3. The mutein MT-SP1 protease of claim 1, wherein the scaffold MT-SP1 polypeptide comprises the sequence of amino acids set forth in SEQ ID NO:1 or SEQ ID NO:2 or a catalytically active portion thereof.

4. The mutein MT-SP1 protease of claim 2, wherein the scaffold MT-SP1 polypeptide comprises the sequence of amino acids set forth in SEQ ID NO:1 or SEQ ID NO:2 or a catalytically active portion thereof.

5. The mutein MT-SP1 protease of claim 1, wherein the sequence of the scaffold protease is set forth in SEQ ID NO:1 or is a catalytically active portion thereof.

6. The mutein MT-SP1 protease of claim 1, wherein the sequence of the scaffold protease is set forth in SEQ ID NO:2 or is a catalytically active portion thereof.

7. A pharmaceutical composition, comprising a mutein MT-SP1 protease of claim 1.

8. The mutein MT-SP1 protease of claim 2, wherein the mutation is selected from among mutations corresponding to Y146F, Y146N, Y146D, Y146E, Y146A, Y146W, Y146R, L172N, L172D, L172E, L172A, L172V, L172F, L172R, Q175D, Q175E, Q175A, Q175V, Q175F, Q175R, K224A, K224F, K224V and K224D.

9. The mutein MT-SP1 protease of claim 8, wherein the scaffold MT-SP1 polypeptide comprises the sequence of amino acids set forth in SEQ ID NO:1 or SEQ ID NO:2 or a catalytically active portion thereof.

10. The mutein MT-SP1 of claim 9, further comprising an additional mutation selected from among mutations corresponding to Y146F, Y146N, Y146D, Y146E, Y146A, Y146W, Y146R, L172N, L172D, L172E, L172A, L172V, L172F, L172R, Q175D, Q175E, Q175A, Q175V, Q175F, Q175R, K224A, K224F, K224V, and K224D.

11. The mutein MT-SP1 protease of claim 10, comprising mutations selected from among the mutations corresponding to L172D/Q175D, Y146D/K224F, or Y146D/L172D/Q175D.

12. The mutein MT-SP1 of claim 10, wherein the scaffold MT-SP1 polypeptide comprises the sequence of amino acids set forth in SEQ ID NO:1 or SEQ ID NO:2.

13. The mutein MT-SP1 protease of claim 8, further comprising one or more additional mutations.

14. The mutein MT-SP1 protease of claim 13, wherein an additional mutation is selected from among mutations corresponding to Y146F, Y146N, Y146D, Y146E, Y146A, Y146W, Y146R, L172N, L172D, L172E, L172A, L172V, L172F, L172R, Q175D, Q175E, Q175A, Q175V, Q175F, Q175R, K224A, K224F, K224V, and K224D.

15. The mutein MT-SP1 protease of claim 14, wherein at least one mutation is selected from among L172D, Y146F, Q175D and K224F.

16. The mutein MT-SP1 protease of claim 15, wherein the mutein MT-SP1 has the amino acid mutation K224F.

17. The mutein MT-SP1 protease of claim 14, comprising mutations selected from among the mutations corresponding to L172D/Q175D, Y146D/K224F or Y146D/L172D/Q175D.

* * * * *